(12) United States Patent
Gladyshev

(10) Patent No.: US 11,180,811 B2
(45) Date of Patent: Nov. 23, 2021

(54) MOLECULAR SIGNATURES OF CONDITIONS ASSOCIATED WITH LONGEVITY

(71) Applicant: The Brigham and Women's Hospital, Inc., Boston, MA (US)

(72) Inventor: Vadim Gladyshev, Brookline, MA (US)

(73) Assignee: The Brigham and Women's Hospital Inc., Boston, MA (US)

( * ) Notice: Subject to any disclaimer, the term of this patent is extended or adjusted under 35 U.S.C. 154(b) by 0 days.

(21) Appl. No.: 16/013,135

(22) Filed: Jun. 20, 2018

(65) Prior Publication Data
US 2018/0298446 A1 Oct. 18, 2018

Related U.S. Application Data

(63) Continuation of application No. 14/802,250, filed on Jul. 17, 2015, now abandoned.

(60) Provisional application No. 62/025,687, filed on Jul. 17, 2014.

(51) Int. Cl.
*C12Q 1/6883* (2018.01)
*C12Q 1/6876* (2018.01)

(52) U.S. Cl.
CPC ......... *C12Q 1/6883* (2013.01); *C12Q 1/6876* (2013.01); *C12Q 2600/118* (2013.01); *C12Q 2600/158* (2013.01)

(58) Field of Classification Search
CPC .............. C12Q 1/6883; C12Q 1/6876; C12Q 2600/118; C12Q 2600/158
See application file for complete search history.

(56) References Cited

U.S. PATENT DOCUMENTS

2010/0173024 A1    7/2010   McDaniel

OTHER PUBLICATIONS

Saito-Hisaminato et al. DNA Research. 2002. 9:35-45. (Year: 2002).*
Abzhanov et al., "Bmp4 and morphological variation of beaks in Darwin's finches", Science 305(5689):1462-1465 (2004).
Alic et al., "Death and dessert: nutrient signalling pathways and ageing", Curr Opin Cell Biol. 23(6):738-743 (2011).
Anderson et al., Metabolic reprogramming, caloric restriction and aging, Trends Endocrinol Metab. 21(3):134-141 (2010).
Austad "Comparative biology of aging", J Gerontol A Biol Sci Med Sci. 64(2):199-201 (2009).
Barbosa-Morais et al., "The evolutionary landscape of alternative splicing in vertebrate species", Science. 338 (6114):1587-1593 (2012).
Beldade et al. "Contribution of Distal-less to quantitative variation in butterfly eyespots". Nature 415(6869):315-318 (2002).
Blomberg et al., "Testing for phylogenetic signal in comparative data: behavioral traits are more labile", Evolution 57 (4):717-745 (2003).
Carroll et al., "Evolution at two levels: on genes and form", PLoS Biol. 3(7):e245 (2005).
Danko et al., "Mutation accumulation may be a minor force in shaping life history traits", PLoS One. 7(4):e34146 (2012).
Fraser "Gene expression drives local adaptation in humans", Genome Research 23:1089-1096 (2013).
Gompel et al., "Chance caught on the wing: cis-regulatory evolution and the origin of pigment patterns in Drosophila", 433(7025):481-487 (2005).
Janecka et al., "Exploring the correlations between sequence evolution rate and phenotypic divergence across the Mammalian tree provides insights into adaptive evolution", J Biosci. 37(5):897-909 (2012).
Khaitovich et al., "A neutral model of transcriptome evolution", PLoS Biol. 2(5):0682-0689 (2004).
Lee et al., "Gene Expression profile of aging and its retardation by caloric restriction", Science 285(5432): 1390-1393 (1999).
Li et al., "Accelerated protein evolution analysis reveals genes and pathways associated with the evolution of mammalian longevity", Age 35:301-314 (2013).
Losos et al., "Contingency and determinism in replicated adaptive radiations of island lizards", Science 279 (5359):2115-2118 (1998).
Quarrie et al., "Murine models of life span extension", Sci Aging Knowledge Environ. 2004(31):re5 (2004).
Semeiks et al., "A method to find longevity-selected positions in the mammalian proteome", PLoS One. 7(6):e38595 (2012).
Shapiro et al., "Genetic and developmental basis of evolutionary pelvic reduction in threespine stickbacks", Nature 428:717-723 (2004).
Tofts et al., "A phylogenetic approach to community assembly from a local species pool", Proc R. Biol Sci. 267 (1441):363-369 (2000).
Yanai et al., "Incongruent expression profiles between human and mouse orthologous genes suggest widespread neutral evolution of transcription control", OMICS 8(1):15-24 (2004).
Yuan et al., "Mice as a mammalian model for research on the geentics of aging", ILAR J. 52(1):4-15 (2011).

* cited by examiner

*Primary Examiner* — Joseph G. Dauner
(74) *Attorney, Agent, or Firm* — Nixon Peabody LLP; David S. Resnick; Teresa A. Ptashka

(57) ABSTRACT

The invention provides a collection of gene expression signatures that is linked to longevity. Also provided herein are assays, methods, and systems for identifying a treatment that can modulate lifespan or determining an effect of a treatment on a health profile of a subject by using the collection of gene expression signatures described herein.

3 Claims, 31 Drawing Sheets

MOLECULAR SIGNATURES OF CONDITIONS ASSOCIATED WITH LONGEVITY

CROSS-REFERENCE TO RELATED APPLICATION

This application is a Continuation of U.S. application Ser. No. 14/802,250 filed Jul. 17, 2015, which claims benefit under 35 U.S.C. § 119(e) of U.S. Provisional Application No. 62/025,687 filed Jul. 17, 2014, the contents of which are incorporated herein by reference in its entirety.

GOVERNMENT SUPPORT

This invention was made with government support under grant AG047745 awarded by the National Institutes of Health (NIH). The government has certain rights in the invention.

FIELD OF THE INVENTION

The field of the invention relates to gene expression signature, metabolites, and pathways associated with longevity.

INCORPORATION BY REFERENCE

This application contains a table which has been submitted in ASCII format on a CD-R and is hereby incorporated by reference in its entirety. Said ASCII copy, created on Jul. 16, 2015, is named Table5_043214-082131-US.pdf and is 3,777 KB in size. The CD-R and a duplicate copy have been submitted to the USPTO by Express Mail (Express Mail No. EM 197899905 US).

BACKGROUND

Extant mammals diversified dramatically, featuring more than 100 fold difference in lifespan, 100 million fold difference in body mass and adaptations to both terrestrial and aquatic life as well as to powered flight and subterranean life. Nature has been continuously and reversibly adjusting morphology and life histories of mammals while preserving fitness, but how it does this, and what the molecular processes are involved, remains unclear. Accumulating evidence suggests a role of widespread heritable variation combined with extensive natural variation in gene expression within and between heterologous mammalian populations (Brawand et al., 2011). Although much of the variation is thought to evolve under neutral drift, the variation in expression of numerous genes exhibited environmental selection constraints (Jordan et al., 2005; Whitehead and Crawford, 2006). The extent to which evolution of gene expression contributes to mammalian traits is subject to debate. It is of fundamental importance to estimate the rate and patterns of gene expression changes among and within taxa and to characterize the underlying forces shaping evolution of the mammalian transcriptome.

Predominant neutrality of gene expression changes evolving under minimal or no selective constraints over time was proposed as a primarily model for evolution of transcriptomes (Khaitovich et al., 2004a; Yanai et al., 2004). However, the null effect of gene expression changes on phenotypes is questionable, since numerous case studies showed that gene expression alterations can result in drastic phenotypic effects, such as changes in lifespan (Quarrie &

Riabowol, 2004; Yuan et al., 2011) and morphological differences (Shapiro et al., 2004; Gompel et al., 2005; Beldade et al., 2002; Abzhanov et al., 2004). While inherited and acquired genetic variants may feature low predictable effects on phenotypes, gene expression profiles can be coordinately modified in response to environmental signals, thereby promoting specific phenotypic outcomes. Dietary interventions, such as caloric restriction, which do not affect genetic structure, may control lifespan of diverse species by modulating the transcription of specific genes and remodeling metabolism (Austad, 2009; Alic & Partridge, 2011; Anderson & Weindruch, 2009; Lee et al., 1999). Fundamental evolutionary questions, such as which forces govern the variance in transcript levels among and within distant mammalian taxa, and how these variations connect genomic content and phenotypes, have only begun to be understood.

Mammals differ dramatically in their life history strategies and, therefore, represent a model for uncovering mechanisms and underlying forces that govern evolution of phenotypes. Interspecific competition could change adaptive strategies of lineages in opposite directions, whereas environmental cues could lead to convergence in molecular mechanisms that underlie phenotypes (Losos et al., 1998; Tofts & Silvertown, 2000). Lifespan, like other life history traits, exhibits a moderate phylogenetic signal (Blomberg et al., 2003) that, at the molecular level, could be explained by accumulation of sequence polymorphisms and interspecies variation in transcription levels over time (Barbosa-Morais et al., 2012; Janecka et al., 2012). However, the interplay between and within heritable and environmental components directing micro- and macroevolution of morphological traits has been questioned (Stearns, 2000).

Genetic diversity of mammals has a limited power in interpreting life history variation because the predominant portion of sequence changes is functionally neutral (Li & de Magalhaes, 2011; Semeiks & Grishin, 2012; Danko et al., 2012). It was proposed that adaptive changes in morphology and development are more evident in alterations in gene expression than in protein sequences (Carroll, 2005). Indeed, local ecological adaptations are 10-fold more likely to affect gene expression than amino acid sequences (Fraser, 2013). Therefore, studies on gene evolution at the expression level could provide further insights in phenotype evolution.

SUMMARY

By comparing gene expression and metabolite levels in various organs across species of mammals with different lifespan, the inventors have identified a collection of gene expression signatures associated with longevity as set forth in FIG. 4, FIG. 5, FIG. 9, or Table 5, where some genes are upregulated and others are downregulated.

In one aspect, provided herein is a collection of gene expression signatures as set forth in FIG. 4, FIG. 5, FIG. 9, or Table 5, or a combination thereof that are upregulated.

In another aspect, provided herein is a collection of gene expression signatures as set forth in FIG. 4, FIG. 5, FIG. 9, or Table 5, or a combination thereof that are downregulated.

In one aspect, a method is provided herein for screening a treatment that affects a health profile of a subject, the method comprising: (a) administering the treatment to the subject or a cell obtained from the subject; and (b) measuring, in a sample obtained from the subject or the cell, an effect of the treatment on the expression of at least 10 genes set forth in FIG. 4, FIG. 5, FIG. 9, or Table 5, or a combination thereof as compared to a reference.

In some embodiments, the treatment comprises administration of an agent, a lifestyle change, a change in disease status, or a combination thereof.

In some embodiments, the agent comprises a small molecule, a peptide, a peptidomimetic, an RNA interference molecule, an antibody, an aptamer, or a gene therapy.

In some embodiments, the agent is a geroprotector.

In some embodiments, the lifestyle change comprises a change in exercise status, a dietary change, a change in smoking status, a change in alcohol or substance use, a change in stress levels, or a combination thereof.

In some embodiments, the subject is a mammal.

In some embodiments, the mammal is a human.

In some embodiments, the reference is a gene expression profile of the at least 10 genes set forth in FIG. 4, FIG. 5, FIG. 9, or Table 5, or a combination thereof of the subject prior to the treatment.

In one aspect, an assay is provided herein for identifying a treatment that can modulate lifespan, the assay comprising: (a) administering a treatment to a cell, cell line, or mammal; (b) measuring, in the cell, cell line or a biological sample obtained from the mammal, a gene expression profile of at least 10 genes set forth in FIG. 4, FIG. 5, FIG. 9, or Table 5, or a combination thereof; (c) comparing the gene expression profile of the at least 10 genes with a reference longevity signature, wherein if the gene expression profile is at least 75% similar to the reference longevity signature, the treatment is predicted to increase lifespan, and wherein if the gene expression profile is less than 75% similar to the reference longevity signature, the treatment is predicted to have no effect on lifespan or decrease lifespan.

In some embodiments, the treatment comprises administration of an agent, a lifestyle change, a change in disease status, or a combination thereof.

In some embodiments, the agent comprises a small molecule, a peptide, a peptidomimetic, an RNA interference molecule, an antibody, an aptamer, or a gene therapy.

In some embodiments, the agent is a geroprotector.

In some embodiments, the lifestyle change comprises a change in exercise status, a dietary change, a change in smoking status, a change in alcohol or substance use, a change in stress levels, or a combination thereof.

In some embodiments, the reference longevity signature comprises a gene expression profile of at least one mammal having a long lifespan.

In some embodiments, step (b) comprises measuring the gene expression profile of at least 20 genes, at least 100 genes, at least 500 genes, or at least 1000 genes set forth in FIG. 4, FIG. 5, FIG. 9, or Table 5, or a combination thereof.

In some embodiments, the biological sample comprises whole blood, plasma, serum, liver, kidney or brain tissue.

In some embodiments, the mammal is a human.

In one aspect, an assay is provided herein for identifying a treatment that can modulate lifespan, the assay comprising: (a) administering a treatment to a cell, cell line, or mammal; (b) measuring, in the cell, cell line or a biological sample obtained from the mammal, a gene expression profile of at least 10 genes set forth in FIG. 4, FIG. 5, FIG. 9, or Table 5, or a combination thereof; (c) determining a longevity score as a function of the measurement in step (b); and (d) comparing the longevity score with a reference score determined from a reference longevity signature associated with the at least 10 genes, wherein if the longevity score is at or above the reference score, the treatment is predicted to increase lifespan, and wherein if the longevity score is below the reference, the treatment is predicted to have no effect on lifespan or decrease lifespan.

In some embodiments, the treatment comprises administration of an agent, a lifestyle change, a change in disease status, or a combination thereof.

In some embodiments, the agent comprises a small molecule, a peptide, a peptidomimetic, an RNA interference molecule, an antibody, an aptamer, or a gene therapy.

In some embodiments, the agent is a geroprotector.

In some embodiments, the lifestyle change comprises a change in exercise status, a dietary change, a change in smoking status, a change in alcohol or substance use, a change in stress levels, or a combination thereof.

In some embodiments, the reference longevity signature comprises a gene expression profile of at least one mammal having a long lifespan.

In some embodiments, step (b) comprises measuring the gene expression profile of at least 20 genes, at least 100 genes, at least 500 genes, or at least 1000 genes set forth in FIG. 4, FIG. 5, FIG. 9, or Table 5, or a combination thereof.

In some embodiments, the biological sample comprises whole blood, plasma, serum, liver, kidney or brain tissue.

In some embodiments, the mammal is a human.

In another aspect, an assay is provided herein for identifying a treatment that can modulate lifespan, the assay comprising: (a) administering a treatment to a cell, cell line, or mammal; (b) measuring, in the cell, cell line or a biological sample obtained from the mammal, expression levels of at least 10 of the upregulated genes set forth in FIG. 4, FIG. 5, FIG. 9, or Table 5, or a combination thereof and at least 10 of the downregulated genes set forth in FIG. 4, FIG. 5, FIG. 9, or Table 5, or a combination thereof; (c) determining a gene expression ratio of the at least 10 of the upregulated genes set forth in FIG. 4, FIG. 5, FIG. 9, or Table 5, or a combination thereof and the at least 10 of the downregulated genes set forth in FIG. 4, FIG. 5, FIG. 9, or Table 5, or a combination thereof; and (d) comparing the gene expression ratio with a reference ratio determined for a reference gene expression profile associated with a longevity signature.

In yet another aspect, an assay is provided herein for determining an effect of a treatment on a health profile of a subject, the assay comprising: (a) administering the treatment to the subject or a cell obtained from the subject; and (b) measuring, in a sample obtained from the subject or the cell, the effect of the treatment on the expression of at least 10 genes set forth in FIG. 4, FIG. 5, FIG. 9, or Table 5, or a combination thereof as compared to a reference.

In some embodiments, the reference is a gene expression profile of the at least 10 genes set forth in FIG. 4, FIG. 5, FIG. 9, or Table 5, or a combination thereof of the subject prior to the treatment.

BRIEF DESCRIPTION OF THE FIGURES

The patent or application file contains at least one drawing executed in color. Copies of this patent or patent application publication with color drawing(s) will be provided by the Office upon request and payment of the necessary fee.

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

(FIG. 1A) Chronogram tree demonstrating phylogenetic relationships of mammals. Bootstrap support for the branching order of 33 species was reconstructed with 1000 randomization steps. Species divergence time is plotted as upper and lower-bounded intervals (grey bars). (FIG. 1B) Comparative plots of the life histories. From left to right: time to maturity, maximum lifespan and oxygen consumption. Each bar denotes a value of life history variable for a particular organism in standard scale.

(FIG. 2A) Female maturation time. (FIG. 2B) Male maturation time. (FIG. 2C) Gestation period. (FIG. 2D) Weaning time. (FIG. 2E) Birth weight. (FIG. 2F) Weaning weight. (FIG. 2G) Adult weight. (FIG. 2H) Growth (Gompertz coefficient). Number of informative species (n) used in the analysis is indicated in the bottom right corner of each plot. Individual lineages are highlighted with distinct colors (legend in the bottom right corner). Determination coefficient (r) and statistical significance of correlation (P, F-test) are indicated at the top of each panel.

(FIG. 3A) Cumulative expression profiles of transcripts associated with time to maturity. Genes positively correlated with life history variation are plotted on the top panel (pink), and negatively correlated on the bottom panel (blue). Vertical axes denote $\log_2$-ratio of FPKM in standard scale. Horizontal axes denote $\log_2$-ratio of time to maturity. Each rhomb on the plot denotes mean expression value of all genes (n) for a particular organism. Shaded areas denote 60%, 75% and 90% upper and lower quantiles of $\log_2$-ratio distribution. (FIG. 3B) A cluster map that shows gene ontology (GO) terms for genes associated with gradient of life history variation. Columns on the plot correspond to a particular trait (indicated at the bottom). Rows on the plot show GO terms. Upregulated GO terms are in red. Downregulated GO terms are in blue. Magnitude of respective color denotes statistical significance of enrichment (negative logarithm of FDR-corrected P-value, bar at the bottom). (FIG. 3C) Conservation scores for molecules associated with gradient of time to maturity variation. Each panel shows distributions of per-residue similarity scores for up- (pink) and down- (blue) regulated molecules for the liver, kidney or brain. Numbers of individual orthologous groups examined in the analysis are indicated at the bottom of each bar. Significance of the difference between distributions was assessed with two-tailed Welch's t-tests (P-values at the top). (FIG. 3D) Shannon's information entropy for molecules significantly associated with gradient of time to maturity variation. Each panel shows distributions of per-residue entropy scores for up- (pink) and down- (blue) regulated genes for the liver, kidney or brain. (FIG. 3E) A model of parallel accumulation of changes in biological sequences and gene expression. (FIG. 3F) Overlap between gene sets associated with gradients of life history variation and database longevity genes (mouse, fly, worm and yeast; from the GenAge dataset).

(FIG. 6A) Mean FPKM of all significant genes. Error bars indicate standard deviation of the mean. Grey line is the relative value of life history variable (time to maturity, axis on the right). Species are shown at the bottom. Color-coded rectangles distinguish lineages. Bar at the top right shows proportion of significant genes from all genes associated with this pathway. P-value denotes statistical enrichment (right-sided hypergeometric test). (FIG. 6B) Genes whose expression variation correlates with life history variation. Vertical axis is the relative FPKM $\log_2$-transformed. Horizontal axis is the relative life history variable in logarithmic space. Rhombs are the means of FPKM. Colors of rhombs distinguish lineages. Error bars show standard deviation of the mean. P-value denotes significance of the OLS model. Median grey line is best-fit OLS line. Shaded areas indicate observed and predicted upper (95%) and lower (5%) confidence intervals. (FIG. 6C) Functional interaction network. Color of nodes denotes significance of the OLS model (scale on the top). Positively correlated genes are in red. Negatively correlated genes are in blue. Color of edges denotes type of interaction (bottom).

(FIG. 7A) and (FIG. 7B) Plots show the residual of maximum lifespan (tmax) and maturation time (tsex) plotted against body weight, respectively. Vertical axes are the residuals log 2-transformed. Horizontal axes denote body weight log 2-transformed. n denotes total numbers of species. Species examined in the study are highlighted with colors (legend at the bottom). Equations in the bottom right corner define linear relationship between respective life histories and body weight. (FIG. 7C) A cluster map that shows GO terms associated with gradient of residual variation. Columns on the plot indicate residuals of tmax and tmax (bottom). Rows show GO terms. Sub rectangles in red denote GO terms positively correlated with residual variable. Negatively correlated GO terms are in blue. Color intensities denote statistical significance of GO term (logarithm of FDR corrected P-value, bottom right corner).

(FIG. 8A) Mean FPKM of all significant genes. Error bars indicate standard deviation of the mean. Grey line is the relative value of residual variable (time to maturity, axis on the right). Species are shown at the bottom. Color-coded rectangles distinguish lineages. Bar at the top right shows proportion of significant genes from all genes associated with this pathway. P-value denotes statistical enrichment (right-sided hypergeometric test). (FIG. 8B) Genes whose expression variation correlates with residual variation. Vertical axis is the relative FPKM log$_2$-transformed. Horizontal axis is the residual of maturation time in logarithmic space. Rhombs are the means of FPKM. Colors of rhombs distinguish lineages. Error bars show standard deviation of the mean. P-value denotes significance of the OLS model. Median grey line is best-fit OLS line. Shaded areas indicate observed and predicted upper (95%) and lower (5%) confidence intervals. (FIG. 8C) Functional interaction network. Color of nodes denotes significance of the OLS model. Positively correlated genes are in red. Negatively correlated genes are in blue. Color of edges denotes type of interaction (bottom).

DETAILED DESCRIPTION

The invention is based, in part, on the discovery that a plurality of genes contribute to longevity in mammals through either upregulation or downregulation. As used herein, the term "longevity" with reference to longevity of an animal refers to a long lifespan of an individual organism compared to a reference organism. For example, a human having a lifespan of 100 years is considered to enjoy longevity compared to a human having a lifespan of less than 100 years (e.g., 90 years, 80 years, 70 years, 60 years or less). Although lifespan can be measured in an individual organism, it is common to measure and compare mean or median lifespan of populations of individual organisms.

Figure 4:
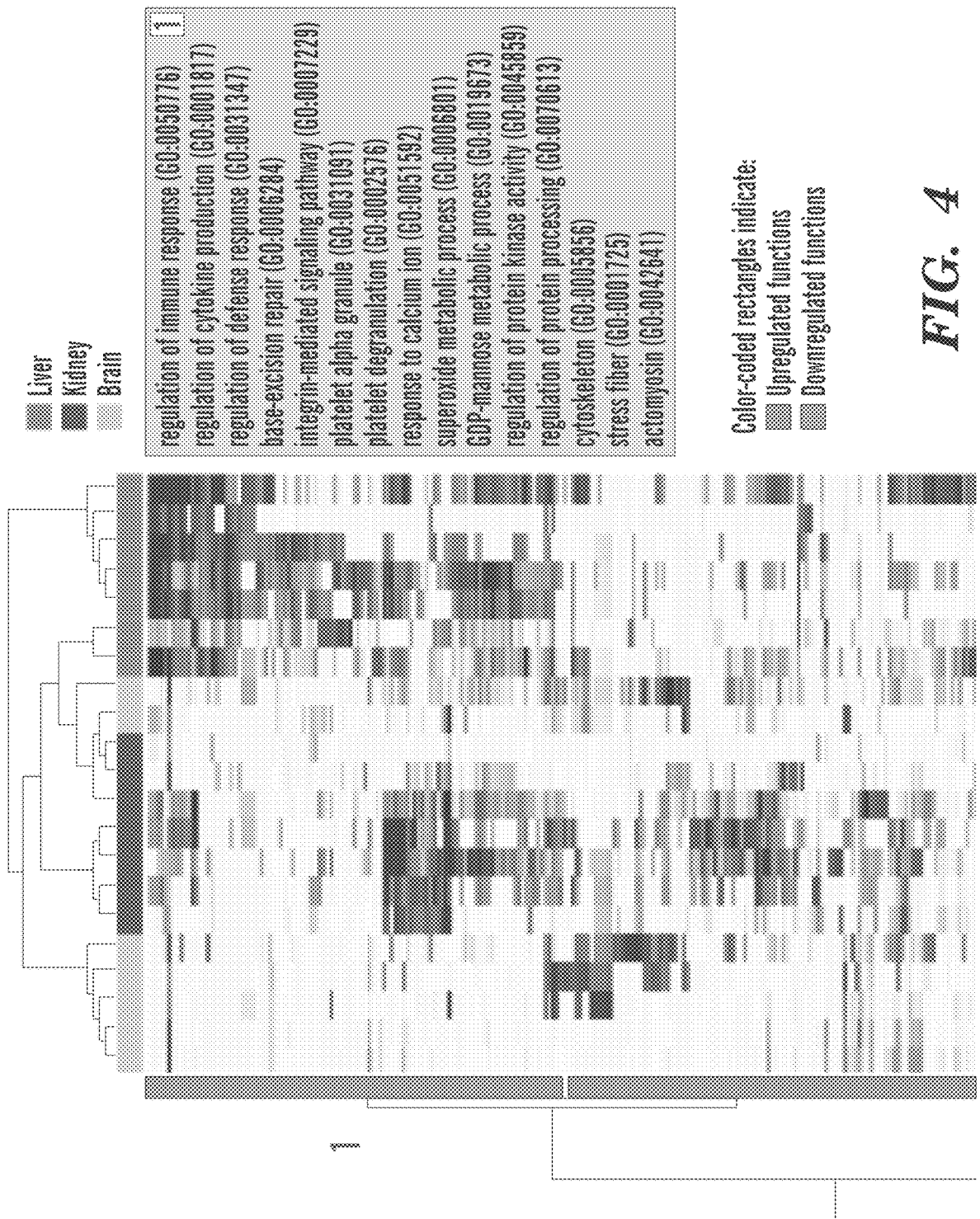
FIG. 4. A cluster map that shows GO terms associated with gradient of life history variation. Columns on the plot correspond to life histories (bottom). Rows show GO terms. Sub rectangles in red denote GO terms positively correlated with life history variables. Negatively correlated GO terms are in blue. Color intensities denote statistical significance of GO term (negative logarithm of FDR corrected P-value, bar in the bottom right corner of plot). Life histories and GO terms were clustered using the Wald method and Euclidean distance metric. GO terms are grouped into 5 clusters (left side). Titles of representative GO terms are presented in the right corner of plot (in brackets).
Figure 4:
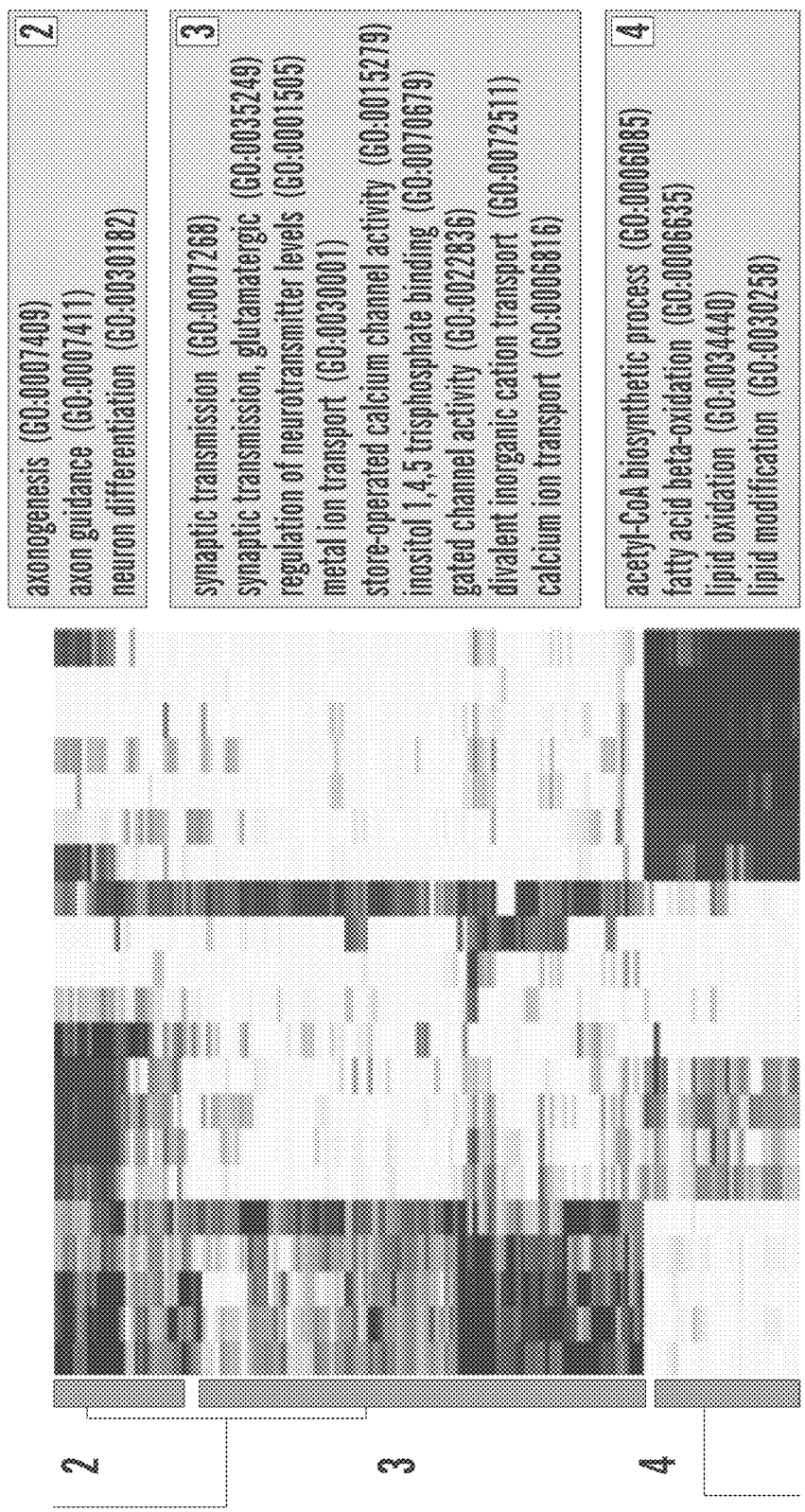
Figure 4:
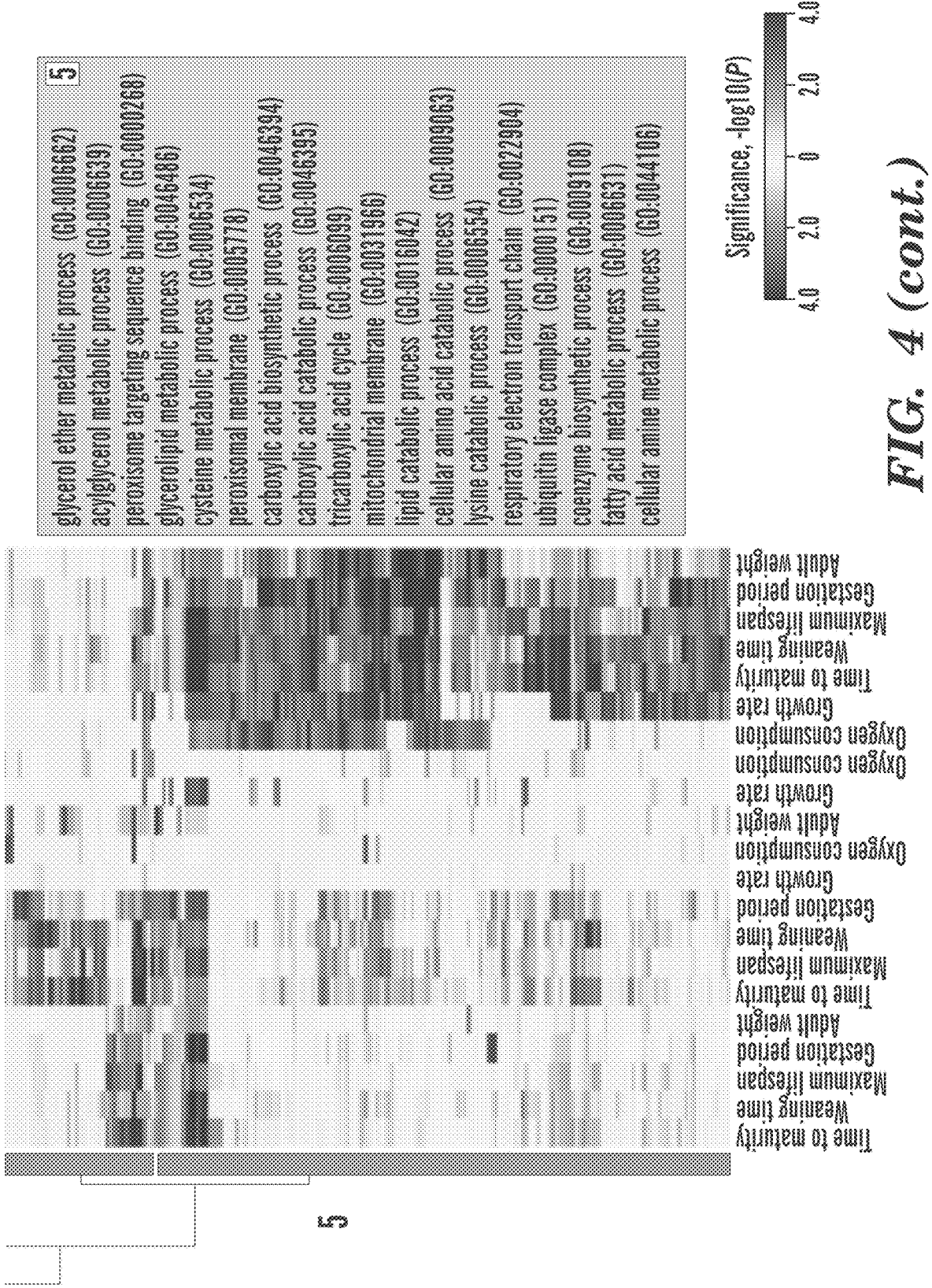
Figure 5:
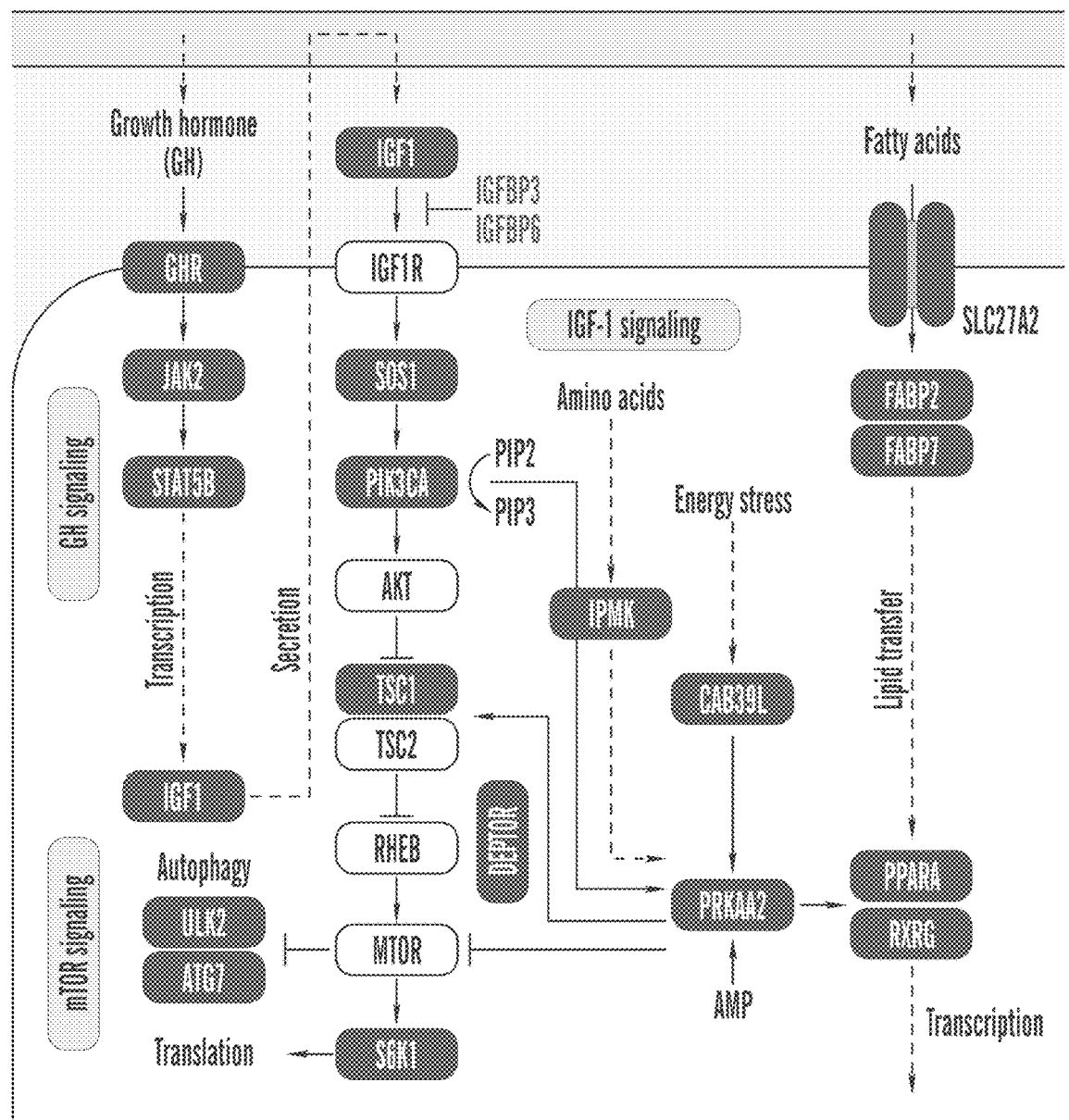
FIG. 5. Schematic overview of genes and functions associated with gradient in lifespan variation in the liver. Rectangles in red indicate upregulated genes (FDR corrected $P<0.05$, F-test) or functions, while rectangles in blue indicate downregulated genes (FDR corrected $P<0.05$, F-test) or functions. Solid arrows denote direct effects (activation) when upstream partners interact with the targets, while dashed lines show an indirect effect (or compound entry in the pathway) occurring during downstream reactions. P-values denote statistical enrichment of biological pathways with significant genes (FDR corrected P, right-sided hypergeometric test). Refer to Table 5 and Dataset 2 (not included) for specific statistical details on genes and GO functions.
Figure 5:
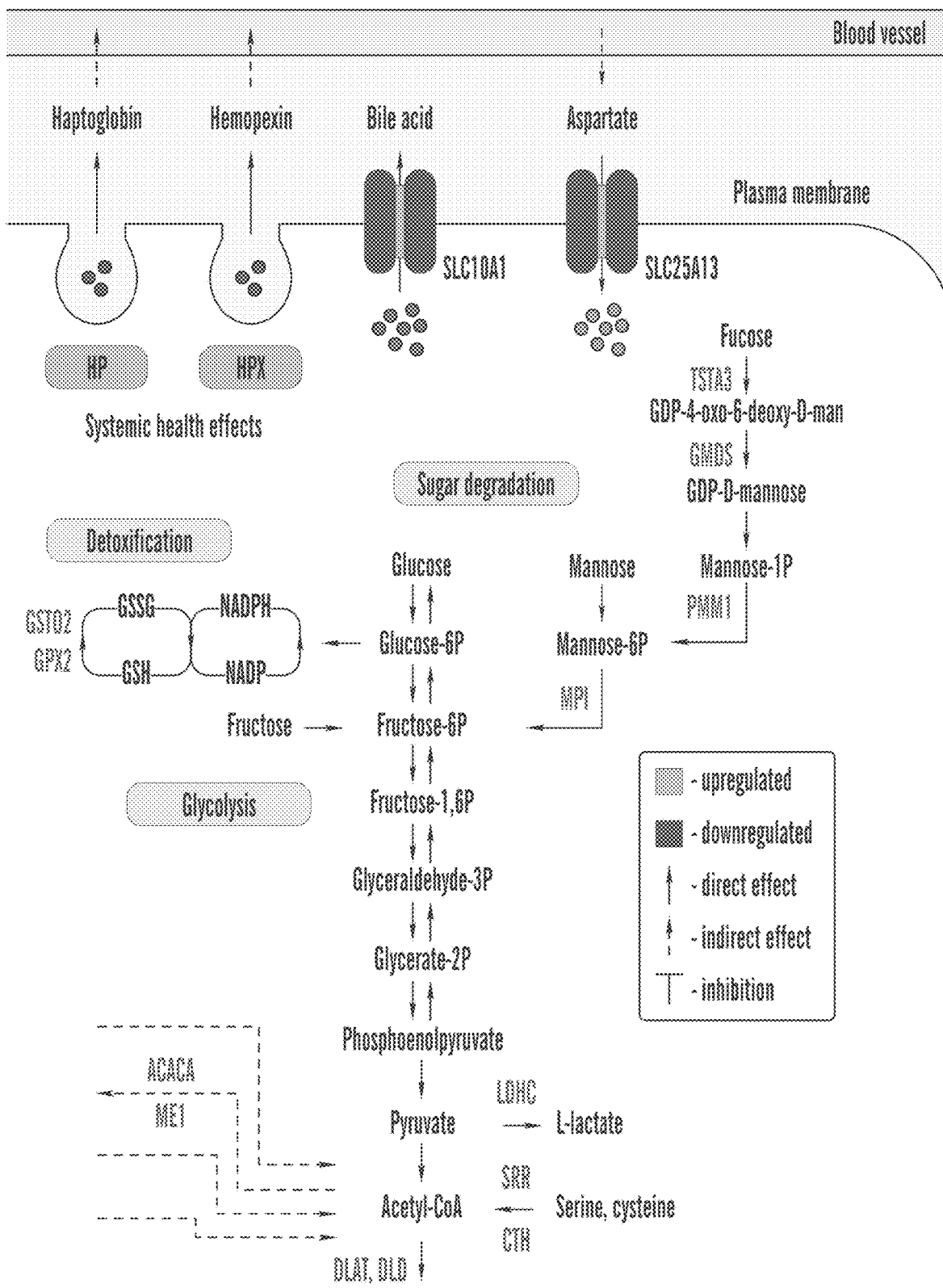
Figure 5:
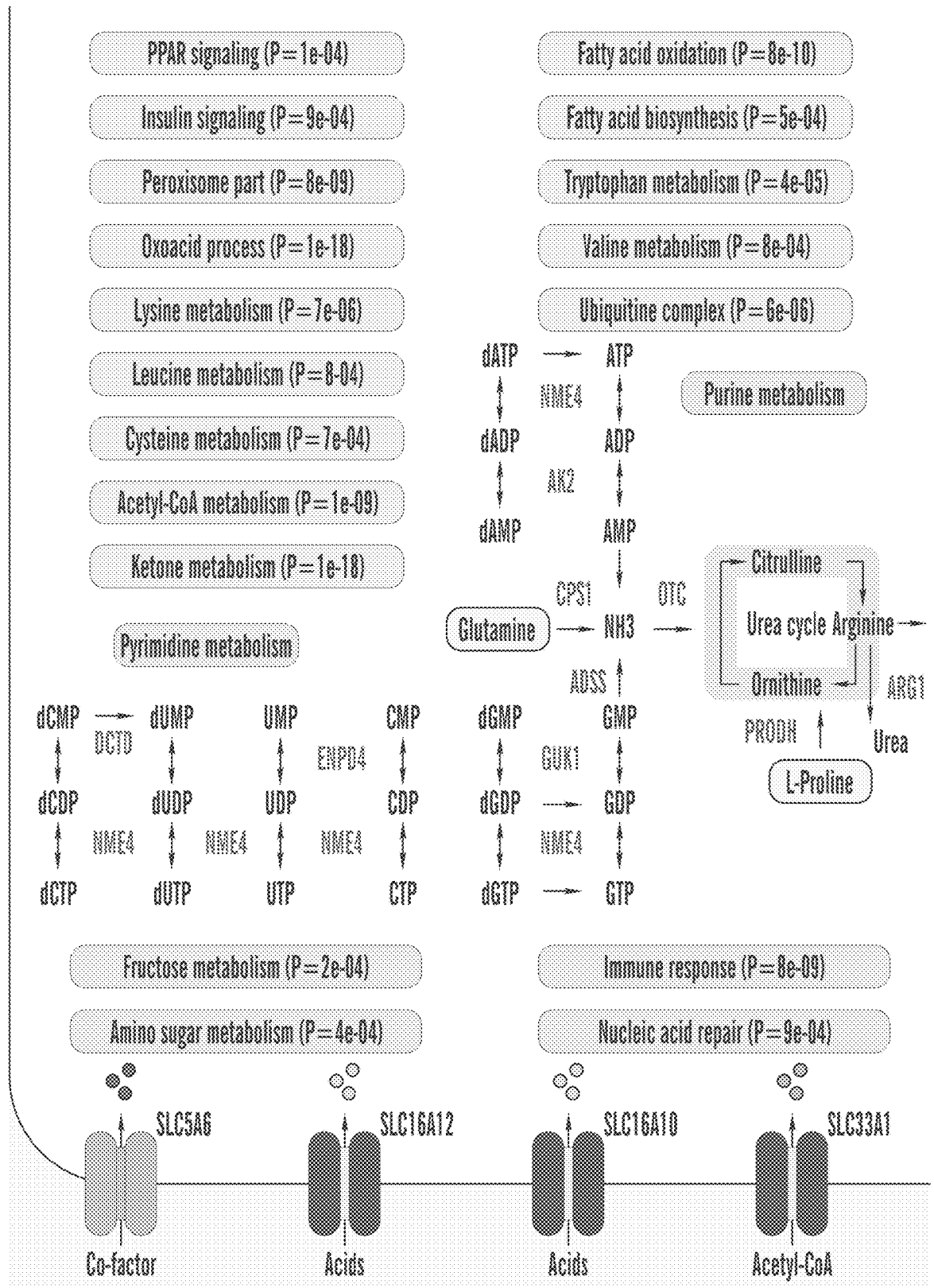
Figure 5:
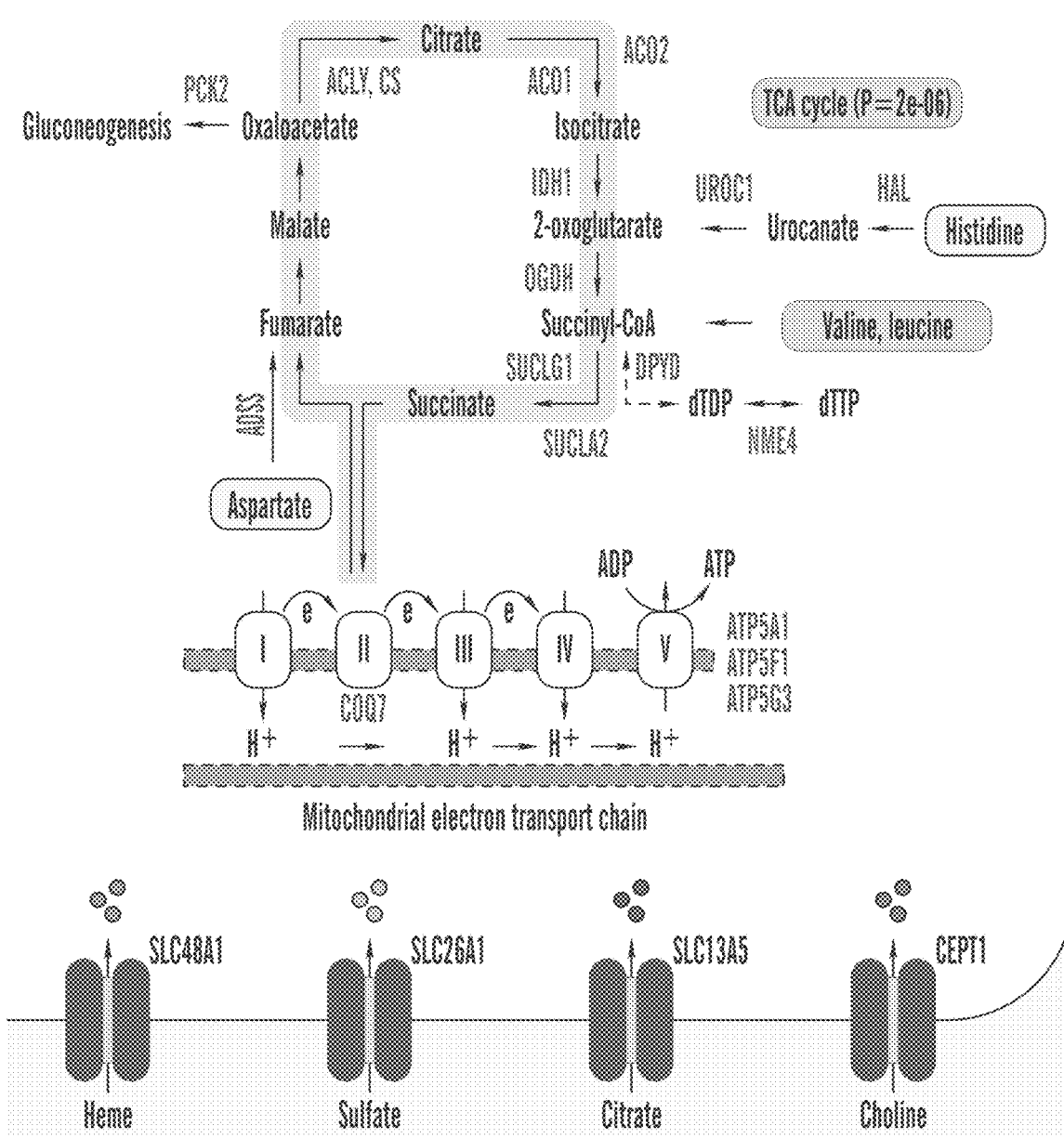
Figure 9:
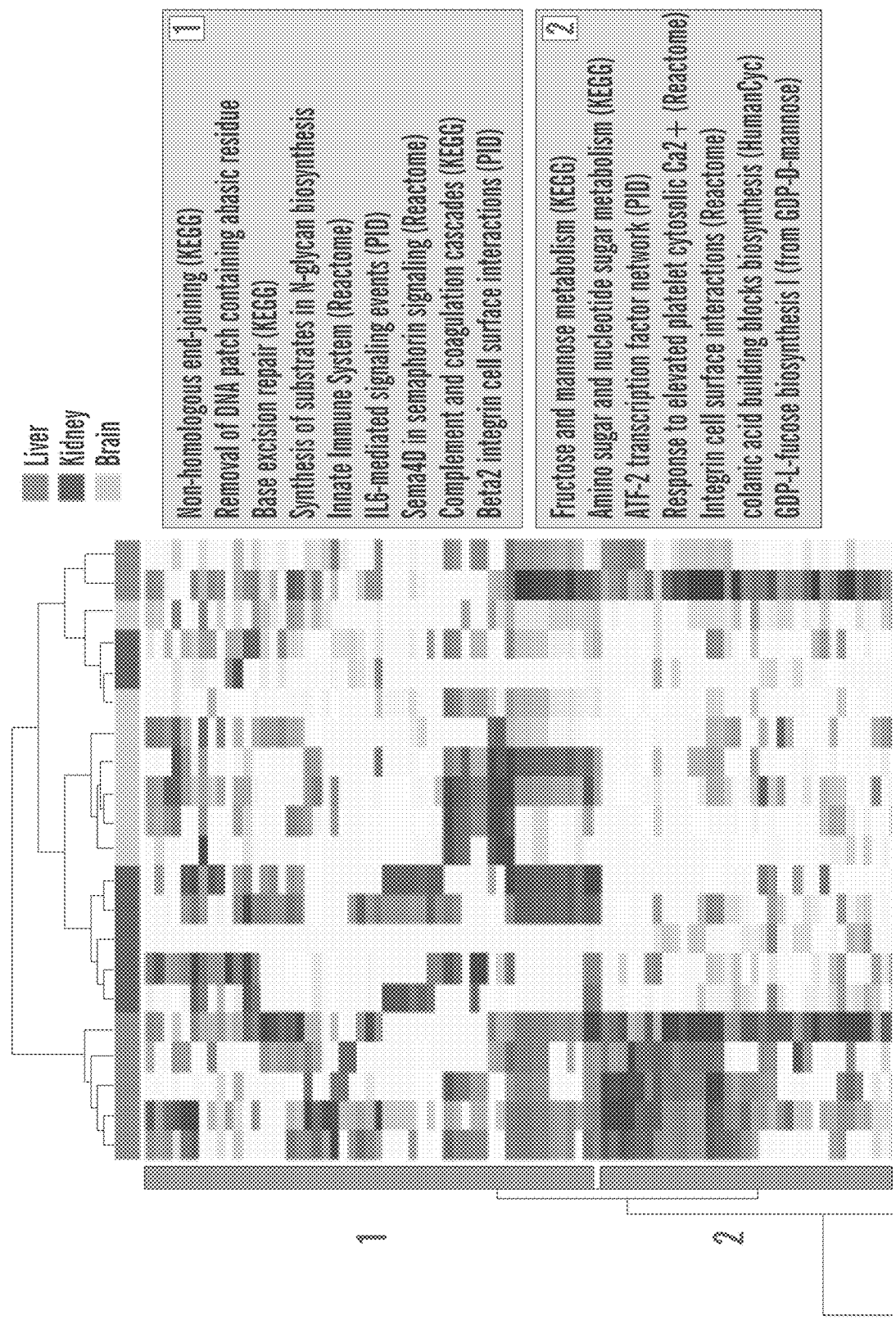
FIG. 9. A cluster map that shows biological pathways associated with life histories. Columns on the plot correspond to life histories (bottom). Rows show pathways. Sub rectangles in red denote pathways positively correlated with life history variable. Negatively correlated pathways are in blue. Color intensities denote statistical significance of enrichment (negative logarithm of FDR-corrected P-value, bar in the bottom right corner of plot). Life histories and pathways were clustered using the Wald method and Euclidean distance metric. Pathways are grouped into 7 clusters (left side). Titles of representative pathways and database source (in brackets) are presented in the right corner of plot.
Figure 9:
Figure 9:
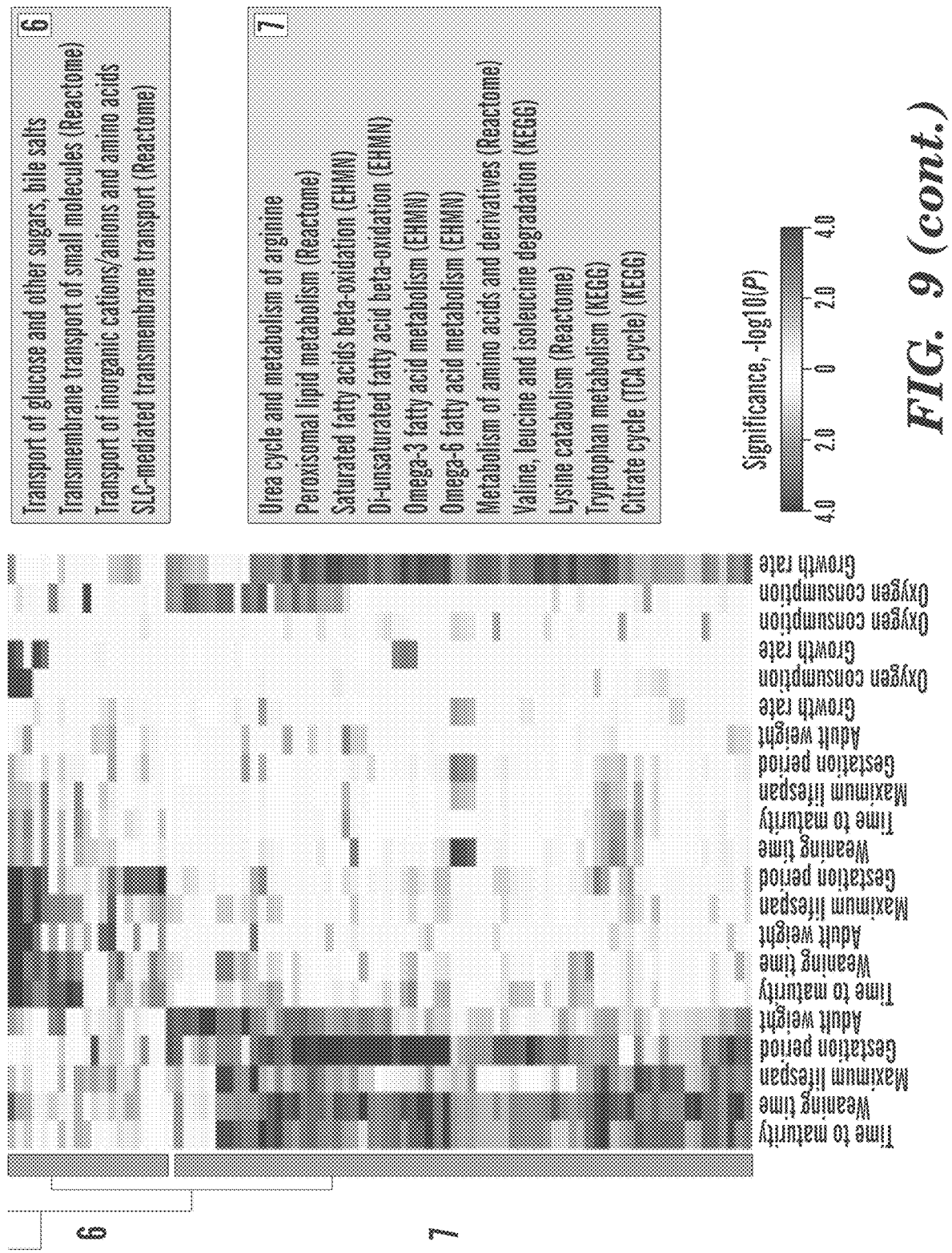

By comparing gene expression and metabolite levels in various organs across species of mammals with different lifespan, the inventors have identified a collection of expression signatures associated with longevity as set forth in FIG. 4, FIG. 5, FIG. 9, or Table 5, where some genes and pathways are upregulated and others are downregulated. At least 0.05%, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% of the genes set forth in FIG. 4, FIG. 5, FIG. 9, or Table 5, or a combination thereof can be used as a marker for longevity. Without wishing to be bound by theory, these gene expression signatures are an evolutionary signature that Nature employs to adjust species lifespan. Accordingly, the invention provides, inter alia, assays, methods, and systems for screening a treatment that can modulate lifespan or affect a health profile of a subject.

Methods and Assays

In one aspect, a method is provided herein for screening a treatment that affects a health profile of a subject, the method comprising: (a) administering the treatment to the subject or a cell obtained from the subject; and (b) measuring, in a sample obtained from the subject or the cell, an effect of the treatment on the expression of at least 10 genes set forth in FIG. 4, FIG. 5, FIG. 9, or Table 5, or a combination thereof as compared to a reference. As used herein, the term "health profile" refers to a set of values and/or qualitative descriptors, each value and/or descriptor representing a particular aspect of the health status of the subject. The measurement is performed, for example, about a day, about a week, about two weeks, about three weeks, about a month, about two months, or about three months, after the administration of the treatment.

By monitoring the change in the gene expression before and after treatment, a physician can identify whether the treatment has a positive, neutral, or negative effect on a gene that should be upregulated or downregulated. For example, a positive effect on a gene that should be upregulated can mean that the gene is upregulated to a greater extent after the treatment. In another example, a positive effect on a gene that should be upregulated can also mean that the gene downregulated or not regulated prior to treatment becomes upregulated after the treatment. Similarly, a negative effect on a gene that should be upregulated can mean that the gene is upregulated to a less extent after the treatment. A negative effect on a gene that should be upregulated can also mean that the gene upregulated prior to the treatment becomes non-regulated or downregulated after the treatment. A neutral effect means that the expression level of the gene is not affected due to the treatment. The overall effect of the treatment on the health profile of the subject should take into account the effects on each and every one of the genes being measured.

In some embodiments, step (b) of the method comprises measuring an effect of the treatment on the expression of at least 20 genes, at least 50 genes, at least 100 genes, at least 200 genes, at least 500 genes, or at least 1000 genes set forth in FIG. 4, FIG. 5, FIG. 9, or Table 5, or a combination thereof as compared to a reference. Methods for measuring gene expression include techniques for detecting mRNA expression such as PCR, RNA-Seq, and microarray techniques. Gene expression can also be measured by immunological methods such as immunohistochemical staining of tissue sections or cells in culture. Gene expression may also be measured by detecting protein expression. Protein expression levels can be measured, e.g., using immunoassays such as western blotting, dot blotting, ELISA, immunoPCR, and the like, or with proteomic detection methods which detect many proteins simultaneously, multidimensional gel electrophoresis, mass spectrometry based methods, or surface plasmon resonance techniques.

In some embodiments, the reference can be the gene expression profile of the at least 10 genes set forth in FIG. 4, FIG. 5, FIG. 9, or Table 5, or a combination thereof of the subject prior to the treatment.

In some embodiments, the reference can be the gene expression profile of the at least 10 genes set forth in FIG. 4, FIG. 5, FIG. 9, or Table 5, or a combination of a subject or a population of subjects with longevity.

In another aspect, an assay is provided herein for identifying a treatment that can modulate lifespan, the assay comprising: (a) administering a treatment to a cell, cell line, or mammal; (b) measuring, in the cell, cell line or a biological sample obtained from the mammal, a gene expression profile of at least 10 genes set forth in FIG. 4, FIG. 5, FIG. 9, or Table 5, or a combination thereof; (c) comparing the gene expression profile of the at least 10 genes with a reference longevity signature, wherein if the gene expression profile is at least 75% similar to the reference longevity signature, the treatment is predicted to increase lifespan, and wherein if the gene expression profile is less than 75% similar to the reference longevity signature, the treatment is predicted to have no effect on lifespan or decrease lifespan. As used herein, the term "gene expression profile" refers to a set of values and/or qualitative descriptors, each value and/or descriptor representing the level of expression (e.g., mRNA or protein) of a particular gene. The gene expression profile can be presented in any format, such as a matrix or a heatmap. See, for example, U.S. Pat. Nos. 6,040,138, 5,800,992, 6,020135, 6,344,316, and 6,033,860, which are hereby incorporated by reference in their entireties.

In some embodiments, the gene expression profile is determined by contacting the cell, cell line, biological sample obtained from the mammal, or molecules extracted or amplified from the cell or sample to a nucleic acid array. In another embodiment, the gene expression profile is determined by contacting the cell, cell line, biological sample obtained from the mammal, or molecules extracted or amplified from the cell or sample to a protein array. In still another embodiment, the gene expression profile is determined by mass spectroscopy. Arrays comprise capture probes for detecting the differentially expressed genes. By "array" is intended a solid support or substrate with peptide or nucleic acid probes attached to said support or substrate. Arrays typically comprise a plurality of different nucleic acid or peptide capture probes that are coupled to a surface of a substrate in different, known locations. These arrays, also described as "microarrays" or colloquially "chips" have been generally described in the art, for example, in U.S. Pat. Nos. 5,143,854, 5,445,934, 5,744,305, 5,677,195, 6,040,193, 5,424,186, 6,329,143, and 6,309,831 and Fodor et al. *Science* 251:767-77 (1991), each of which is incorporated by reference in its entirety. These arrays may generally be produced using mechanical synthesis methods or light directed synthesis methods that incorporate a combination of photolithographic methods and solid phase synthesis methods.

The comparison of gene expression profiles can be done by a number of means known in the art. Methods for comparing gene expression profiles can be found, for example, in Severgnini et al., *Anal. Biochem.* 2006, 353, 43-56; Zheng-Bradley et al., *Genome Biology* 2010, 11, R124; Holloway et al. (2002) *Nature Genetics Suppl.* 32:481-89; Churchill (2002) *Nature Genetics Suppl.* 32:490-95; Quackenbush (2002) *Nature Genetics Suppl.* 32: 496-501; Slonim (2002) *Nature Genetics Suppl.* 32:502-08; and Chuaqui et al. (2002) *Nature Genetics Suppl.* 32:509-514; each of which is herein incorporated by reference in its entirety.

In some embodiments, wherein if the gene expression profile is at least 80%, at least 85%, or at least 90% similar to the reference longevity signature, the treatment is predicted to increase lifespan, and wherein if the gene expression profile is less than 80%, less than 85%, or less than 90% similar to the reference longevity signature, the treatment is predicted to have no effect on lifespan or decrease lifespan.

In some embodiments, step (b) comprises measuring the gene expression profile of at least 20 genes, at least 100 genes, at least 500 genes, or at least 1000 genes set forth in FIG. 4, FIG. 5, FIG. 9, or Table 5, or a combination thereof.

In some embodiments, the reference longevity signature can be a gene expression profile of the at least 10 genes of at least one mammal having a long lifespan relative to the test mammal. In some embodiments, the reference longevity signature can be a gene expression profile of the at least 10 genes of a cohort of mammals having a long lifespan relative to the test mammal. In some embodiments, the reference longevity signature can be the gene expression profile of the at least 10 genes in FIG. 4, FIG. 5, FIG. 9, or Table 5, or a combination thereof of the mammal prior to the treatment.

In yet another aspect, an assay is provided herein for identifying a treatment that can modulate lifespan, the assay comprising: (a) administering a treatment to a cell, cell line, or mammal; (b) measuring, in the cell, cell line or a biological sample obtained from the mammal, a gene expression profile of at least 10 genes set forth in FIG. 4, FIG. 5, FIG. 9, or Table 5, or a combination thereof; (c) determining a longevity score as a function of the measurement in step (b); and (d) comparing the longevity score with a reference score determined from a reference longevity signature associated with the at least 10 genes, wherein if the longevity score is at or above the reference score, the treatment is predicted to increase lifespan, and wherein if the longevity score is below the reference, the treatment is predicted to have no effect on lifespan or decrease lifespan.

Several methods can be used to calculate the longevity score. In some embodiments, the longevity score can be determined by summing up the number of upregulated genes that should be upregulated and the number of downregulated genes that should be downregulated according to the gene expression signatures associated with longevity according to FIG. 4, FIG. 5, FIG. 9, or Table 5, or a combination thereof. In some embodiments, the longevity score is weighted depending on the relative importance of each gene to longevity. For example, a weighted sum can be calculated using the following formula: Sum=$\Sigma_{i=1}^n w_i$, where $w_i$ is the weight for gene i. The reference scores can be determined in similar manners. It should be noted that the longevity score should be calculated in the same manner as the reference score.

In another aspect, an assay is provided herein for identifying a treatment that can modulate lifespan, the assay comprising: (a) administering a treatment to a cell, cell line, or mammal; (b) measuring, in the cell, cell line or a biological sample obtained from the mammal, expression levels of at least 10 of the upregulated genes set forth in FIG. 4, FIG. 5, FIG. 9, or Table 5, or a combination thereof and at least 10 of the downregulated genes set forth in FIG. 4, FIG. 5, FIG. 9, or Table 5, or a combination thereof; (c) determining a gene expression ratio of the at least 10 of the upregulated genes set forth in FIG. 4, FIG. 5, FIG. 9, or Table 5, or a combination thereof and the at least 10 of the downregulated genes set forth in FIG. 4, FIG. 5, FIG. 9, or Table 5, or a combination thereof; and (d) comparing the gene expression ratio with a reference ratio determined for a reference gene expression profile associated with a longevity signature. Similar to the longevity score, the gene expression ratio provides another useful metric for determining whether a treatment can modulate lifespan. In some embodiments, the gene expression ratio is the number of upregulated genes that should be upregulated over the number of downregulated genes that should be downregulated according to FIG. 4, FIG. 5, FIG. 9, or Table 5. In some embodiments, the gene expression ratio takes into account the relative importance of each gene to longevity.

For the assays and methods described herein, a skilled artisan can readily appreciate that the administering step can be optional. A skilled artisan will also realize that if a smaller set of genes does not yield adequate information, a physician can increase the number of genes to be measured, for example, from 10 genes to 20 genes, 30 genes, 50 genes, 100 genes or more.

Genes can be categorized into groups based on the biological processes and pathways involved. These biological processes and pathways include, but are not limited to, regulation of immune response, regulation of cytokine production, regulation of defense response, base-excision repair, integrin-mediated signaling pathway, platelet alpha granule, platelet degranulation, response to calcium ion, superoxide metabolic process, GDP-mannose metabolic process, regulation of protein kinase activity, regulation of protein processing, cytoskeleton, stress fiber, actomyosin, axonogenesis, axon guidance, neuron differentiation, synaptic transmission, synaptic transmission (glutamatergic, regulation of neurotransmitter levels, metal ion transport, store-operated calcium channel activity, inositol 1,4,5-trisphosphate binding, gated channel activity, divalent inorganic cation transport, calcium ion transport, acetyl-CoA biosynthetic process, fatty acid beta-oxidation, lipid oxidation, lipid modification, glycerol ether metabolic process, acylglycerol metabolic process, peroxisome targeting sequence binding, glycerolipid metabolic process, cysteine metabolic process, peroxisomal membrane, carboxylic acid biosynthetic process, carboxylic acid catabolic process, tricarboxylic acid cycle, mitochondrial membrane, lipid catabolic process, cellular amino acid catabolic process, lysine catabolic process, respiratory electron transport chain, ubiquitin ligase complex, coenzyme biosynthetic process, fatty acid metabolic process, and cellular amine metabolic process. These biological processes and pathways, in turn, affect various life histories including, but not limited to, birth weight, time to maturity, weaning time, gestation period, adult weight, time to maturity, growth rate, oxygen consumption, and maximum life span.

The inventor has also discovered an intimate relationship between life history variation and central energy metabolism. Pathways associated with central energy metabolism include, but are not limited to, pyruvate metabolism, carbohydrate degradation pathways, catabolism of tryptophan, lysine and valine, oxidation and biosynthesis of fatty acids, Ppar, peroxisome, Ampk, growth hormone signaling and others. And thus while performing the assays and methods described herein, a physician can select genes for measurement based on the biological processes and pathways involved and any combination thereof, or measure the metabolite levels.

In some embodiments, the methods and assays described herein further comprise measuring a level of at least one metabolite. Metabolite levels can be measured by one or more method(s) selected from spectroscopy methods such as NMR (nuclear magnetic resonance), or mass spectroscopy (MS); SELDI (-TOF), MALDI (-TOF), a 1-D gel-based analysis, a 2-D gel-based analysis, liquid chromatography (e.g. UPLC-MS, high pressure liquid chromatography (HPLC) or low pressure liquid chromatography (LPLC)), thin-layer chromatography, and LC-MS-based techniques.

Administration of Treatment

In some embodiments of the methods and assays described herein, the treatment comprises administration of an agent, a lifestyle change, a change in disease status, or a combination thereof.

In some embodiments, the agent comprises a small molecule, a peptide, a peptidomimetic, an RNA interference molecule, a polypeptide, an antibody, a protein or a fragment thereof, a nucleic acid, an antisense molecule, a hormone, a transcription factor, an ion, a carbohydrate, an aptamer, or a gene therapy. Without wishing to be bound by theory, the general principal of gene therapy is to introduce a polynucleotide into a target cell in a patient, and where it is transcribed into protein. See, generally, for example, U.S. Pat. No. 5,399,346, which is incorporated herein by reference. In these embodiments, the agent can be administered in a single dose or multiple doses over a period of time (e.g., 2, 3, 4, 5, 6, 7, or 8 doses).

In some embodiments, the agent is a geroprotector. A geroprotector is a therapeutic that aims to affect the root cause of aging and age-related diseases, and thus prolong the life span of animals. Non-limiting examples of geroprotectors include melatonin, carnosine, and metformin.

Libraries of test compounds to be screened are available. These libraries are optionally random or targeted. Targeted libraries include those designed using any form of a rational design technique that selects scaffolds or building blocks to generate combinatorial libraries. These techniques include a number of methods for the design and combinatorial synthesis of target-focused libraries, including morphing with bioisosteric transformations, analysis of target-specific privileged structures, and the like. Random libraries exist for a variety of basic chemical scaffolds. In either case, many thousands of scaffolds and building blocks for chemical libraries are available, including those with polypeptide, nucleic acid, carbohydrate, and other backbones. Commercially available libraries and library design services include those offered by Chemical Diversity (San Diego, Calif.), Affymetrix (Santa Clara, Calif.), Sigma (St. Louis Mo.), ChemBridge Research Laboratories (San Diego, Calif.), TimTec (Newark, Del.), Nuevolution A/S (Copenhagen, Denmark) and many others.

In some embodiments, the lifestyle change comprises a change in exercise status, a dietary change, a change in smoking status, a change in alcohol or substance use, a change in stress levels, a change in environment, a change in occupation, or a combination thereof.

Biological Samples

The terms "sample" or "biological sample" as used herein denote a sample taken or isolated from a biological organism, e.g., an animal or human. Exemplary biological samples include, but are not limited to, a biofluid sample; a body fluid sample, blood (including whole blood); serum; plasma; urine; saliva; a biopsy and/or tissue sample etc. The term also includes a mixture of the above-mentioned samples. The term "sample" also includes untreated or pretreated (or pre-processed) biological samples. In some embodiments, a sample can comprise one or more cells from the subject.

The sample can be obtained by removing a sample from a subject, but can also be accomplished by using previously isolated samples (e.g. isolated at a prior time point and isolated by the same or another person). In addition, the sample can be freshly collected or a previously collected sample.

In some embodiments, the sample can be an untreated sample. As used herein, the phrase "untreated sample" refers to a sample that has not had any prior sample pre-treatment except for dilution and/or suspension in a solution. In some embodiments, a sample can be a pre-processed sample, for example, supernatant or filtrate resulting from a treatment selected from the group consisting of centrifugation, filtration, thawing, purification, and any combinations thereof. In some embodiments, the sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing.

In some embodiments, the sample can be a frozen sample, e.g., a frozen tissue. The frozen sample can be thawed before employing methods, assays and systems described herein. After thawing, a frozen sample can be centrifuged before being subjected to methods, assays and systems described herein. In some embodiments, the sample is a clarified sample, for example, by centrifugation and collection of a supernatant comprising the clarified sample.

In some embodiments, the biological sample comprises a tissue from an organ. Examples of organs include, but are not limited to, liver, kidney, heart, intestines, lung, pancreas, prostate, and brain.

Subjects

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein.

Preferably, the subject is a mammal. The mammal can be a human, non-human primate, mouse, rat, dog, cat, horse, or cow, but are not limited to these examples.

Computer Systems

In some embodiments of the assays and/or methods described herein, the assay/method comprises or consists essentially of a system for determining (e.g. transforming and measuring) the gene expression profiles as described herein and comparing them to a reference. The comparison can be performed in a comparison system, which can be a computer implemented system.

In one embodiment, provided herein is a system comprising: (a) at least one memory containing at least one computer program adapted to control the operation of the computer system to implement a method that includes (i) a determination module configured to measure the gene expression profile in a cell, cell line or sample obtained from a subject; (ii) a storage module configured to store output data from the determination module; (iii) a computing module adapted to identify from the output data whether the measured gene expression profile differs from a reference, and to provide a retrieved content; (iv) a display module for displaying for retrieved content (e.g., whether the treatment can increase lifespan, or whether the treatment can affect the health profile of the subject); and (v) at least one processor for executing the computer program. In some embodiments, the determination module further comprises determining a longevity score as a function of the measurement. In some embodiments, the determination module further comprises determining a gene expression ratio.

Embodiments can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing. Computer-readable storage medium do not include a signal.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J #, Visual Basic, C, C #, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the technology discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the technology described herein. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments can include at minimum a determination module, a storage module, a computing module, and a display module. The functional modules can be executed on one, or multiple, computers, or by using one, or multiple, computer networks.

The determination module has computer executable instructions to provide e.g., levels of expression products etc in computer readable form.

The determination module can comprise any system for detecting a signal resulting from the detection of gene expression. In some embodiments, such systems can include an instrument, e.g., a microarray. In some embodiments, such systems can include an instrument, e.g., the Cell Biosciences NANOPRO 1000™ System (Protein Simple; Santa Clara, Calif.) for quantitative measurement of proteins.

The information determined in the determination system can be read by the storage module. As used herein the "storage module" is intended to include any suitable computing or processing apparatus or other device configured or adapted for storing data or information. Examples of electronic apparatus suitable for use with the technology described herein include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, patient name, and gene expression profile. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In one embodiment of any of the systems described herein, the storage module stores the output data from the determination module. In additional embodiments, the storage module stores the reference information such as a reference longevity signature. In some embodiments, the storage module stores the information such as the gene expression profile measured from the same subject in earlier time points.

The "computing module" can use a variety of available software programs and formats for computing the gene expression levels and/or generating gene expression profiles. Such algorithms are well established in the art. A skilled artisan is readily able to determine the appropriate algorithms based on the size and quality of the sample and type of data. The data analysis can be implemented in the computing module. Specifically, depending on the methods or assays, the computing module can further comprise a comparison module to (a) compare the gene expression profile with a reference longevity signature, (b) compare the longevity score with a reference score determined from a reference longevity signature, or (c) compare the gene expression ratio with a reference ratio determined for a reference gene expression profile associated with a longevity signature. In various embodiments, the comparison module can be configured using existing commercially-available or freely-available software for comparison purpose, and may be optimized for particular data comparisons that are conducted.

The computing and/or comparison module, or any other module, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware, as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment, users can directly access data (via Hypertext links for example) residing on Internet databases using a HTML interface provided by Web browsers and Web servers.

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be the gene expression levels in the sample obtained from a subject. In some embodiments, the content displayed on the display module can be the gene expression profile in the sample obtained from a subject. In certain embodiments, the content displayed on the display module can indicate whether the treatment can increase lifespan or affect the health profile of the subject.

In one embodiment, the content based on the computing and/or comparison result is displayed on a computer monitor. In one embodiment, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the technology relating to determining the gene expression profiles, and therefore are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

Applications

The methods, assays, and systems described herein can be useful in a number of areas, including the discovery and validation of new targets for reducing rate of aging, extending lifespan, reducing incidence and delaying onset of disease and improving overall health of aging populations. Furthermore, the invention can facilitate the discovery and development of drugs, biologicals and treatment regimens based on the above that favorably intervene in the aging process. For example, the gene expression signatures described herein can be used to choose target gene products in a therapeutic protocol, to elaborate the biological function of the target gene product in the aging process, and to identify compounds that alleviate deterioration associated with aging by modulating the activity of target gene products. For example, several compounds that shift gene expression in the direction of longevity have been identified or validated using the assays or methods described herein (Table 6).

Evaluation of Test Compounds

Embodiments include carrying out primary compound screens for lifespan extension in vitro using molecular or cell-based assays and/or in vivo using simple model organisms with automated, high throughput, high capacity screens. The collection of genes of the invention can replace measuring death as an assay endpoint for the in vivo screens, and therefore speed these screens and reduce costs. Gene expression profiling can be used to assess efficacy, mechanism of action, potential toxicity and pharmacogenetic features of candidate lifespan extending compounds which emerge from the screens. Test compounds can be evaluated using animal models.

High throughput methods of screening, e.g., drug screening, can be used in identifying compounds that can modulate lifespan or affect a health profile of a subject. Generally in these methods, a sample (e.g., a cell-free assay mixture, a cell, or a non-human animal) is contacted with or administered a test compound; typically, one or more of a panel or library of compounds is contacted or administered to each of a plurality of samples. Modulation of a relevant parameter (e.g., expression, activity, or lifespan of the organism) by the test compounds is detected, thereby identifying one or more compound as a modulator or potential modulator. The assays, methods, and systems of the present invention can be useful in performing high-throughput (e.g., greater than 1,000 compounds/day) and even ultra-high throughput (e.g., greater than 10,000 compounds/day) screening of chemical libraries, e.g., searching for lifespan/health profile modulators. These experiments may be carried out in parallel by a providing a large number of samples (e.g., reaction mixtures, cell suspensions, or organisms) in separate receptacles, typically in a multi-well or similar format, e.g., 96 well, 324 well or 1536 well plates. Different test compounds (library members) are added to separate wells, and the effect of the compound on the sample is ascertained, e.g., via lifespan determination, detection of expression, or activity. These parallel assays are generally carried out using specialized equipment to enable simultaneous processing of large numbers of samples, i.e., fluid handling by robotic pipettor systems and detection in multiplexed systems.

Validation of Life Style Changes

Life style changes are long believed to be able to affect lifespan, but quantitative data in support of this belief is scarce. The methods, assays, and systems of the invention can be used to study and quantify the effect of life style changes (e.g., a change in exercise status, a dietary change, a change in smoking status, a change in alcohol or substance use, a change in stress levels, a change in environment, a change in occupation, or a combination thereof) on lifespan or health profiles, thus leading to the validation of the effectiveness of these changes.

The methods, assays, and systems of the invention can also permit a person to monitor whether his/her life style change is leading towards an increased lifespan or improved health profile.

Diagnostics and Patient Care

The methods, assays, and systems described herein can also be used for diagnostic purposes, e.g., patient care. For example, the collection of genes described herein can be used to evaluate the health profile of a subject. The subject can be a healthy or affect subject, e.g., an adult patient or a patient undergoing treatment. For example, a method comprises measuring, in a sample obtained from the subject, the gene expression profile of at least 10 genes of FIG. 4, FIG. 5, FIG. 9, or Table 5. Optionally, the method further comprises comparing the measured gene expression profile with a reference longevity signature.

A physician or caregiver can also use the methods, assays, and systems described herein to assess whether a treatment administered to a subject is shifting the subject towards an increased lifespan or improved health profile.

The methods, assays, and systems of the invention can also be used to aid the treatment of age-related diseases. As used herein, the term "age related disease" refers to diseases, conditions and symptoms that are predominantly found or manifested in older animals, e.g., in humans, people over 50 or more preferably people over 65. For any animal, age-related diseases would manifest after maturation, e.g., post-development. The age at which maturity is reached is different depending on the animal and for each animal such time would be well known to those of skill in the art. Age-related diseases include certain cancers, cardiovascular disease, atherosclerosis, hypertension, diabetes (e.g., type 2), osteoporosis, depression, neurodegenerative disease, Alzheimer's, Parkinson's, glaucoma, certain immune system defects, kidney failure, liver steatosis, and other conditions well known to those of skill in the art.

It should be understood that this invention is not limited to the particular methodology, protocols, and reagents, etc., disclosed herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are disclosed herein.

Some embodiments of the invention are listed in the following numbered paragraphs:

1. A collection of gene expression signatures as set forth in FIG. 4, FIG. 5, FIG. 9, or Table 5, or a combination thereof that are upregulated.
2. A collection of gene expression signatures as set forth in FIG. 4, FIG. 5, FIG. 9, or Table 5, or a combination thereof that are downregulated.
3. A method of screening a treatment that affects a health profile of a subject, the method comprising:
   (a) administering the treatment to the subject or a cell obtained from the subject; and
   (b) measuring, in a sample obtained from the subject or the cell, an effect of the treatment on the expression of at least 10 genes of paragraph 1, 2, or a combination thereof as compared to a reference.
4. The method of paragraph 3, wherein the treatment comprises administration of an agent, a lifestyle change, a change in disease status, or a combination thereof
5. The method of paragraph 4, wherein the agent comprises a small molecule, a peptide, a peptidomimetic, an RNA interference molecule, an antibody, an aptamer, or a gene therapy.
6. The method of paragraph 5, wherein the agent is a geroprotector.
7. The method of paragraph 4, wherein the lifestyle change comprises a change in exercise status, a dietary change, a change in smoking status, a change in alcohol or substance use, a change in stress levels, or a combination thereof.
8. The method of paragraph 3, wherein the subject is a mammal.
9. The method of paragraph 8, wherein the mammal is a human.
10. An assay for identifying a treatment that can modulate lifespan, the assay comprising:
    (a) administering a treatment to a cell, cell line, or mammal;
    (b) measuring, in the cell, cell line or a biological sample obtained from the mammal, a gene expression profile of at least 10 genes of paragraph 1, 2, or a combination thereof;
    (c) comparing the gene expression profile of the at least 10 genes with a reference longevity signature, wherein if the gene expression profile is at least 75% similar to the reference longevity signature, the treatment is predicted to increase lifespan, and wherein if the gene expression profile is less than 75% similar to the reference longevity signature, the treatment is predicted to have no effect on lifespan or decrease lifespan.
11. The assay of paragraph 10, wherein the treatment comprises administration of an agent, a lifestyle change, a change in disease status, or a combination thereof.
12. The assay of paragraph 11, wherein the agent comprises a small molecule, a peptide, a peptidomimetic, an RNA interference molecule, an antibody, an aptamer, or a gene therapy.
13. The assay of paragraph 12, wherein the agent is a geroprotector.
14. The assay of paragraph 11, wherein the lifestyle change comprises a change in exercise status, a dietary change, a change in smoking status, a change in alcohol or substance use, a change in stress levels, or a combination thereof.
15. The assay of paragraph 10, wherein the reference longevity signature comprises a gene expression profile of at least one mammal having a long lifespan.
16. The assay of paragraph 10, wherein step (b) comprises measuring the gene expression profile of at least 20 genes, at least 100 genes, at least 500 genes, or at least 1000 genes of paragraph 1, 2, or a combination thereof.
17. The assay of paragraph 10, wherein the biological sample comprises whole blood, plasma, serum, liver, kidney or brain tissue.
18. The assay of paragraph 10, wherein the mammal is a human.
19. An assay for identifying a treatment that can modulate lifespan, the assay comprising:
    (a) administering a treatment to a cell, cell line, or mammal;
    (b) measuring, in the cell, cell line or a biological sample obtained from the mammal, a gene expression profile of at least 10 genes of paragraph 1, 2, or a combination thereof;
    (c) determining a longevity score as a function of the measurement in step (b); and
    (d) comparing the longevity score with a reference score determined from a reference longevity signature associated with the at least 10 genes, wherein if the longevity score is at or above the reference score, the treatment is predicted to increase lifespan, and wherein if the longevity score is below the reference, the treatment is predicted to have no effect on lifespan or decrease lifespan.
20. The assay of paragraph 19, wherein the treatment comprises administration of an agent, a lifestyle change, a change in disease status, or a combination thereof.
21. The assay of paragraph 20, wherein the agent comprises a small molecule, a peptide, a peptidomimetic, an RNA interference molecule, an antibody, an aptamer, or a gene therapy.
22. The assay of paragraph 21, wherein the agent is a geroprotector.
23. The assay of paragraph 20, wherein the lifestyle change comprises a change in exercise status, a dietary change, a change in smoking status, a change in alcohol or substance use, a change in stress levels, or a combination thereof.
24. The assay of paragraph 19, wherein the reference longevity signature comprises a gene expression profile of at least one mammal having a long lifespan.
25. The assay of paragraph 19, wherein step (b) comprises measuring the gene expression profile of at least 20 genes, at least 100 genes, at least 500 genes, or at least 1000 genes of paragraph 1, 2, or a combination thereof.
26. The assay of paragraph 19, wherein the biological sample comprises whole blood, plasma, serum, liver, kidney or brain tissue.
27. The assay of paragraph 19, wherein the mammal is a human.
28. An assay for identifying a treatment that can modulate lifespan, the assay comprising:
    (a) administering a treatment to a cell, cell line, or mammal;
    (b) measuring, in the cell, cell line or a biological sample obtained from the mammal, expression levels of at least 10 genes of paragraph 1 and at least 10 genes of paragraph 2;

(c) determining a gene expression ratio of the at least 10 genes of paragraph 1 and the at least 10 genes of paragraph 2; and
(d) comparing the gene expression ratio with a reference ratio determined for a reference gene expression profile associated with a longevity signature.
29. An assay for determining an effect of a treatment on a health profile of a subject, the assay comprising:
(a) administering the treatment to the subject or a cell obtained from the subject; and
(b) measuring, in a sample obtained from the subject or the cell, the effect of the treatment on the expression of at least 10 genes of paragraph 1, 2, or a combination thereof as compared to a reference.
30. The method of paragraph 3, wherein the reference is a gene expression profile of the at least 10 genes of paragraph 1, 2, or a combination thereof of the subject prior to the treatment.
31. The assay of paragraph 29, wherein the reference is a gene expression profile of the at least 10 genes of paragraph 1, 2, or a combination thereof of the subject prior to the treatment.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "antibody" herein is used in the broadest sense and specifically covers monoclonal antibodies, polyclonal antibodies, multispecific antibodies (e.g. bispecific antibodies) formed from at least two intact antibodies, chimeric antibodies, humanized antibodies, and antibody fragments (whether produced, e.g., by the modification of whole antibodies or synthesized de novo using recombinant DNA methodologies) so long as they exhibit a desired biological activity. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. An intact antibody is one comprising heavy- and light-variable domains as well as an Fc region. Antibody fragments comprise a portion of an intact antibody, preferably comprising the antigen-binding region thereof. Examples of antibody fragments include Fab, Fab', $F(ab)_2$, and Fv fragments, diabodies, linear antibodies, single-chain antibody molecules, and multispecific antibodies formed from antibody fragments. Antibody fragments are optionally produced using enzymatic digestion of intact antibodies or synthesized chemically or by recombinant DNA methods. The subunit structures and three-dimensional configurations of different classes and fragments of immunoglobulins are well known and the term antibody as used herein includes all configurations, fragments, and classes. Methods of making and using antibodies are well known to those of skill in the art.

The term "gene" is used broadly to refer to any nucleic acid associated with a biological function. Genes typically include coding sequences and/or the regulatory sequences required for expression of coding sequences. The term "gene" applies to a specific genomic sequence, as well as to a cDNA or an mRNA encoded by that genomic sequence. Genes also include non-expressed nucleic acid segments that, for example, form recognition sequences for other proteins. Non-expressed regulatory sequences include "promoters" and "enhancers", to which regulatory proteins such as transcription factors bind, resulting in transcription of adjacent or nearby sequences. In some cases, a gene is heritable. In some aspects, genes comprise coding sequences (e.g., an "open reading frame" or "coding region") necessary for the production of a polypeptide, while in other aspects, genes do not encode a polypeptide.

Examples of genes that do not encode polypeptides include ribosomal RNA genes (rRNA) and transfer RNA (tRNA) genes. Genes of use in the present invention include, but are not limited to, those set forth in FIG. 4, FIG. 5, FIG. 9 or Table 5.

"Expression" of a gene or expression of a nucleic acid means transcription of DNA into RNA (optionally including modification of the RNA, e.g., splicing), translation of RNA into a polypeptide (possibly including subsequent modification, e.g., posttranslational modification), or both transcription and translation.

As used herein, an "expression level" or "level of expression" is a value that corresponds to a measurement of the abundance of a gene expression product. Such values may include measurements of RNA levels or protein abundance. Thus, an expression level can be a value that reflects the transcriptional state or the translation state of a gene. The transcriptional state of a sample includes the identities and abundance of the RNA species, especially mRNAs present in the sample. The transcriptional state can be conveniently determined by measuring transcript abundance by any of several existing gene expression technologies. Translational state includes the identities and abundance of the constituent protein species in the sample. As is known to those of skill in the art, the transcriptional state and translational state are related.

As used herein, "upregulated", "upregulating", or "upregulation" means an increase in the amount or activity of a gene or gene product relative to a baseline or control state, through any mechanism including, but not limited to increased transcription, translation and/or increased stability of the transcript or protein product.

As used herein, "downregulated", "downregulating", or "downregulation" refers to detecting a decrease in the amount or activity of a gene or gene product relative to a baseline or control state, through any mechanism including, but not limited to decreased transcription, translation and/or decreased stability of the transcript or protein product.

The terms "decrease", "reduced", "reduction" are all used herein to mean a decrease by a statistically significant amount. In some embodiments, "reduce," "reduction" or "decrease" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more.

The terms "increased", "increase" or "enhance" are all used herein to generally mean an increase by a staticallysignificant amount; for the avoidance of any doubt, the terms "increased", "increase" or "enhance" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "software" is used interchangeably herein with "program" and refers to prescribed rules to operate a computer. Examples of software include: software; code segments; instructions; computer programs; and programmed logic.

The term a "computer system" may refer to a system having a computer, where the computer comprises a computer-readable medium embodying software to operate the computer.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those disclosed herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Until recently, technical difficulties associated with simultaneously measuring the expression of a large number of genes in diverse species were a bottleneck for comparative studies of gene expression. The rise of RNA-seq technologies allowed overcoming limitations in genome-wide quantitative analysis of transcript levels among species. In this study, 143 RNA-seq gene expression profiles for liver, kidney and brain were prepared and comparative gene expression analyses of 33 mammalian species were carried out. By considering gene expression as a quantitative character, evolution of gene expression was examined across quantitative whole-organism life history traits. Without wishing to be bound by theory, offered herein is a concept of parallel evolution of mammalian life histories and gene expression over evolutionary timescale and identify the processes involved, providing insights into the specific processes altered as species change their lifespan.

Example 1: Study Results

Analysis of Gene Expression to Elucidate Lifespan and Other Life History Strategies An analysis of gene expression divergence was carried out on 33 species of terrestrial mammals of young adult age belonging to Euungulata (n=4), Carnivora (n=4), Chiroptera (n=2), Didelphimorphia (n=1), Diprotodoncia (n=1), Erinaceomorpha (n=1), Lagomorpha (n=1), Monotremata (n=1), Primate (n=8), Rodentia (n=9) and Soricomorpha (n=1) lineages (Table 3).

TABLE 3

Classification and sampling sources of 33 mammals.

| Class | Order | Family | Genus | Species | Common name | NCBI id | Abbreviation | Liver | Kidney | Brain | Source[1] |
|---|---|---|---|---|---|---|---|---|---|---|---|
| Mammalia | Euungulata | Bovidae | *Bos* | *taurus* | Domestic cattle | 9913 | bta | 2 | 2 | 2 | Study |
| Mammalia | Euungulata | Bovidae | *Capra* | *hircus* | Domestic goat | 9925 | chi | 2 | 2 | 2 | Study |
| Mammalia | Euungulata | Suidae | *Sus* | *scrofa* | Domestic boar | 9825 | ssc | 2 | 2 | 2 | Study |
| Mammalia | Carnivora | Canidae | *Canis* | *familiaris* | Domestic dog | 9615 | caf | 2 | 2 | 2 | Study |
| Mammalia | Carnivora | Felidae | *Felis* | *catus* | Domestic cat | 9685 | fca | 3 | 3 | 3 | Study |
| Mammalia | Carnivora | Mustelidae | *Meles* | *meles* | Asian badger | 9662 | mle | 2 | 2 | 2 | Study |
| Mammalia | Carnivora | Ursidae | *Ursus* | *americanus* | American black bear | 9643 | uam | 2 | 2 | 2 | Study |
| Mammalia | Chiroptera | Vespertilionidae | *Murina* | *leucogaster* | Greater tube-nosed bat | 685731 | mhi | 2 | 1 | 2 | Study |
| Mammalia | Chiroptera | Molossidae | *Tadarida* | *brasiliensis* | Brazilian free-tailed bat | 9438 | tbr | 3 | — | — | Study |
| Mammalia | Didelphimorphia | Didelphidae | *Monodelphis* | *domestica* | Short-tailed opossum | 13616 | mod | 2 | 2 | 3 | GSE30352 |
| Mammalia | Diprotodontia | Petauridae | *Petaurus* | *breviceps* | Sugar glider | 34899 | pbr |  | 2 | 2 | Study |
| Mammalia | Erinaceomorpha | Erinaceidae | *Erinaceus* | *europaeus* | Western European hedgehog | 9365 | eeu | 2 | 2 | 2 | Study |
| Mammalia | Lagomorpha | Leporidae | *Oryctolagus* | *cuniculus* | Old World rabbit | 9986 | ocu | 2 | 2 | 2 | Study |
| Mammalia | Monotremata | Ornithorhynchidae | *Ornithorhynchus* | *anatinus* | Duck-billed platypus | 9258 | oan | 4 | 3 | 4 | GSE30352 |
| Mammalia | Euungulata | Equidae | *Equus* | *caballus* | Horse | 9796 | eca | 3 | 3 | 2 | Study |
| Mammalia | Primates | Cercopithecidae | *Chlorocebus* | *aethiops* | Vervet | 9534 | cae | 1 | 1 | 1 | Study |
| Mammalia | Primates | Hominidae | *Gorilla* | *gorilla* | Gorilla | 9593 | ggo | 2 | 2 | 2 | GSE30352 |
| Mammalia | Primates | Hominidae | *Homo* | *sapiens* | Human | 9606 | hsa | 3 | 3 | 5 | GSE30352 |
| Mammalia | Primates | Cercopithecidae | *Macaca* | *fascicularis* | Long-tailed macaque | 9541 | mfa | 1 | 1 | 1 | GSE29629 |

TABLE 3-continued

Classification and sampling sources of 33 mammals.

| Class | Order | Family | Genus | Species | Common name | NCBI id | Abbreviation | Liver | Kidney | Brain | Source[1] |
|---|---|---|---|---|---|---|---|---|---|---|---|
| Mammalia | Primates | Cercopithecidae | *Macaca* | *mulatta* | Rhesus monkey | 9544 | mmu | 3 | 2 | 3 | GSE30352 |
| Mammalia | Primates | Hominidae | *Pan* | *paniscus* | Pygmy chimpanzee or bonono | 9597 | ppa | 2 | 2 | 2 | GSE30352 |
| Mammalia | Primates | Hominidae | *Pongo* | *pygmaeus* | Orangutan | 9600 | ppy | 2 | 2 | 2 | GSE30352 |
| Mammalia | Primates | Hominidae | *Pan* | *troglodytes* | Chimpanzee | 9598 | ptr | 2 | 2 | 6 | GSE30352 |
| Mammalia | Rodentia | Muridae | *Acomys* | *cahirinus* | Spiny mouse | 10068 | aca | 3 | — | — | Study |
| Mammalia | Rodentia | Caviidae | *Cavia* | *porcellus* | Guinea pig | 10141 | cpo | 3 | 3 | 3 | Study |
| Mammalia | Rodentia | Bathyergidae | *Heterocephalus* | *glaber* | Naked mole-rat | 10181 | hgl | 2 | 2 | 2 | GSE30337 |
| Mammalia | Rodentia | Muridae | *Mesocricetus* | *auratus* | Golden hamster | 10036 | mau | 3 | 3 | 3 | Study |
| Mammalia | Rodentia | Muridae | *Meriones* | *unguiculatus* | Mongolian gerbil | 10047 | mun | 3 | 3 | 3 | Study |
| Mammalia | Rodentia | Muridae | *Mus* | *musculus* | House mouse | 10090 | mus | 3 | 3 | 3 | Study |
| Mammalia | Rodentia | Muridae | *Peromyscus* | *leucopus* | White-footed mouse | 10041 | ple | 2 | 2 | 2 | Study |
| Mammalia | Rodentia | Muridae | *Rattus* | *norvegicus* | Norway rat | 10116 | mo | 3 | 3 | 3 | Study |
| Mammalia | Rodentia | Sciuridae | *Tamias* | *sibiricus* | Siberian chipmunk | 64680 | tsi | — | 2 | 2 | Study |
| Mammalia | Soricomorpha | Soricidae | *Suncus* | *murinus* | House shrew | 9378 | smu | 3 | — | — | Study |

[1]RNA-seq libraries for Primates, Monotremata, and Didelphimorphia species were downloaded from Gene Expression Omnibus database (www.ncbi.nlm.nih.gov/geo).

Figure 1A:
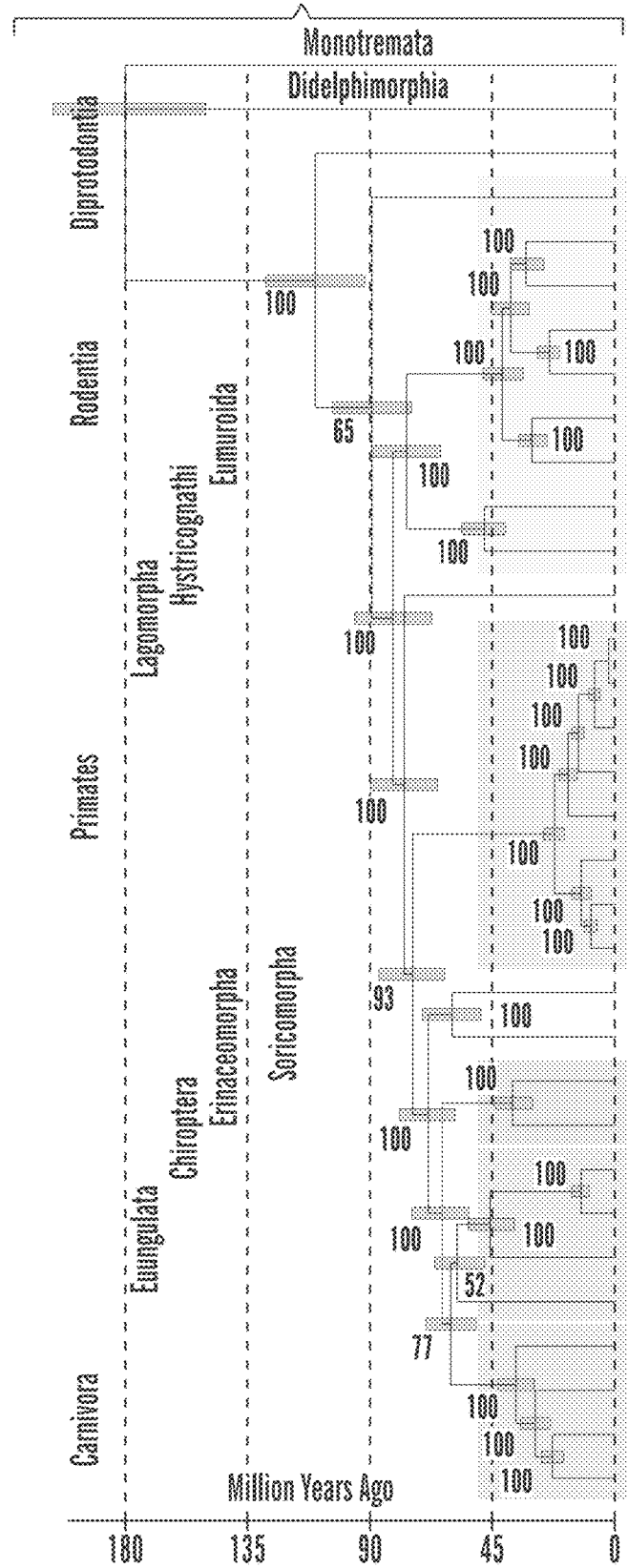
FIGS. 1A-1B Species phylogeny and life history traits.
Figure 1B:
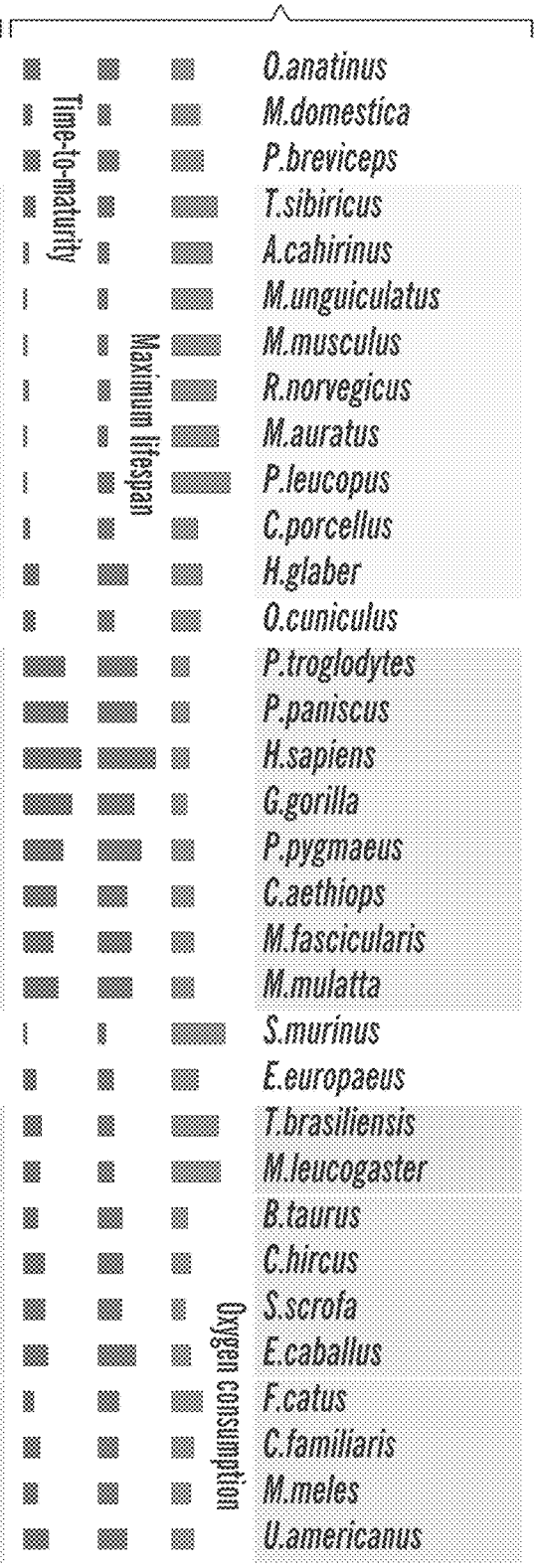
Figure 2A:
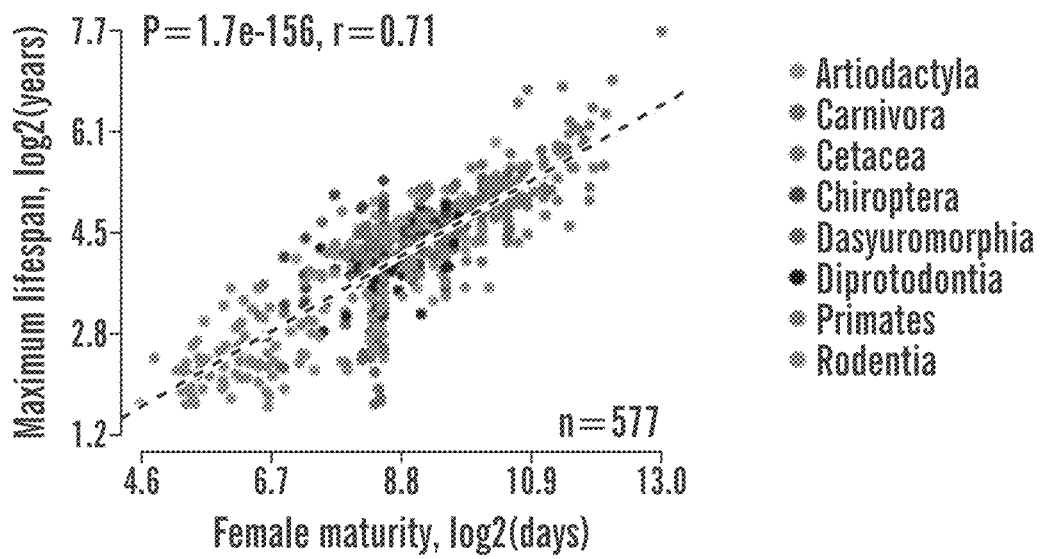
FIGS. 2A-2H. Relationship between maximum lifespan and other life histories.
Figure 2B:
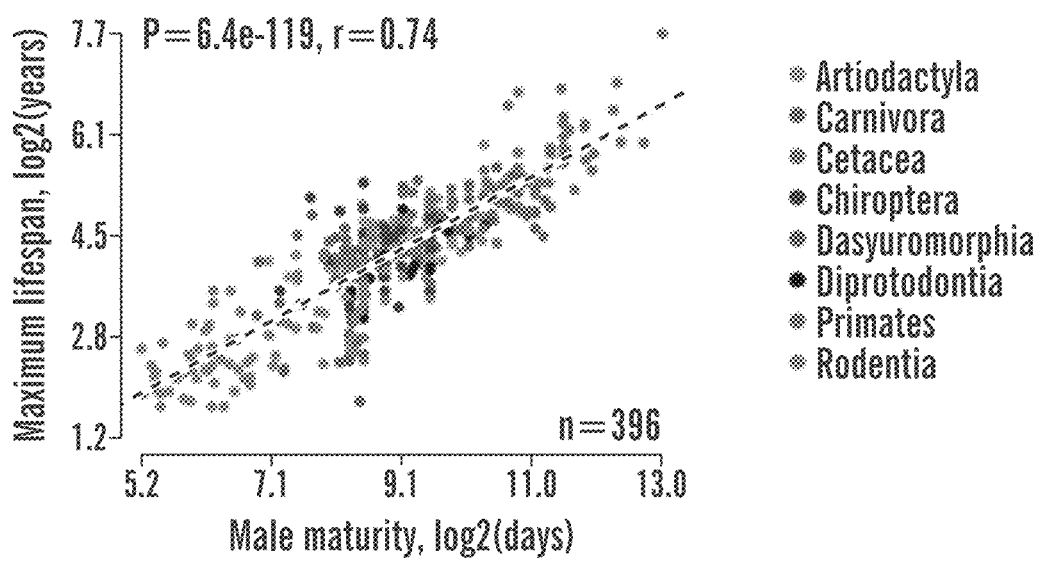
Figure 2C:
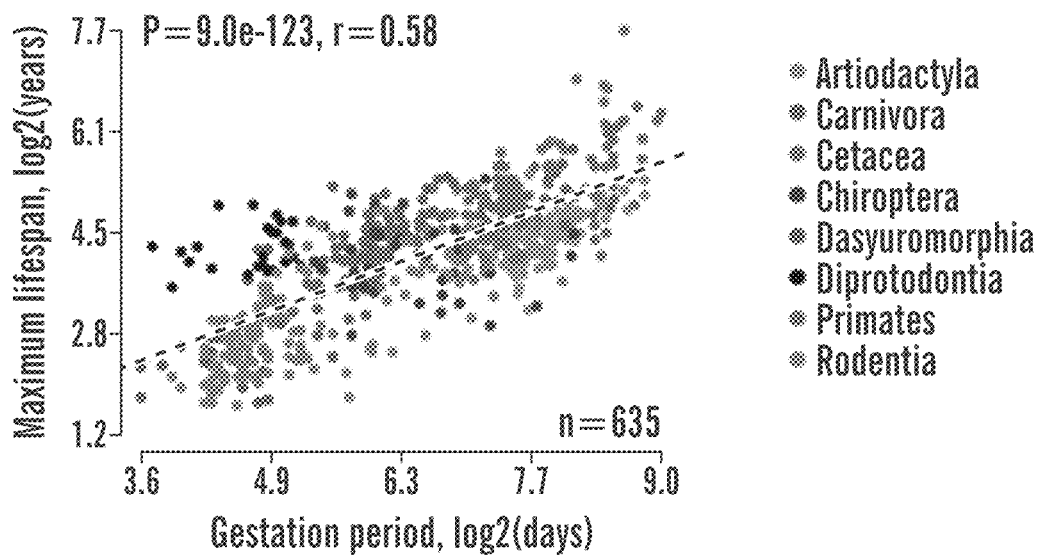
Figure 2D:
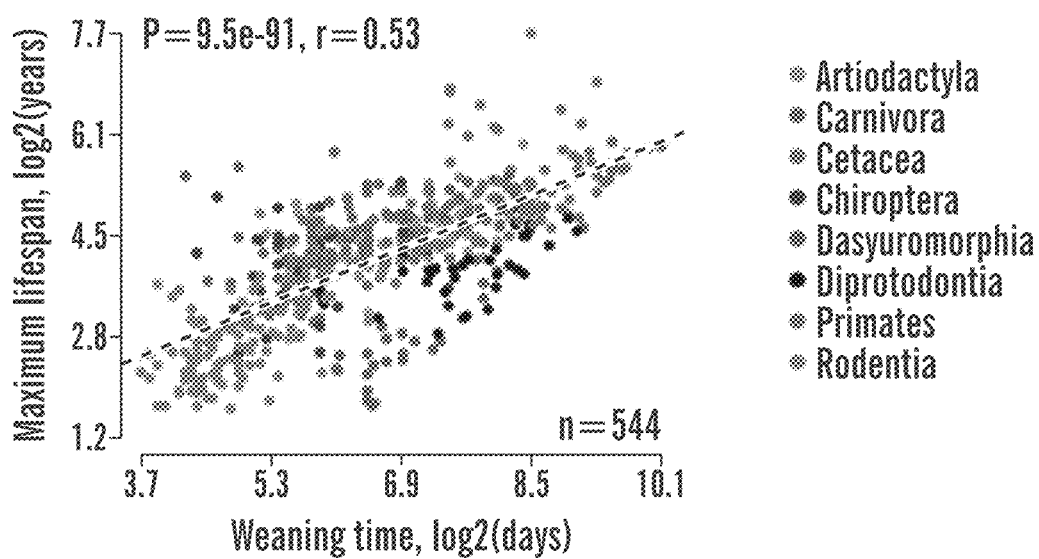
Figure 2E:
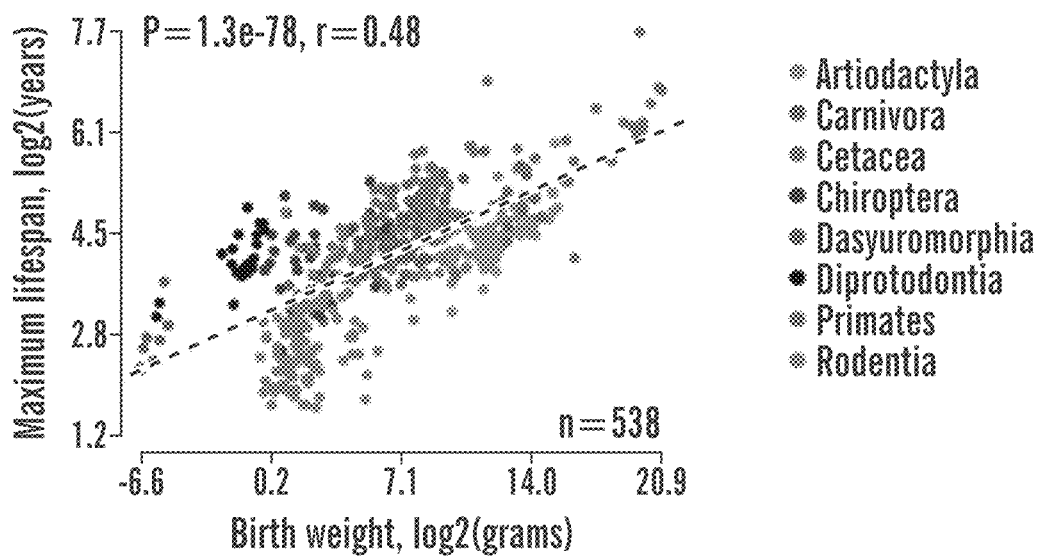
Figure 2F:
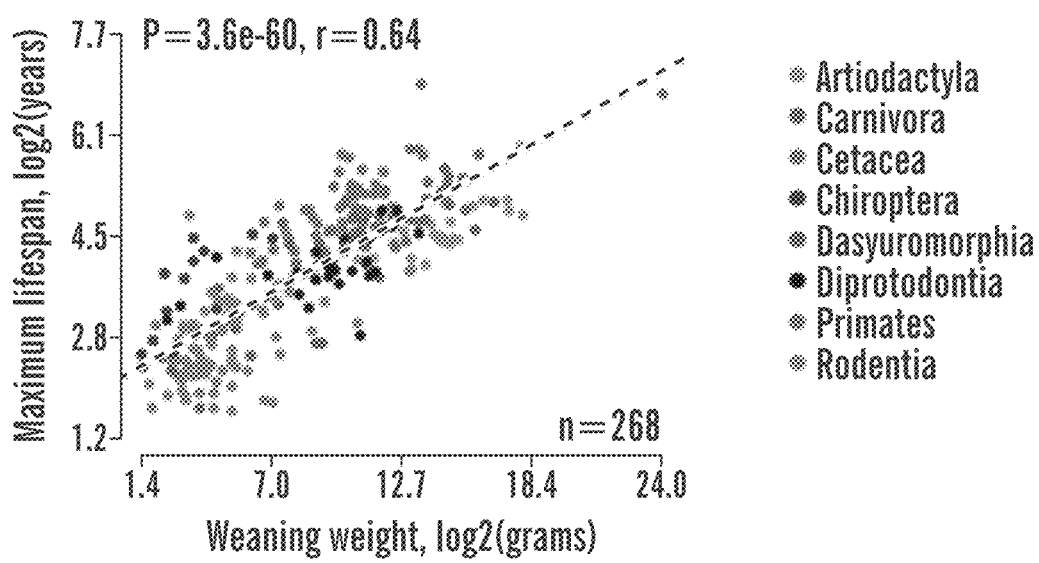
Figure 2G:
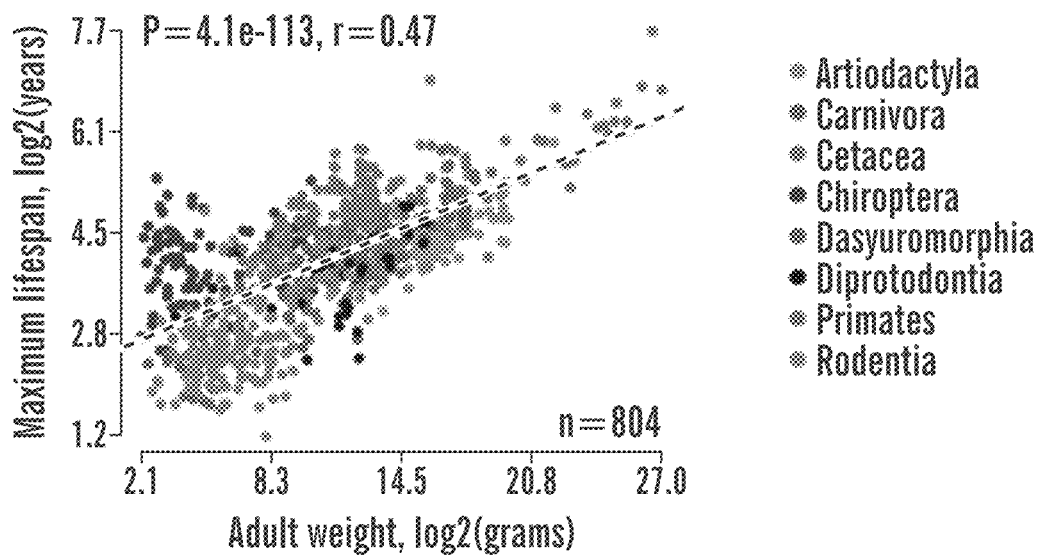
Figure 2H:
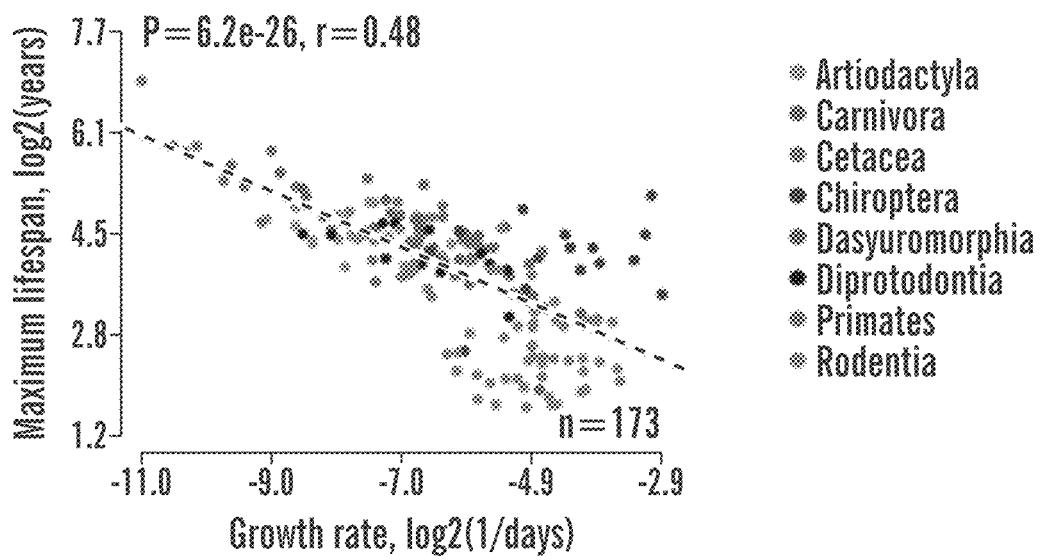

Most representatives of these lineages were placental mammals (*Placentalia*), except for platypus (*Monotremes*), opossum and sugar glider (*Marsupials*), and the total divergence of examined lineages corresponded to a period of ~160 million years (FIG. 1A). Evolution of these mammals yielded widespread variation in life histories, such as time to maturity, maximum lifespan and oxygen consumption (as a measure of basal metabolic rate, BMR) (FIG. 1B). The relationship between these life histories defines a set of lineage-specific functional tradeoffs and adaptive investments developed during environmental specialization. For example, most primates are characterized by longevity, slow growth and reduced BMR, whereas muroid species (*Eumuroida*) often use opportunistic-type strategies characterized by rapid development and growth, low body mass and short lifespan (FIG. 1B). Moreover, some organisms such as representatives of *Chiroptera* and *Histriocognathi*, feature *Eumuroida*-sized species, but possess life history attributes of larger, longer-lived mammals.

Gene expression in three organs (i.e., liver, kidney and brain) was analyzed because of their easier availability, dominance of one cell type (e.g., liver), difference in metabolic functions, size of organs (which is a limitation for smaller animals) and compatibility with previous data from other labs. The majority of the examined species was represented by duplicated (52-60% of species) or triplicated (30-42% of species) biological replicates to account for within species gene expression variation (Table 3). 25-60 millions of 51-bp paired-and RNA-seq reads for each biological replicate were generated (data not shown).

Reads were then mapped to genomic sequences of organisms from Ensembl and NCBI databases (data not shown). Database gene model annotations were used and 1-1 orthologous sequence relationships for these organisms were precomputed to calculate gene expression values defined as fragments per kilobase of transcript per million RNA-seq reads mapped (FPKM). Depending on species, RNA-seq read alignment efficiency varied from 55-99% (data not shown). For 12 species with no available genome sequences, full-length transcriptomic contigs using RNA-seq reads were de novo assembled (data not shown), encoded peptides were ab initio predicted (data not shown), and orthologous relationships with database proteins were inferred (data not shown). Analyses on the expression of protein coding genes with a 1:1 orthologous relationship were further focused, derived from the dataset of 19,643 unique groups of sequences (data not shown).

Relationship Between Life Histories and Phylogeny of Mammals

The extent to which phylogeny of the species in the present study influenced life history evolution was first examined, including gestation period, weaning time, maturation time, maximum lifespan, growth, body weight and metabolic rate (Table 4). The $\lambda$ model (Pagel, 1999) was used to test life history variation simultaneously against randomized value (no effect of phylogeny) and against the diffusive or the Brownian motion (BM) model (neutral drift). Species phylogeny provided the null distribution, given an appropriate model of neutral evolution. The method produces a quantitative estimate of the phylogenetic signal (the extent to which correlation in traits reflects shared evolutionary history of the species) in a character, the $\lambda$ parameter. Under the BM model, traits are inherited from a common ancestor and diverge linearly in a manner analogous to random walk. $\lambda$ describes the proportion of variance that can be attributed to BM. The value of $\lambda$ equal or close to 1 indicates a character evolution evolving under the stochastic process, whereas $\lambda<1$ indicates departure from neutral drift. The $\lambda$ model was ensured to perform well, even when the true model of trait evolution deviates from strict BM process (data not shown).

TABLE 4

Life histories of 33 mammals.

| Common name | Abbreviation | Gestation period (days)[1] | Weaning time (days)[1] | Adult weight (grams)[1] | Growth[2] | Time to maturity (days)[1] | Residual of tsex | Maximum life span (days)[1] | Residual of tmax | Oxygen consumption (ml/gram)[3] |
|---|---|---|---|---|---|---|---|---|---|---|
| Domestic cattle | bta | 211 | 180 | 540000 | 0.0031 | 365 | 0.254 | 7997.15 | 0.604 | 0.17 |
| Domestic goat | chi | 155 | 160 | 61000 | 0.0041 | 685 | 0.763 | 7358.4 | 0.761 | 0.19 |
| Domestic boar | ssc | 115 | 56 | 180000 | 0.0095 | 768 | 0.678 | 7665 | 0.678 | 0.11 |
| Domestic dog | caf | 63 | 56 | 20000 | 0.0244 | 510 | 0.723 | 5840 | 0.709 | 0.333 |
| Domestic cat | fca | 65 | 56 | 3900 | — | 210 | 0.423 | 6205 | 0.953 | 0.71 |
| Asian badger | mle | 49 | 90 | 13000 | 0.0196 | 365 | 0.568 | 5913 | 0.763 | 0.27 |
| American black | uam | 220 | 198 | 154250 | 0.0029 | 1278 | 1.166 | 12410 | 1.123 | 0.36 |
| Greater tube- | mhi | — | — | 12.75 | — | — | — | 3285 | 1.148 | 1.42 |
| Brazilian free- | tbr | 78 | 42 | 12.5 | 0.112 | 547 | 3.799 | 3650 | 1.280 | 1.51 |
| Short-tailed | mod | 15 | 53 | 105 | — | 122 | 0.536 | 1861.5 | 0.481 | 0.57 |
| Sugar glider | pbr | 16 | 122 | 110 | 0.0188 | 456 | 1.982 | 5110 | 1.310 | 0.69 |
| Hedgehog | eeu | 35 | 42 | 750 | — | 253 | 0.727 | 4270.5 | 0.831 | 0.45 |
| Old World | ocu | 30 | 26 | 1800 | 0.0228 | 240 | 0.571 | 3285 | 0.564 | 0.57 |
| Duck-billed | oan | 17 | 106 | 1250 | — | 548 | 1.411 | 6205 | 1.122 | 0.31 |
| Horse | eca | 337 | 274 | 350000 | — | 973 | 0.744 | 16790 | 1.350 | 0.25 |
| Vervet | cae | 162 | 182 | 5620 | — | 1825 | 3.400 | 11242 | 1.637 | 0.306 |
| Gorilla | ggo | 256 | 834 | 139842 | 0.0008 | 4015 | 3.742 | 16060 | 1.473 | 0.168 |
| Human | hsa | 280 | 639 | 70000 | 0.0005 | 5110 | 5.528 | 36500 | 3.699 | 0.21 |
| Long-tailed | mfa | 165 | 242 | 6362 | — | 1544 | 2.800 | 13505 | 1.932 | 0.298 |
| Rhesus monkey | mmu | 165 | 292 | 8235 | 0.0012 | 2007 | 3.443 | 14600 | 2.013 | 0.37 |
| Pygmy | ppa | 232 | 635 | 39925 | — | 3194 | 3.900 | 18250 | 2.005 | 0.203 |
| Orangutan | ppy | 249 | 1003 | 64475 | 0.0009 | 2555 | 2.813 | 21425.5 | 2.197 | 0.3 |
| Chimpanzee | ptr | 229 | 1111 | 44983 | 0.0007 | 2920 | 3.475 | 19491 | 2.105 | 0.26 |
| Spiny mouse | aca | 38 | 14 | 45 | 0.0147 | 59 | 0.311 | 2153.5 | 0.628 | 1.1 |
| Guinea pig | cpo | 68 | 18 | 728 | 0.0106 | 76 | 0.220 | 4380 | 0.856 | 0.55 |
| Naked mole-rat | hgl | 70 | 36 | 35 | 0.0046 | 365 | 2.031 | 10329.5 | 3.123 | 0.66 |
| Golden hamster | mau | 16 | 20 | 105 | 0.0574 | 48 | 0.211 | 1423.5 | 0.367 | 1.5 |
| Mongolian | mun | 25 | 24 | 53.2 | 0.0324 | 36 | 0.183 | 1387 | 0.395 | 1.15 |
| House mouse | mus | 19 | 22 | 20.5 | 0.0298 | 42 | 0.262 | 1460 | 0.477 | 1.667 |
| White-footed | ple | 26 | 22 | 23 | 0.0456 | 44 | 0.268 | 2883.5 | 0.926 | 2.2 |
| Norway rat | rno | 21 | 25 | 300 | — | 70 | 0.245 | 1825 | 0.405 | 1.32 |
| Siberian | tsi | 35 | 40 | 85 | — | 350 | 1.609 | 3504 | 0.933 | 1.25 |
| House shrew | smu | 30 | 19 | 45 | 0.0643 | 36 | 0.190 | 1168 | 0.341 | 1.97 |

In Table 4,
[1]Life histories were collected from published literature and AnAge database (www.genomics.senescence.info).
[2]An estimate of Gompertz function defining the fraction of body weight accumulating per day (data from AnAge).
[3]Oxygen consumption is the volume of oxygen (ml) consumed in 1 hour. Here, the data are adjusted by species body weight (grams).

The data showed that life history variation of animals in the present study significantly departs from the diffusive model of evolution. For example, phylogeny could explain only a moderate portion of variance ($\lambda=0.65$, $P=0.02$, likelihood-ratio test) in maximum lifespan (data not shown). Body weight exhibited greater constraints than the other examined traits ($\lambda=0.39$, $P=0.003$, likelihood-ratio test). The results indicated that, with increasing genetic distance, phenotypic divergence becomes nonlinear within and between lineages.

Although life history evolution deviated from phylogeny, distinct traits preserve covariance with each other. To demonstrate this, the life history data of ~800 species of mammals (de Magalhaes & Costa, 2009) were analyzed using non-phylogenetic regression (FIG. 2). The analysis showed that, for example, maximum lifespan strongly covariates with body weight ($r^2=0.47$, $P=4\times10^{-113}$, F-test), time to maturity ($r^2=0.71$, $P=1\times10^{-156}$, F-test) and other examined traits (FIG. 2). These data indicate that selective forces governed parallel evolution of life histories. These forces maximized fitness and interdependence between distinct traits and can also represent conserved underlying mechanisms.

Life History Evolution Shaped Interspecies Gene Expression Variation

Mammalian life histories exhibited drift and selection (Barbosa-Morais et al., 2012; Blomberg et al., 2003). In vertebrates, life history evolution, governed by selective constraints, shaped interspecies gene expression variation (Whitehead & Crawford, 2006a; Giger et al., 2006). Yet, little research has been conducted to determine the mechanisms of trait evolution in mammals because the exceptional level of life history variation was historically influenced by complex interactions between genetics and environment.

Figure 10:
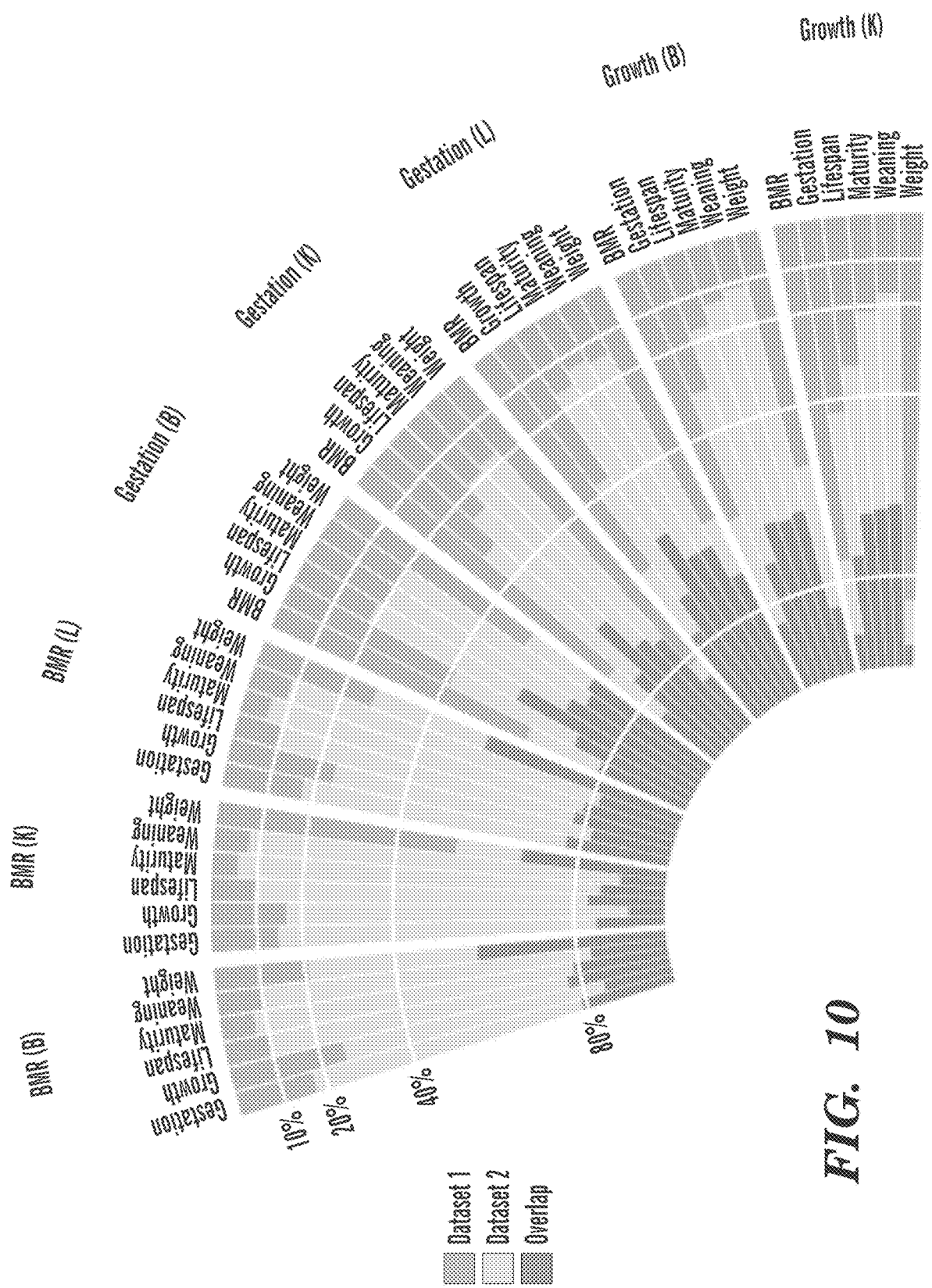
FIG. 10. Overlap of genes whose expression variation associate with life histories. Each color-coded bar shows percentages of genes (scale at the beginning) unique for two data sets (blue, yellow) and percentage of common genes (red). L, liver; K, kidney; B, brain.
Figure 10:
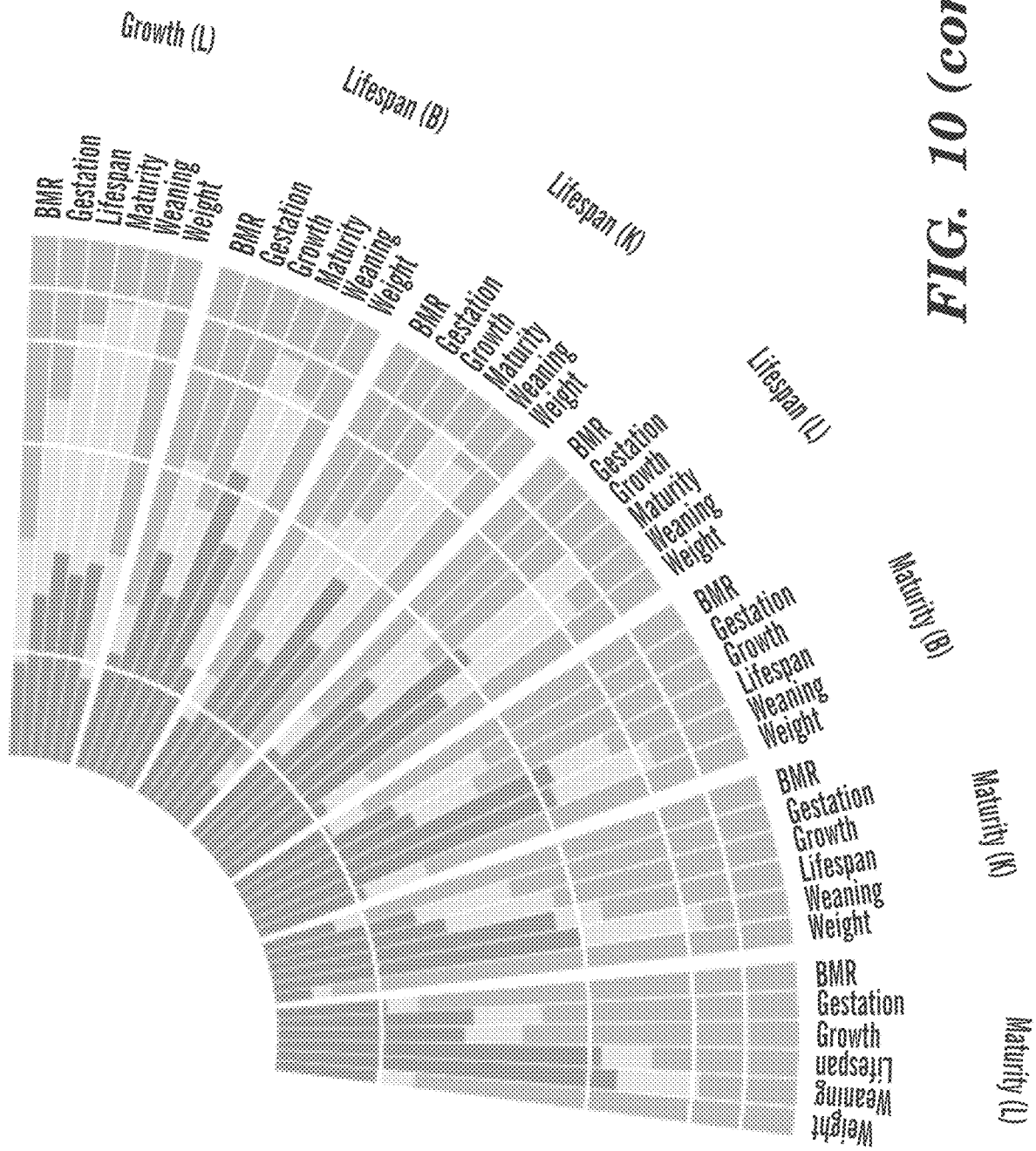
Figure 10:
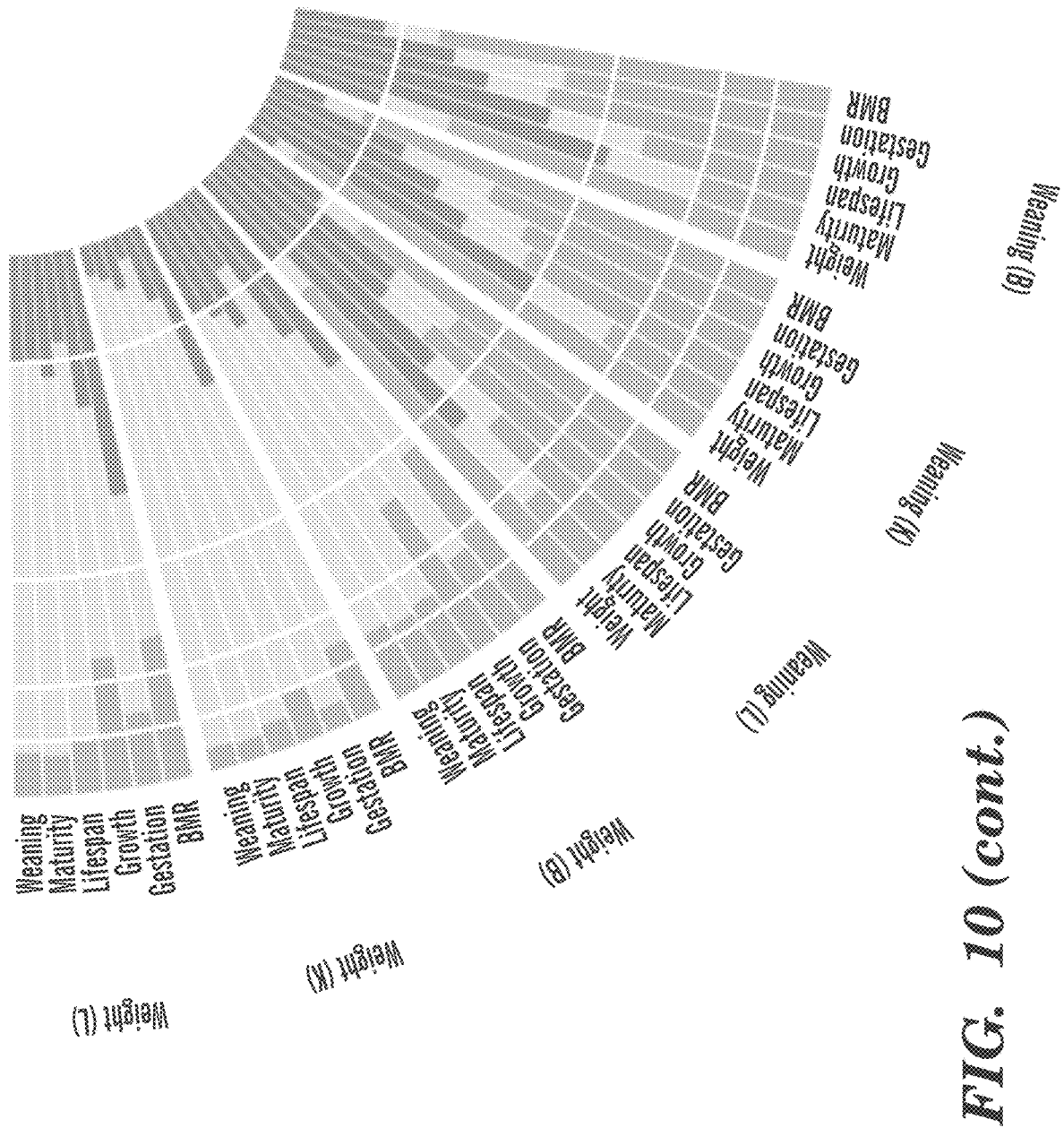

Because life history variation of animals in the present study significantly departed from the model of neutral evolution, non-phylogenetic ordinary least squares (OLS) was adopted instead of phylogenetic regression to assess the relationship between transcript levels and whole-organism traits. When used improperly the phylogenetic regression can have poor statistical performance, even under some circumstances in which the type I error rate of the method is not inflated over its nominal level (Revell, 2010). Kruskal-Wallis one-way analysis of variance was further applied as a post-hoc test to ensure that interspecies gene expression variation exceeded those within species. The analyses identified gene sets whose expression levels significantly associate (FDR corrected $P<0.05$, F-test) with life history variation (Table 5, FIG. 10).

Figure 3A:
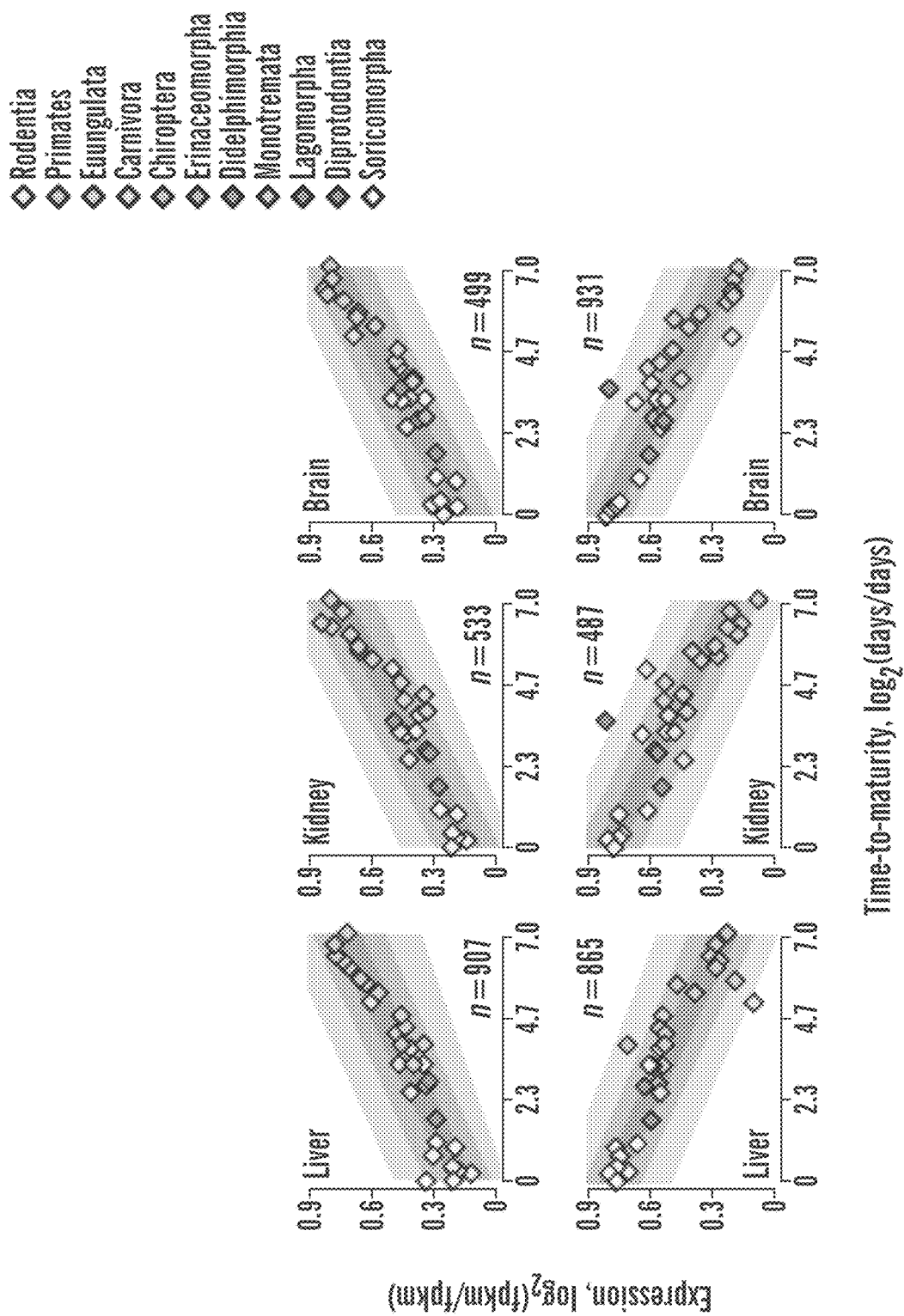
FIGS. 3A-3F. Covariance of transcript levels and life history variation.

Overall, at the level of FDR corrected $P<0.05$, we detected ~5,000 unique 1-1 orthologs significantly associated with 7 traits in the three organs with some overlap (381 transcripts) between organs (Table 1). As an example, FIG. 3A shows expression profiles of 3249 transcripts associated with gradient of time to maturity variation in liver, kidney and brain. Although organisms examined in the study represent both laboratory and non-laboratory populations, the sources of measurement error such as sampling and biological variations were not overdispersed compared to the estimate.

Longevity is a complex trait defined by genetics and environment (de Magalhaes et al., 2007). Maximum lifespan varies for the same species and accuracy of the estimates can be influenced by environmental conditions and sample size

TABLE 1

Statistics for genes whose expression variation is associated with life history variation.

| Variable ($P_{FDR}$ < 0.05)[1] | Liver (n = 14679)[2] | | Kidney (n = 16063) | | Brain (n = 16424) | | Combined[5] |
|---|---|---|---|---|---|---|---|
| | Nb. of genes[3] | % from total | Nb. of genes | % from total | Nb. of genes | % from total | |
| Gestation period | 1017 (121) | 6.9 (0.8) | 588 (126) | 3.7 (0.8) | 926 (168) | 5.6 (1.0) | 2097 (75) |
| Weaning time | 1690 (198) | 11.5 (1.3) | 1098 (203) | 6.8 (1.3) | 1453 (246) | 8.8 (1.5) | 3295 (193) |
| Body weight | 506 (44) | 3.4 (0.3) | 116 (8) | 0.7 (0.0) | 549 (62) | 3.3 (0.4) | 1062 (11) |
| Growth | 918 (116) | 6.5 (0.8) | 698 (173) | 4.6 (1.1) | 783 (123) | 5.0 (0.8) | 1989 (79) |
| Time to maturity | 1740 (149) | 11.9 (1.0) | 998 (88) | 6.2 (0.5) | 1393 (95) | 8.5 (0.6) | 3249 (170) |
| Maximum lifespan | 1399 (90) | 9.5 (0.6) | 713 (31) | 4.4 (0.2) | 1195 (57) | 7.3 (0.3) | 2683 (119) |
| Metabolic rate | 510 (44) | 3.5 (0.3) | 213 (30) | 1.3 (0.2) | 438 (37) | 2.7 (0.2) | 1042 (15) |
| Combined[4] | 2610 (134) | 17.8 (0.9) | 1753 (30) | 10.9 (0.2) | 2384 (97) | 14.5 (0.6) | 4996 (381)[6] |

In Table 1,
[1]$P_{FDR}$ denotes OLS P-value cut-off;
[2]n denotes total number of orthologous groups assayed in the analysis;
[3]Number of unique genes associated with trait variation and number of genes specific for a trait (in brackets);
[4]Number of unique genes identified in the organ and its overlap between all traits (in brackets);
[5]Number of unique genes identified in three organs for a specific trait and inter-organ overlap (in brackets);
[6]Number of unique genes identified in three organs for all traits and inter-organ overlap (in brackets).

The analyses provided evidence that the interspecies variation in the gene expression of numerous orthologs in mammals was shaped by evolution constraints in agreement with gradient in life history change. Life history variation of animals in the present study could explain ~11-18% of total variability in interspecies transcript levels (Table 1), whereas variability in the expression of other orthologs could be explained by drift (data not shown) and stabilizing constraints (data not shown). It was reported previously that life history variation governed by natural selection explains expression variation of 22% genes in marine species (Whitehead & Crawford, 2006b). Thus, gene expression evolution in vertebrates exhibits widespread selective constraints, whereas drift appears to account for less variation than expected (Khaitovich et al., 2004a).

Figure 3B:
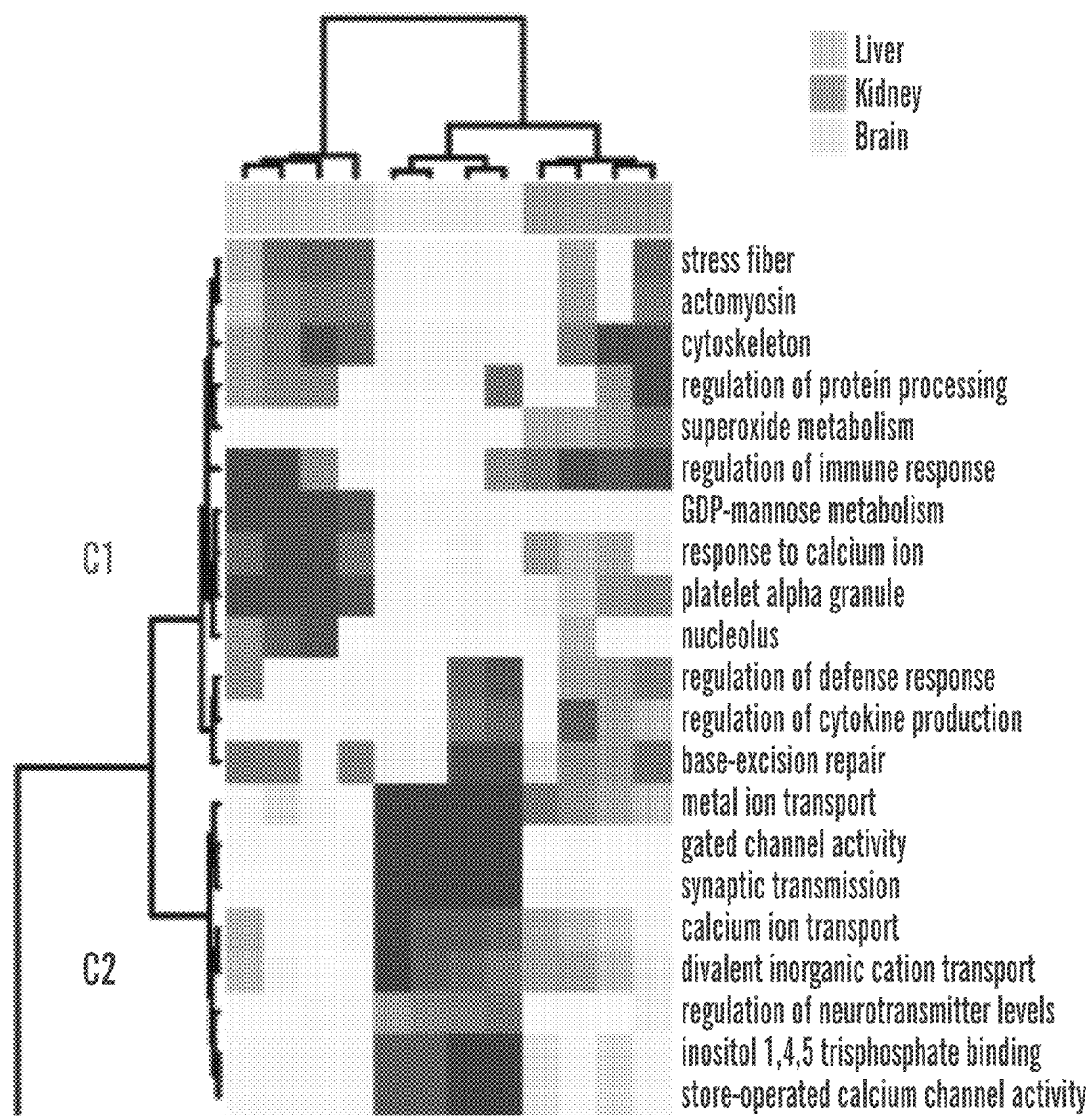
Figure 3B:
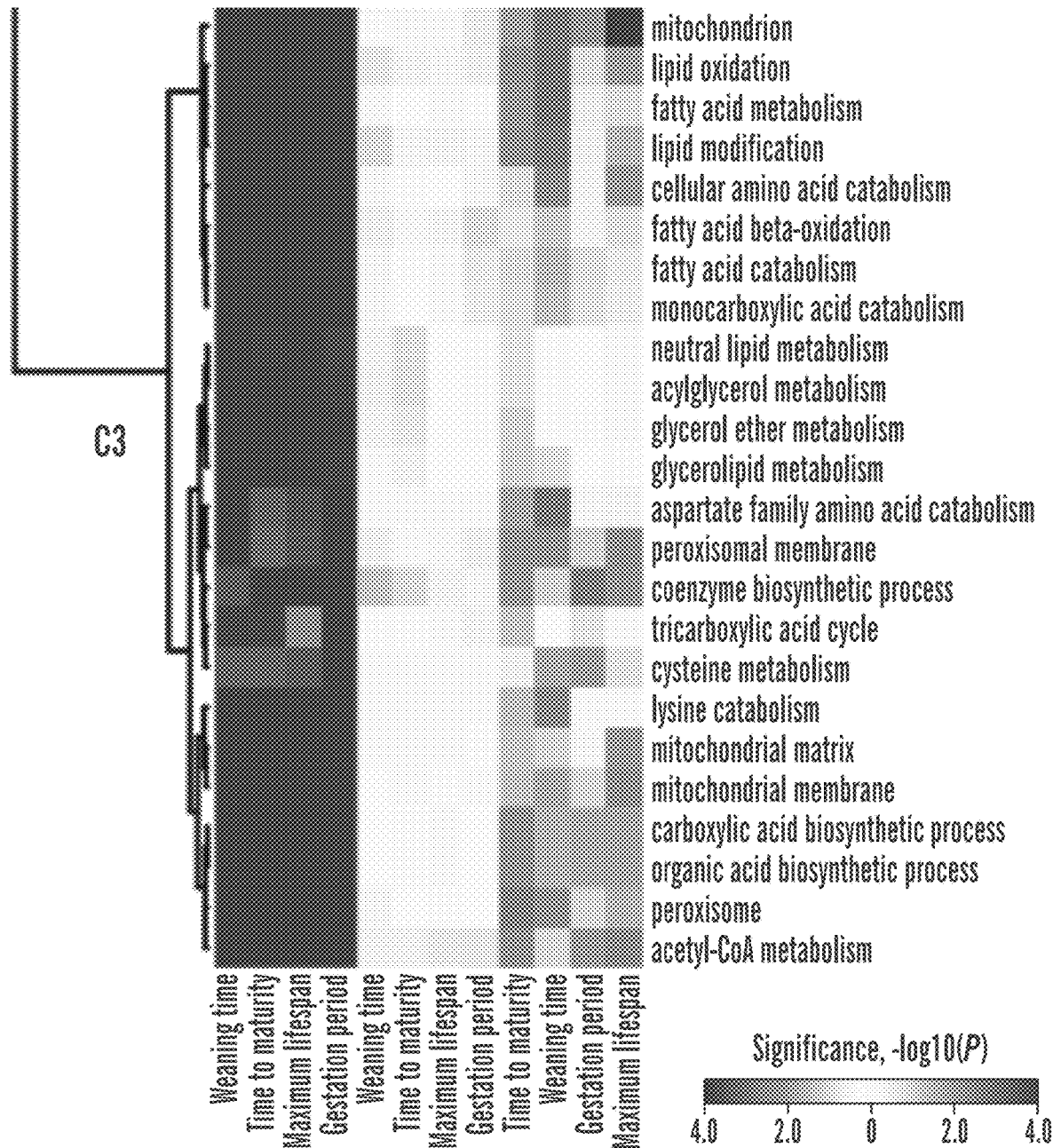

Gene set enrichment analysis revealed statistically non-random distribution of transcripts positively and negatively correlated with life history traits among GO functions (FIGS. 3B and 4, Dataset 2 (not included)). In liver, downregulated mitochondrial metabolic GO functions were detected, such as metabolism of saturated and unsaturated fatty acids, degradation of amino acids and their derivatives linked to ATP production through the TCA cycle and mitochondrial respiratory pathways (FIG. 3B, cluster C3). In brain, downregulated functions included inositol and calcium-mediated signaling pathways and transmembrane channel transport (FIG. 3B, cluster C2). DNA repair and defense GO functions were positively associated with gradient in lifespan variation, maturation time and related traits (FIG. 3B, cluster C1).

Figure 3C:
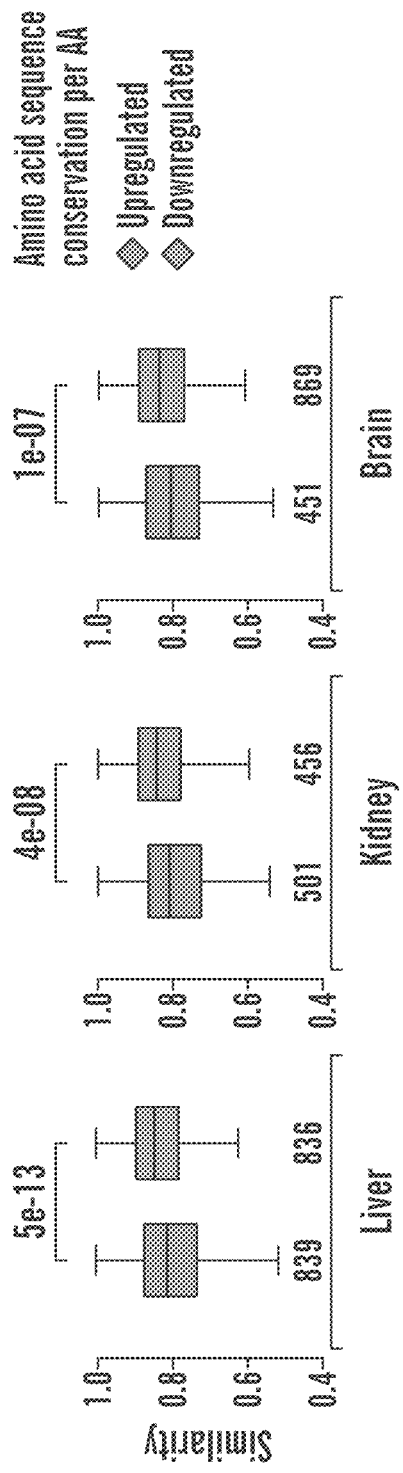
Figure 3D:
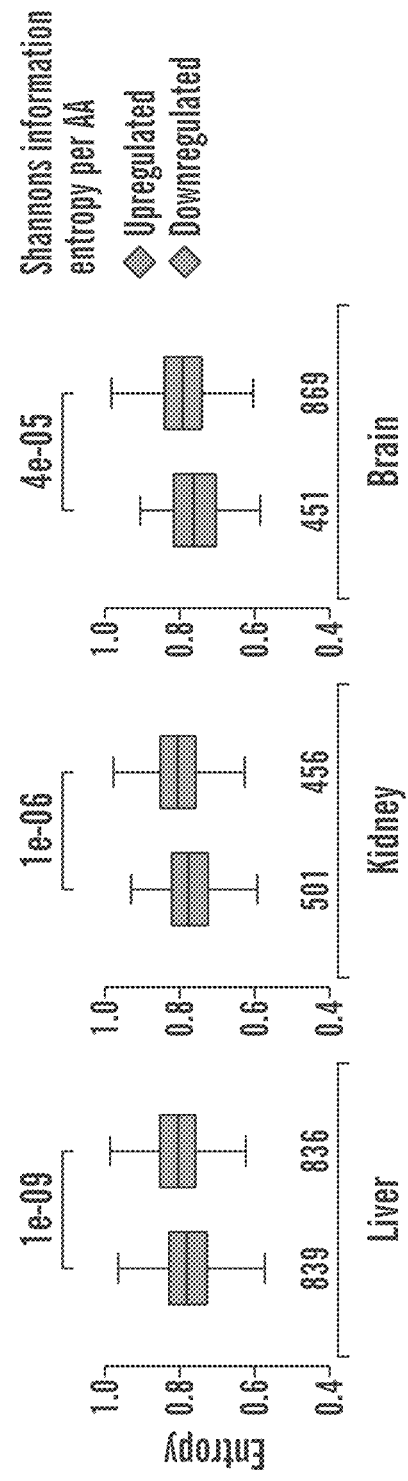
Figure 3F:
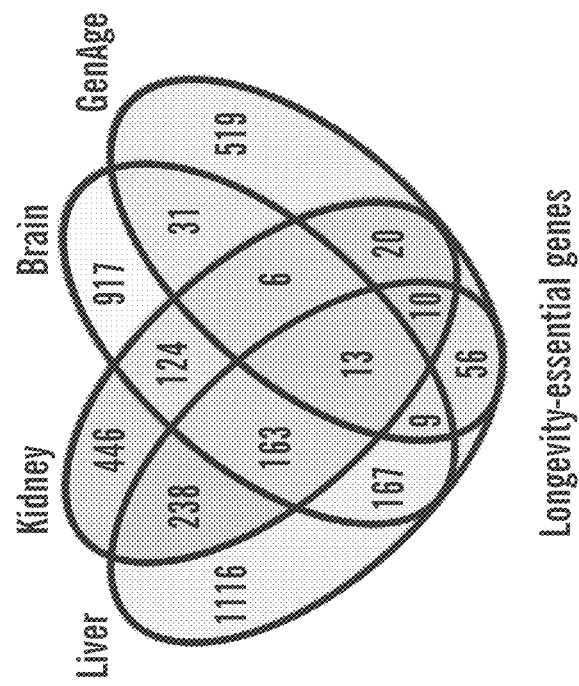

A minor overlap was detected, which did not reach the level of statistical significance (P >0.05, hypergeometric test), between genes shown to alter lifespan in model organisms (de Magalhaes & Costa, 2009) and genes associated with natural variation in life histories (FIG. 3F). The results indicate that genome-wide reprogramming of gene expression influences lifespan of mammals at the level of species, as opposed to the role of individual master gene(s) with pleiotropic effect(s).

(Kawasaki et al., 2008). Although gene sets listed in Table 5 showed significant overlap (FIG. 10), the observation may be inflated partially by quality of independent variables. The gene set associated with maturation time was further used as a representative of other life history sets to assess sequence conservation of the encoded proteins across the examined taxa. The analysis showed that the downregulated orthologs were more conserved than the upregulated ones (FIG. 3C) Shannon' information entropy criterion (Mirny & Shakhnovich, 1999) was further used to evaluate the number of radical amino acid substitutions and found that the number of such substitutions was also lower in the downregulated sequences (FIG. 3D).

Figure 3E:
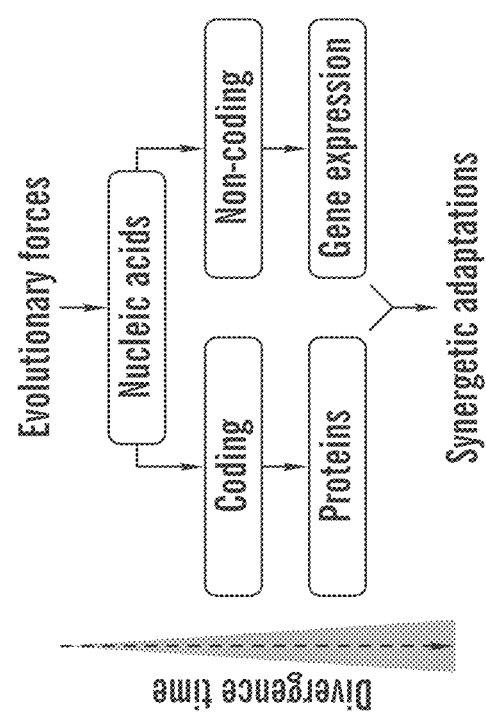

A positive relationship between amino acid substitution rate and gene expression divergence was previously reported for several species of mammals (Khaitovich et al., 2005; Misawa & Kikuno, 2011; Duret & Mouchiroud, 2000). The phenomenon can be explained by non-uniform GC content in the genome defining frequencies of transitions and transversions (Misawa & Kikuno, 2011). The present data indicate parallel evolution of biological sequences and their expression levels (FIG. 3E) and that the degree of purifying forces varies between distinct functional classes of sequences.

Intimate Relationship of Life History Variation and Central Metabolism

Figure 6A:
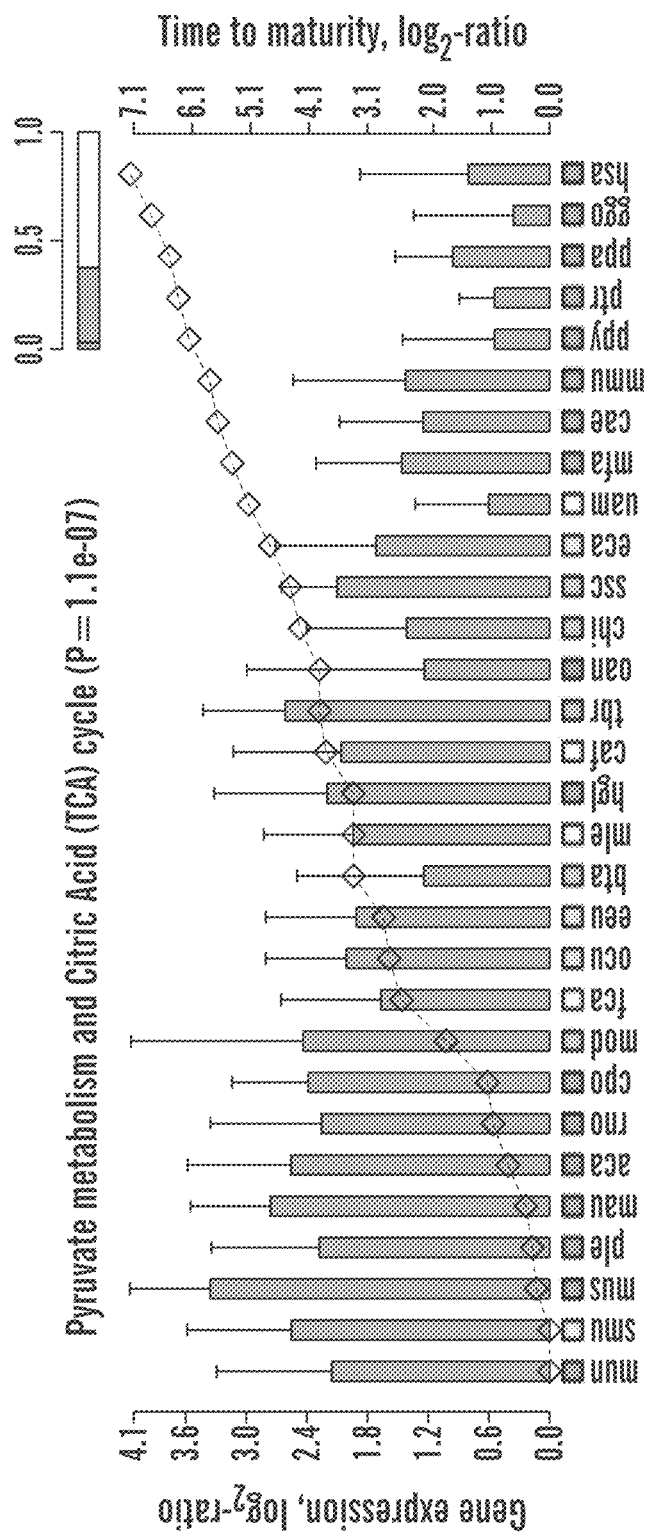
FIGS. 6A-6C. Gene expression variation associated with the TCA cycle in liver.
Figure 6B:
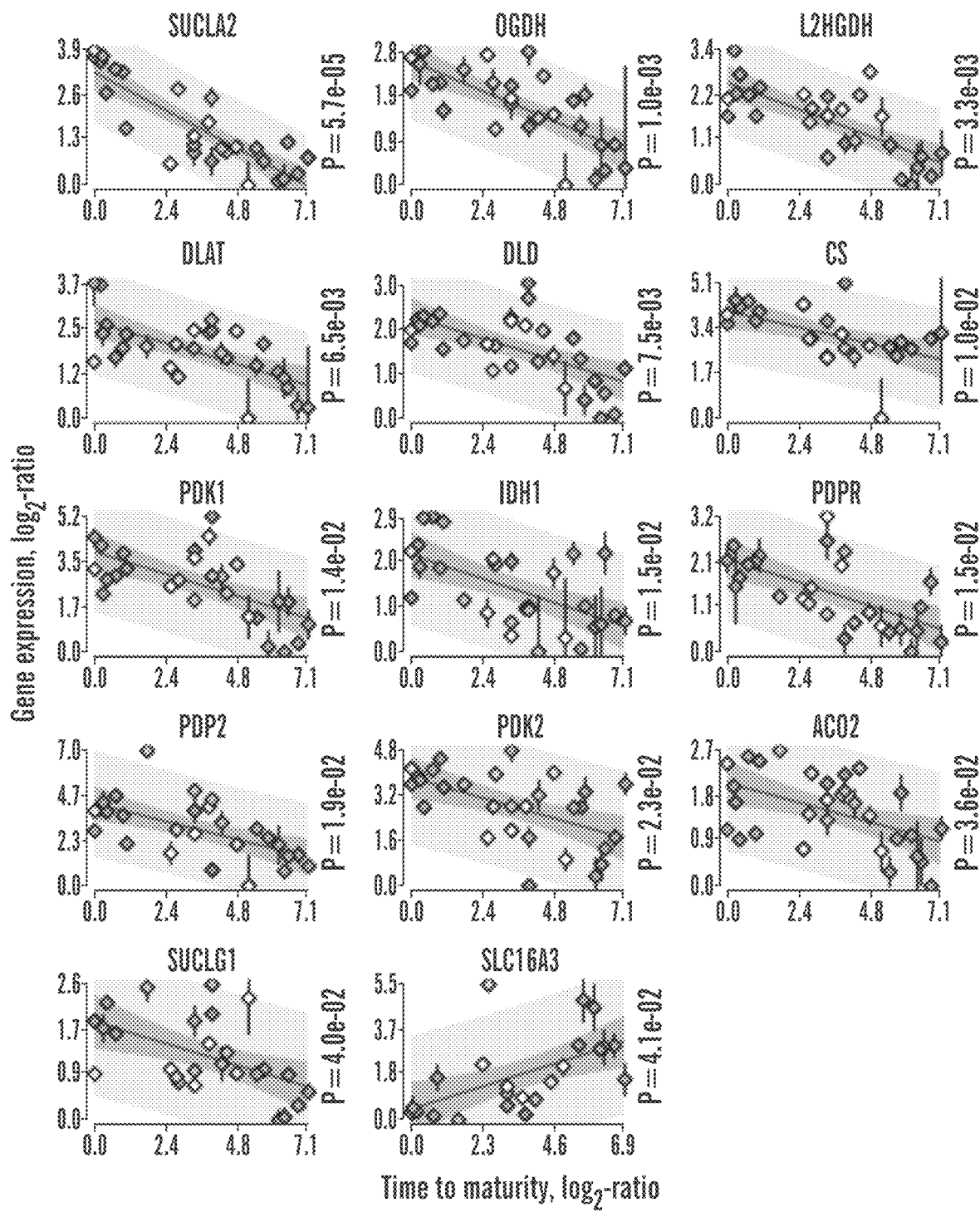
Figure 6C:
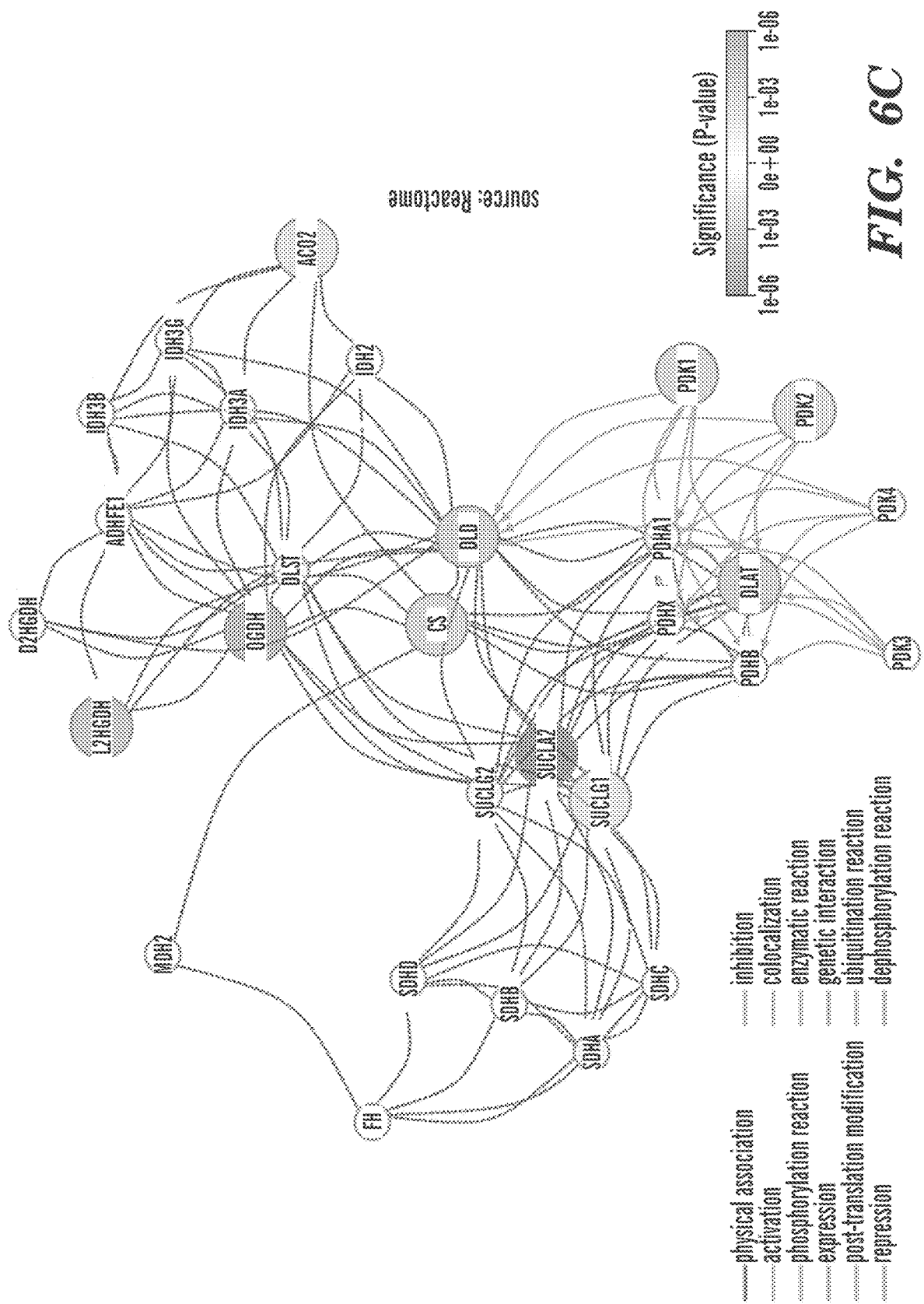

Most relevant genes and biological pathways associated with life histories were examined (FIGS. 4, 5). Gene set enrichment analysis revealed statistically significant label overrepresentation in the central energy metabolism combining numerous associated pathways such as pyruvate metabolism ($P=1\times10^{-7}$, hypergeometric test, FIG. 6), carbohydrate degradation pathways ($P=1\times10^{-5}$, hypergeometric test, data not shown), catabolism of tryptophan ($P=4\times10^{-5}$, hypergeometric test, data not shown), lysine ($P=3\times10^{-6}$, hypergeometric test, data not shown) and valine ($P=7\times10^{-7}$, hypergeometric test, data not shown), oxidation and biosynthesis of fatty acids ($P=2\times10^{-5}$, hypergeometric test, data not shown), Ppar ($P=4\times10^{-4}$, hypergeometric test, data not shown), peroxisome (P=1×10$^{-6}$, hypergeometric test, data not shown), Ampk (P=8×10$^{-4}$, hypergeometric test, data not shown), growth hormone (Gh/Ghr) signaling and others (FIG. 5). Interestingly, divergent evolution of marine vertebrates led to adaptive variation in growth and lifespan (St-Cyr et al., 2008) associated with expression signatures closely related to those observed in the studied mammals, indicating fundamental relatedness of strategies governing parallel life history and transcriptome evolution in vertebrates.

Genetic interventions re-balancing expression of the effectors of these well-established biological networks are capable of modifying life history attributes in opposite directions. For example, in yeast changing gene dosage for glycolytic enzyme genes resulted in variation in life history traits such as growth and lifespan (Wang et al., 2010). In mice, deletion of Ghr results in increased longevity (Coschigano et al., 2003), whereas elevated growth hormone treatment during development shortens lifespan (Panici et al., 2010). Consistent with experimental data, natural expression divergence of Ghr negatively correlates with life history variation of mammals (FIG. 5, Table 5).

Statistical analysis revealed significant relationships between life history variation and expression levels of numerous genes involved in DNA repair, defense and detoxification (FIG. 5). Without wishing to be bound by theory, a functional classification of these orthologs based on the activities in Datasets 3 and 4 (not included) was offered. As a less established example, haptoglobin (Hp) and hemopexin (Hpx) were reported to prevent oxidative damage resulting from hemoglobin in erythrocytes as well as protect kidney in humans (Burbea et al., 2004; Fagoonee et al., 2005). There is a positive relationship between lifespan and liver expression of Hp ($r^2$=0.51, FDR corrected P=5× 10$^{-3}$, F-test) and Hpx ($r^2$=0.38, FDR corrected P=1×10$^{-2}$, F-test), although such a relationship can also reflect species allometry and constitutive differences among homologous organs.

One would expect that changes in gene expression result in correlated downstream changes in protein levels because of the positive relationship between transcript and protein levels in mammals (Schwanhausser et al., 2011). Therefore, rates of bioenergetic conversion and/or its efficiency may be differentially adjusted, in an organ-specific manner, in mammals in accordance with gradient of life history changes. As a consequence, this would contribute to the levels of metabolic by-products which are thought to influence aging (Houtkooper et al., 2012; Barja, 1998; Gladyshev, 2013). Without wishing to be bound by theory, a higher rate of metabolism may allocate energy resources necessary for growth and reproduction in the opportunistic-type organisms such as *Eumuroida* species.

Relationship Between Body Weight and Longevity Traits

Body weight was shown to exhibit non-random association with life history traits (de Magalhaes et al., 2007). When the body size is increased in natural populations, fecundity is maximized through a longer period of growth and increased lifespan, providing trade-offs between reproduction and survival mediated through body size and development time.

Figure 7A:
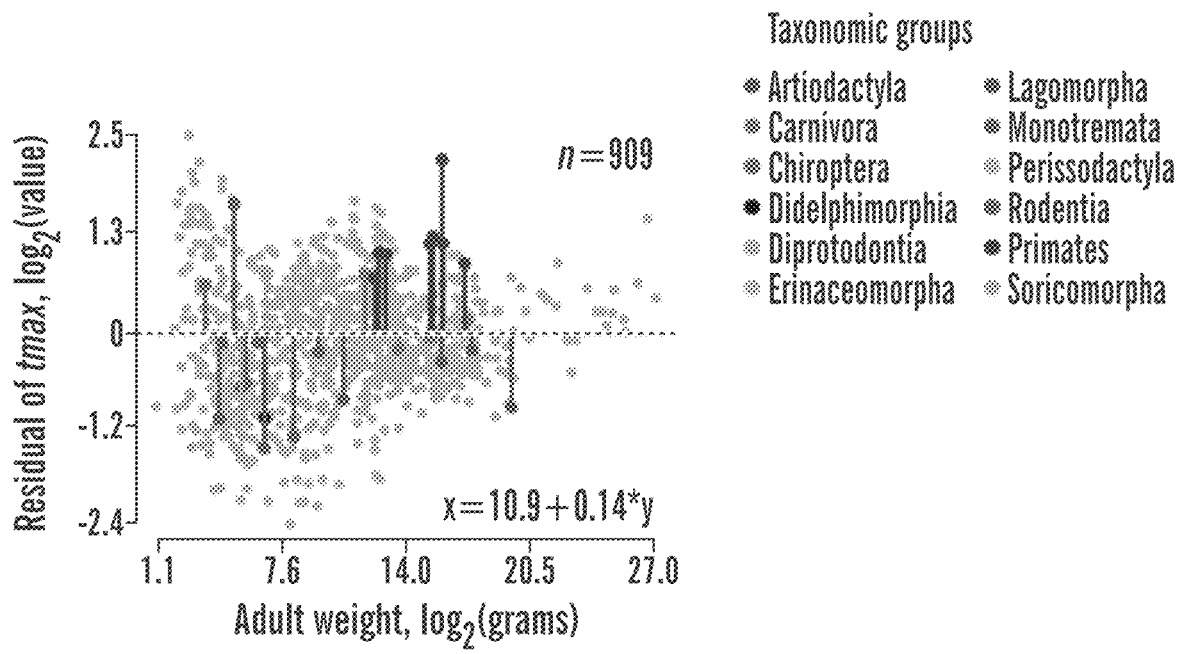
FIGS. 7A-7C. Gene expression signatures of the residual of life histories.
Figure 7B:
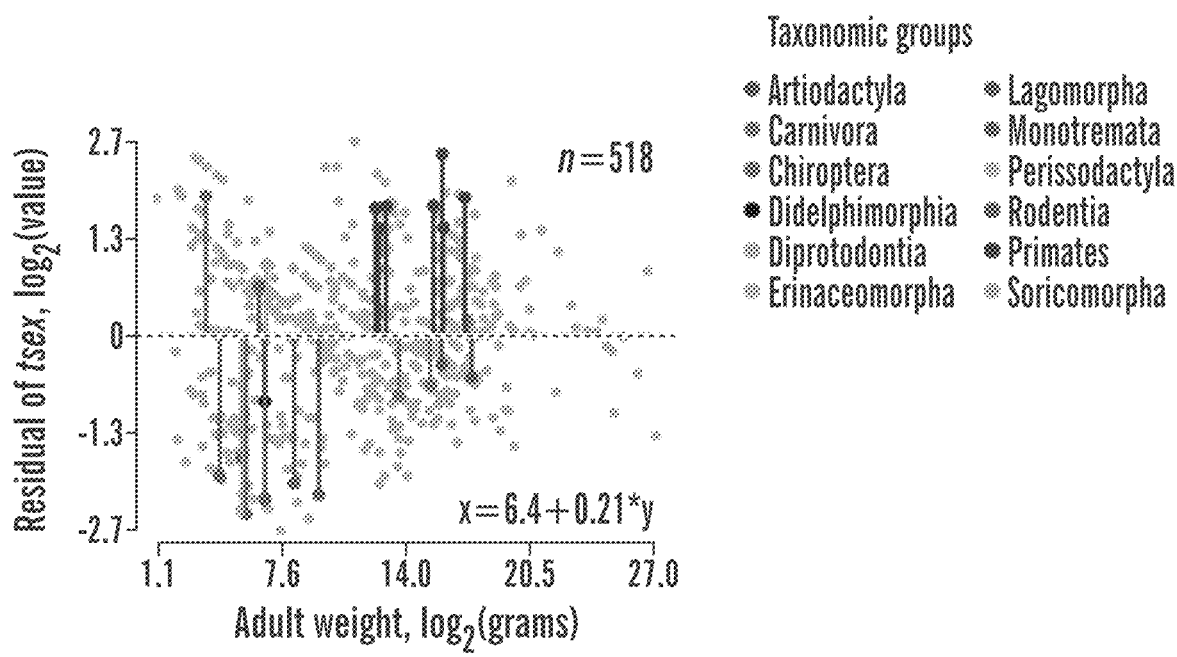

The residuals of several traits (maturation time and maximum lifespan) were calculated to elucidate whether these variables evolved under the stochastic evolution. Allometric component was excluded from the linear regression models (FIGS. 7A and 7B) and calculated the λ model on the residuals of life histories (data not shown). It was found that the residual of maturation time significantly departs from neutral evolution defined by phylogeny variance structure (λ=0.72, P=0.04, likelihood-ratio test). The analyses also demonstrated a similar relationship of phylogeny and residuals of other traits, such as maximum lifespan and oxygen consumption (data not shown). The observations provided further evidence of constraints contributing to life history evolution in mammals and without wishing to be bound by theory these constraints probably act through interplay between selection and drift.

Non-Random Association of Gene Expression with Life History Residuals

Genes whose expression variation explains the residual of maximum lifespan and maturation time were identified by examining statistical interaction between life histories and body weight variable in the OLS model (FIG. 7, Table 2). The identified genes overlapped with the gene sets associated with respective life histories, but not with body weight (data not shown). The analysis showed that the residual of life history traits does not provide additional statistical support to explain life history variation at the level of gene expression, although significantly reduces the associated gene sets (Dataset 5 (not included)).

TABLE 2

Statistics for genes whose expression variation is associated with the residuals of life histories.

| Variable ($P_{FDR}$ < 0.05)[1] | Liver (n = 14679)[2] | | Kidney (n = 16063) | | Brain (n = 16424) | | |
|---|---|---|---|---|---|---|---|
| | Nb. of genes[3] | % from total | Nb. of genes | % from total | Nb. of genes | % from total | Combined[5] |
| Maximum lifespan | 659 (123) | 4.5 (0.8) | 469 (65) | 2.9 (0.4) | 366 (36) | 2.2 (0.2) | 1255 (43) |
| Time to maturity | 1186 (650) | 8.1 (4.4) | 897 (493) | 5.6 (3.1) | 948 (618) | 5.8 (3.8) | 2428 (113) |
| Combined[4] | 1309 (536) | 8.9 (3.7) | 962 (404) | 6.0 (2.5) | 984 (330) | 6.0 (2.0) | 2585 (126)[6] |

In Table 2,
[1]$P_{FDR}$ denotes OLS P-value cut-off;
[2]n denotes total number of orthologous groups assayed in the analysis;
[3]Number of unique genes associated with trait variation and number of genes specific for a trait (in brackets);
[4]Number of unique genes identified in the organ and its overlap between all traits (in brackets);
[5]Number of unique genes identified in three organs for a specific trait and inter-organ overlap (in brackets);
[6]Number of unique genes identified in three organs for all traits and inter-organ overlap (in brackets).

Figure 7C:
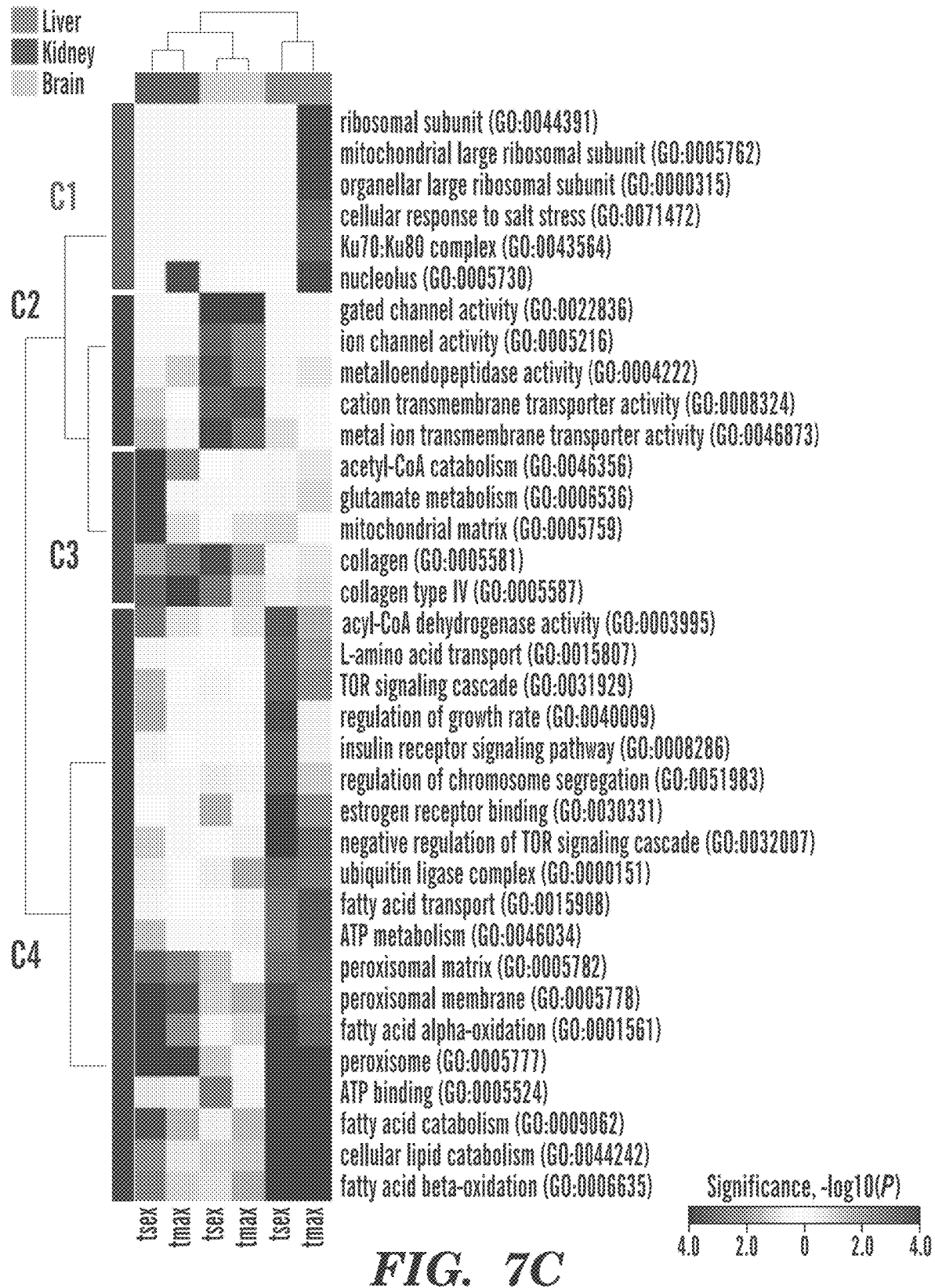
Figure 8A:
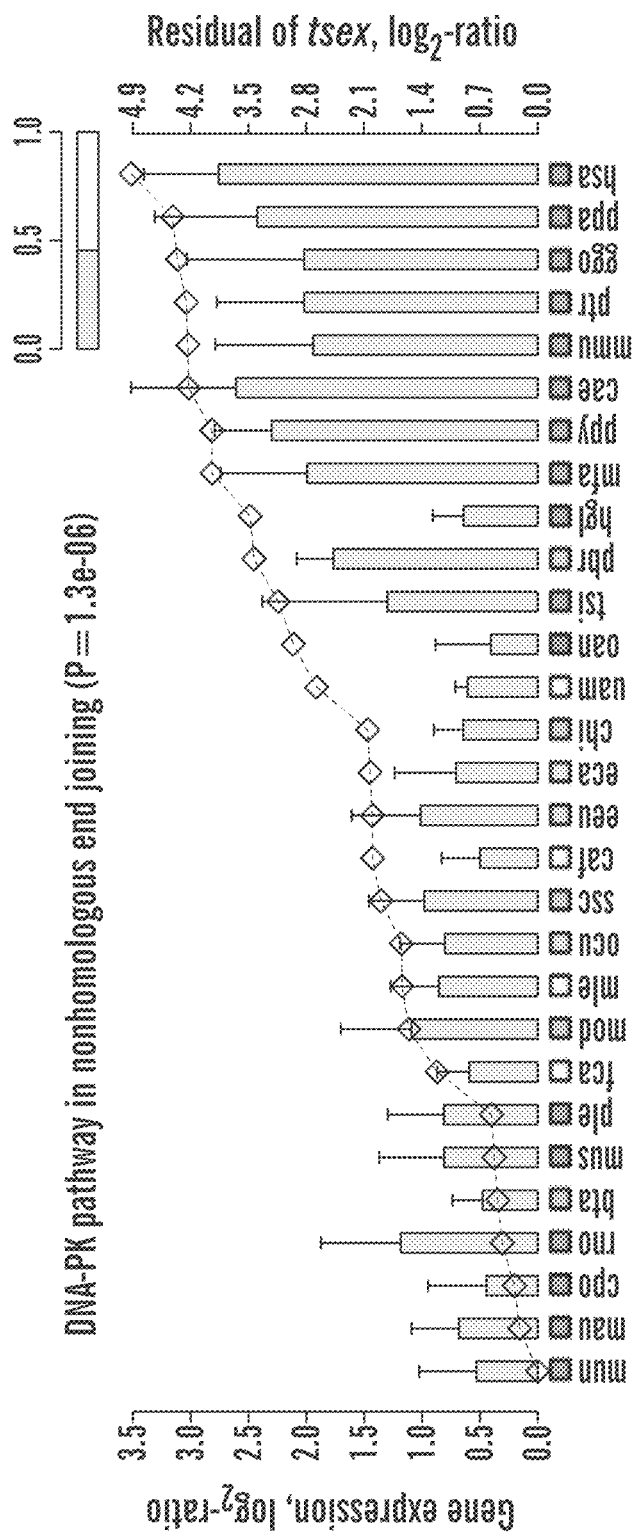
FIGS. 8A-8C. Gene expression variation associated with NHEJ positively correlates with residual of maximum lifespan and maturation time in liver.
Figure 8B:
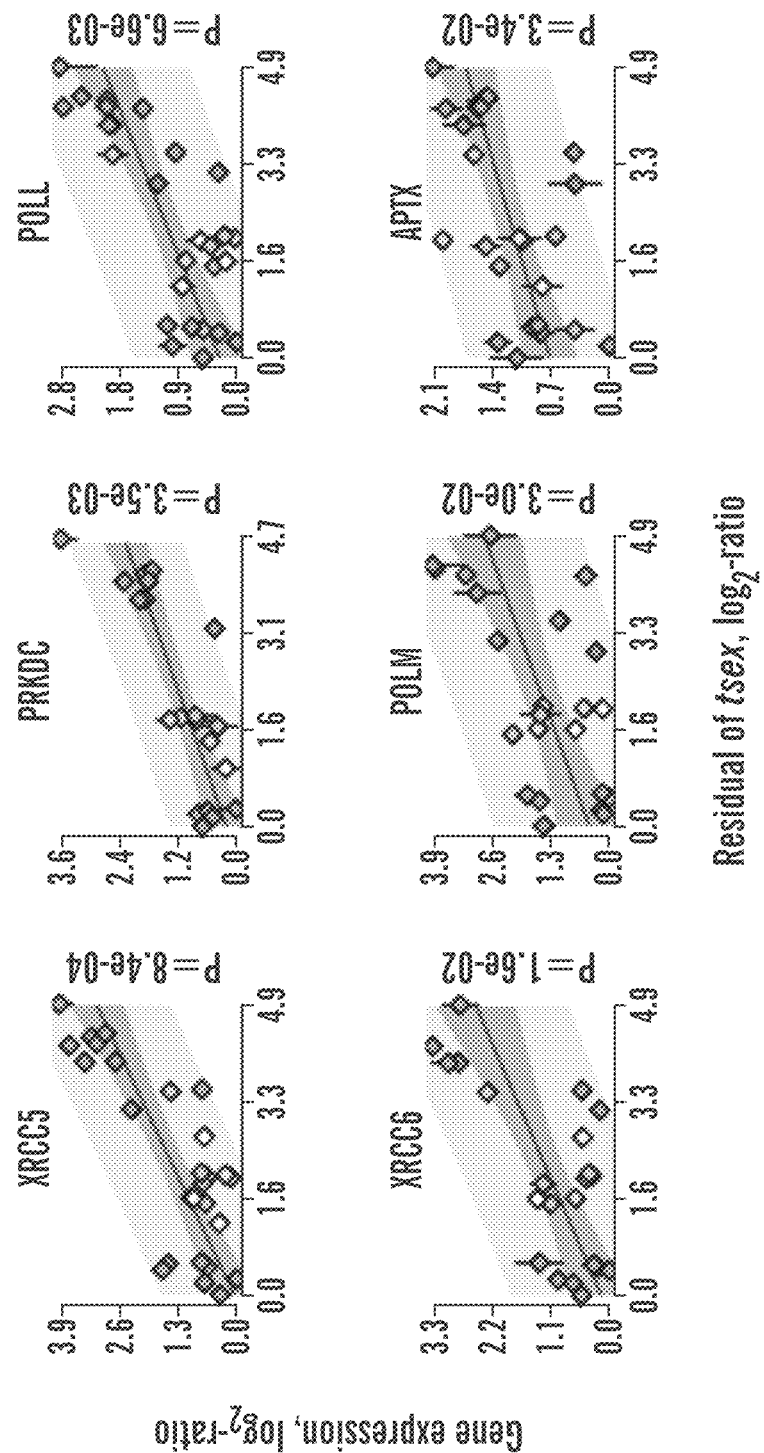
Figure 8C:
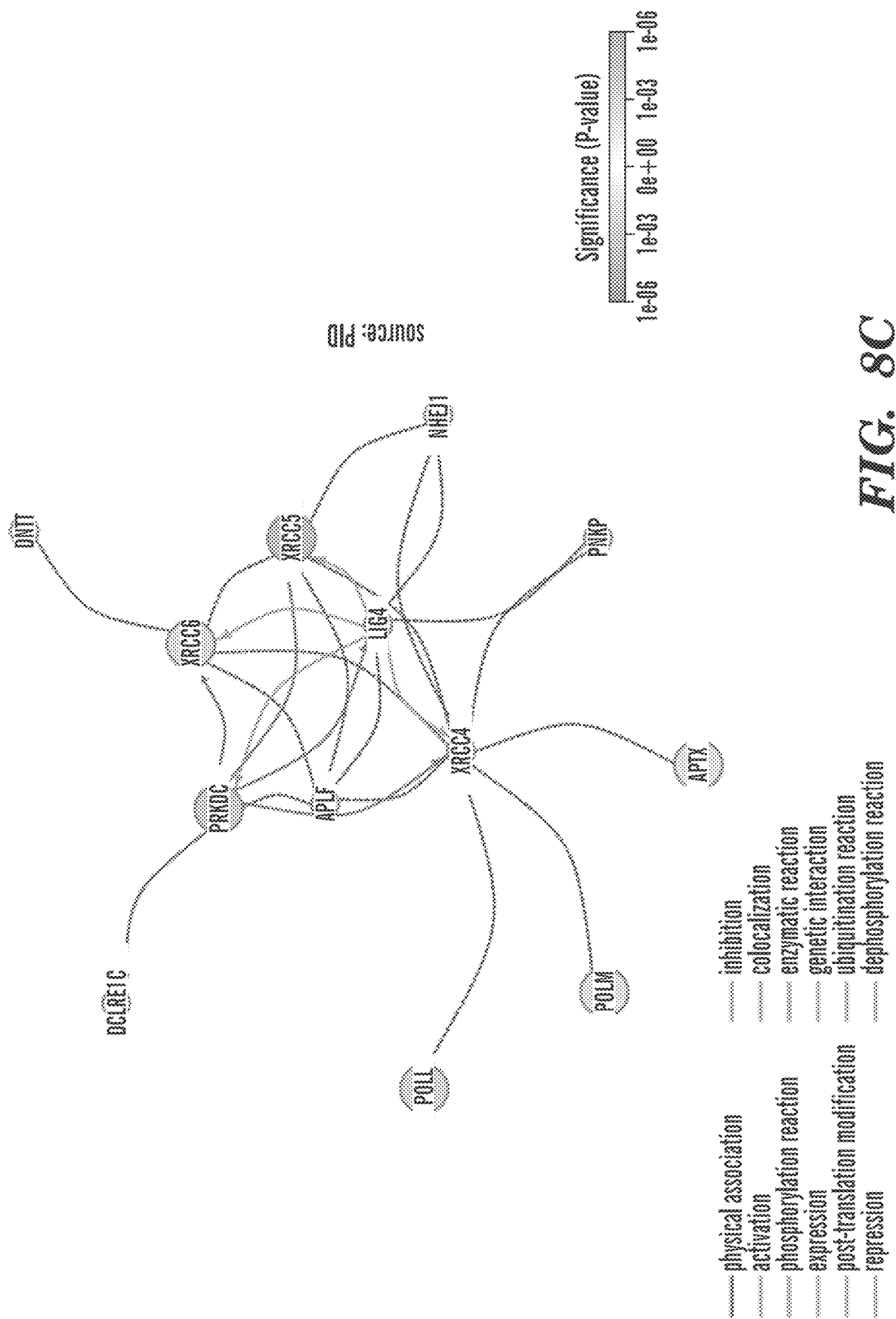

Gene set enrichment analysis indicated label overrepresentation in central metabolism, including mitochondrial and peroxisomal GO functions (FIG. 7C, Datasets 6 and 7 (not included)) and DNA repair such as non-homologous end-joining pathway (NHEJ) (data not shown). The latter pathway is predominantly upregulated in the Primate lineage. Genes associated with NHEJ (Xrcc5, Xrcc6, Prkdc, etc.) mediate telomeric and chromosomal DNA repair through interaction with Wrn, whose functional impairment may promote accelerated aging syndrome and genome instability in humans (Chai et al., 2002; Comai & Li, 2004; Ferguson et al., 2000). The processes involved in genome stability related to aging are likely to be more complex than an enhancement in simple NHEJ kinetics or telomere length, but may be related to maintenance of telomere capping (Lorenzini et al., 2009).

This is the first systemic report that provides a direct evidence of widespread selection on gene expression governed by evolution of whole-organism traits in mammals. Body weight exhibited greater constraints and probably influenced evolution of other life histories, such as lifespan and maturation time. There is a reciprocal interaction between forces that maximize fitness and equilibrium between life history traits. The analyses provide direct evidence that expression variation of at least ~11-18% orthologs exhibited constraints in heterologous mammalian organs and evolved in agreement with gradient of life history variation (Table 1). The data also indicate a predominant role of genetic, rather than environmental, control of interspecies gene expression divergence among currently living lineages, although environment likely contributed to this divergence over evolutionary timescales.

Although the data may reflect allometry and local adaptive responses of species to habitat, non-random association of gene expression variation with numerous biological functions related to central metabolism was observed. The magnitude of these changes was significantly correlated with gradient of life history variation. Without wishing to be bound by theory, this makes strong biological sense because reversible changes in organism-specific developmental dynamics during chronological evolution required flexible and adjustable instruments allowing allocating cellular resources, such as energy, for growth and reproduction.

The results are intriguing because numerous case studies of aging and dietary interventions such as caloric restriction (CR) also revealed gene expression alterations associated with mitochondrial metabolism, growth hormone and stress signaling pathways (Austad, 2009; Alic & Partridge, 2011; Anderson & Weindruch, 2009; Lee et al., 1999). For example, CR may reduce the levels of by-products by switching glucose degradation to gluconeogenesis and lowering the rate of mitochondrial metabolism in liver (Dhahbi et al., 1999; Hart et al., 1992). In the case of CR, the magnitude of inducible changes is small (Lee et al., 1999). An even stronger alteration in gene expression may promote longer survival of subjects, as evident from correlated variation in transcript levels and life history variation in mammals. Genes and biological processes reported in the study provide a valuable resource for examination of new candidate interventions that mimic gene expression changes associated with natural changes in species lifespan.

In Table 6, several compounds that shift gene expression in the direction of longevity have been identified or validated.

TABLE 6

Compounds that shift gene expression in the direction of longevity

| | Kidney | Brain | Liver |
|---|---|---|---|
| Increased lifespan | Rapamycin<br>Wortmannin<br>Irinotecan | Irinotecan<br>Wortmannin<br>Amantadine | Artemizole<br>Helveticoside<br>Resveratrol |

TABLE 6-continued

Compounds that shift gene expression in the direction of longevity

| | Kidney | Brain | Liver |
|---|---|---|---|
| Decreased lifespan | 15Δ prostaglandin J2<br>Tanespimycin<br>Lycorine | Tanespimycin<br>15Δ prostaglandin J2<br>Alvespimycin | Doxylamine<br>Monorden<br>15Δ prostaglandin J2 |

Example 2: Exemplary Materials and Methods

Animal Tissue Collection and RNA Extraction

The description and classification of mammals collected in this study is provided in Table 3. The 143 organ samples of 23 species were obtained from various sources. The collected species belong to *Euungulata* (domestic cattle, domestic goat, domestic boar, horse), *Carnivora* (domestic dog, domestic cat, Asian badger, American black bear), *Chiroptera* (greater tube-nosed bat, Brazilian free-tailed bat), *Didelphimorphia* (short-tailed opossum), *Diprotodoncia* (sugar glider), *Lagomorpha* (old world rabbit), *Primate* (vervet), *Rodentia* (spiny mouse, guinea pig, golden hamster, Mongolian gerbil, house mouse, white-footed mouse, Norway rat, Siberian chipmunk) and *Soricomorpha* (house shrew). The experimental protocols were approved by Institutional Animal Care and Use Committee (IACUC) of Ewha Women's University and Korea Research Institute of Bioscience and Biotechnology.

The organs examined in the study represent heterogeneous tissues whose structural and cellular composition varies among species. To account for this issue and maximize sample compatibility, major parts of each organ (covering different structures/cells) were dissected and homogenized prior to RNA extraction. Given that brain is a heterogeneous organ, prefrontal cortex/frontal lobe (*Primate, Euungulata, Carnivora, Diprotodoncia, Didelphimorphia, Lagomorph* asp.) or entire brain except for olfactory bulb and cerebellum (*Rodentia* and *Chrioptera* sp.) was sampled. Previous studies suggested that while the cortical regions substantially differ from the cerebellum in terms of gene expression (which is herein accounted for by the sampling procedure), different regions within the cerebral cortex show small expression variation (Khaitovich et al., 2004b).

Immediately after sacrificing, whole liver, kidney and brain tissue samples were frozen in liquid nitrogen and stored at −80° C. until further use. To ensure comparability of data derived from homologous organs between species, each organ was ground in liquid nitrogen-cooled mortar and used for RNA extraction. Most tissue samples were prepared in biological duplicates or triplicates to ensure biological variation in gene expression (Table 3). Total RNA was extracted using RNAEASY™ kit (QIAGEN™) according to the manufacturer's instructions. RNA integrity was assessed using an AGILEN™ 2100 Bioanalyser prior to library construction.

RNA Sequencing

Sequencing libraries were prepared using the mRNA-Seq Sample Prep Kit (ILLUMINA™, Inc.) in accordance with the manufacturer's instructions. Polyadenylated RNA was isolated using a poly-dT bead procedure, chemically fragmented and randomly primed for reverse transcription. After second-strand synthesis, the ends of the double-stranded complementary DNA were repaired. Following 3'-end adenylation of these products, ILLUMINA™ paired-end sequencing adapters were ligated to the blunt ends of the cDNA fragments. Ligated products were run on gels; 300-bp fragments were excised and then PCR-amplified (20 cycles). After column purification, quality of the resulting libraries was assessed using AGILENT™ 2100 Bioanalyser. Sequencing was done on the ILLUMINA™ HiSeq2000 platform generating approximately 30 million reads per sample.

RNA-Seq Read Mapping

Genome annotations (GTF) for 17 mammals with sequenced genomes were obtained from Ensembl, release 65. For the naked mole-rat (*H. glaber*), long-tailed macaque (*M. fasciularis*), bonobo (*P. paniscus*) and goat (*C. hircus*), GTF annotations downloaded from NCBI database (Data not shown) were used. 51-bp paired-end reads that passed the chastity filter threshold were mapped using TopHat™ 2.0 (Trapnell et al., 2012) with default parameter values, except for distance between mature pairs (r=200) and the number of allowable mismatches between read and genomic sequences (n=3) to account for a possible genetic variability between study and database organisms. The anchor size (i the minimum aligned length spanning each of the two exons that define a splice junction) was set at 8 bp, and 1 mismatch on the anchor region was permitted. The read alignments accepted by TopHat™ were filtered in order to remove mapping ambiguity. To do this, the best mapping(s) for each read were extracted, based on the number of mismatches in the alignment, and those reads for which the best mapping was unique were selected. Depending on species, final efficiency of RNA-seq read alignments varied from 55 to 99% (data not shown). Average gene expression levels were calculated as fragments per kilobase of exon per million fragments mapped (FPKM) and normalized using Cufflinks™ (Trapnell et al., 2012). An FPKM value of 3.0 was used to filter out low abundant transcripts.

De Novo Transcriptome Assembly

Draft transcriptomes for 12 species were de novo assembled using TRINITY™ (Grabherr et al., 2011). First, each RNA-seq reads set originating from an individual biological replicate was assembled and analyzed individually (data not shown). As the TRINITY™ assembler discards low coverage k-mers, no quality trimming of the reads was performed prior to the assembly. TRINITY™ was run on the 51-bp paired-end sequences with the fixed default k-mer size of 25, minimum contig length of 200, paired fragment length of 500, and a butterfly HeapSpace of 25G (i.e., allocated memory). To remove redundancy, contigs that overlapped with a minimum length of 50 bp and minimum identity of 99% were merged using CAP3 (Huang & Madan, 1999) to form the organ-specific transcriptome assemblies. Finally, the assemblies from individual organs were collapsed with CAP3 for the liver, kidney and brain to form a united reference assembly (Data not shown, FIG. 9).

FPKM Calculation for De Novo Transcriptomes

To calculate gene expression levels for de novo assembled transcripts, a strategy combining ab initio proteome prediction, redundancy elimination followed by FPKM calculation (data not shown) was developed. De novo assembled transcriptomic contigs represent a mix of non-coding, partial and complete cDNA sequences. The latter portion of molecules contains both start and stop signals and, therefore, can be treated as complete models in the ab initio protein prediction. AUGUSTUS™ v2.5 software (Stanke et al., 2006) was used with default parameters optimized for eukaryote gene prediction to refine amino acid sequences encoded by reference transcriptome assemblies (data not shown). Although de novo transcriptome assemblies were treated to eliminate redundant sequences, the ab initio predicted proteomes contained homologous sequences originating from software miss-assembly errors, highly homologous cDNA sequences and transcript isoforms. To filter out redundant amino acid sequences, USEARCH™ v6.0 software (Edgar, 2010) was applied with default parameters. The final sets of amino acid sequences were encoded by non-redundant longest transcripts expressed in the liver, kidney or brain organs (data not shown). GTF gene model annotations produced by AUGUSTUS™ software were used for calculations of FPKM values using TopHat™ and Cufflinks™ as described above.

Definition of Orthologous Genes

Sequence orthologous relationships for 17 mammalian species with sequenced genomes was obtained from Ensembl, version 65. Only 1:1 orthologs were considered in downstream analyses. Any other relationships, like uncertain relationships due to the presence of paralogous sequences, were excluded from the analysis. For ab initio peptides predicted in this study and protein sets from the naked mole-rat (*H. glaber*), long-tailed macaque (*M. fasciularis*), bonobo (*P. paniscus*) and goat (*C. hircus*), INPARANOID™ v4.1 software (Ostlund et al., 2009) was used with default parameters to refine initial 1:1 relationships with Ensembl peptides (data not shown). The software predicted heterogeneous relationships with distinct species in rare cases. Strict thresholds based on overall prediction performance (P >0.9, minor heterogeneity was allowed with frequency P<0.1) were applied to filter out molecules with inconsistent relationships from the dataset (data not shown). The final dataset of orthologous groups (COG) accounted for 19,643 individual groups of sequences is provided in Dataset 8 (not included).

Expression Level Normalization

Initially, FPKM values of each sample were normalized against single reference sample individually using upper quartile normalization, which outperforms other methods when applied to RNA-seq data (Dillies et al., 2013). $\log_2$-ratios centered on 0 were then calculated for every pair of orthologs of two samples. The procedure was cyclically repeated for every combination of samples. The final expression values were represented by a collection of log 2-ratios accounting for variation associated with normalization reference and biological variation between samples. Means values and standardized quantiles derived from the distribution of relative FPKM values were used in downstream analyses.

Data Quality Control

Some inherent biases can be present in the data collection and analysis. This includes de novo transcriptome assemblies for organisms for which no genome is currently available, as discussed above. In addition, organisms from published databases (primarily Primates) were used in the analysis even though some of them featured difference in read length, sequencing platform, sex (males were used herein, whereas some database organisms were females) and occasional alignment to closely related genomes. Nevertheless, it was found that the addition of these organisms to the pipeline improved the analysis. An analysis of traits is also less sensitive to issues with individual data points.

For further data quality control, a series of statistical tests were performed to filter out any poor quality samples from the analyses. Intra-species variation was assessed by examining CV defined as ratio of standard deviation to mean. Comparable degree of gene expression divergence among liver, kidney and brain was observed, which did not exceed the value of CV=0.6 and with mean values centered on CV=5 (data not shown). The results indicated that measurement and sampling errors as well as biological differences contribute little additional variation and that much of interspecies variation was due to distinct sources of variation.

Normalized gene expression values were examined visually and by the K-S and Welch's tests for any pair of organisms to ensure that resulting values were sampled from identical uniform distributions (data not shown). Any biological repeats with unusual deviation from homologous samples were excluded from the analysis. For RNA-seq libraries produced by previous studies (Brawand et al., 2011), FPKM values of homologous organs were compared for in-house data and CV was examined to ensure that the downloaded data contained no systemic instrumental or sampling errors (data not shown).

To verify the compatibility of FPKM calculated using conventional method (RNA-seq reads mapped to the genome) and FPKM calculated using de novo contigs, RNA transcripts were assembled using murine RNA-seq reads from liver, kidney and brain. Multiple orthologous relationships of ab initio predicted products with database sequences (excluding mouse database orthologs) were inferred. FPKM was then calculated for liver, kidney and brain and compared with FPKM produced from mouse genome alignments (data not shown). The analysis demonstrated no significant difference between FPKM produced by the two approaches (P=1, K-S test) and minor additional variation introduced by two methods (data not shown).

Amino Acid Sequence Conservation

The analysis of conservation aims to identify positions in a protein sequence which are conserved within each orthologous population that acquires this sequence. Such analysis also provides information about selection pressure acting across diverse protein groups and classes.

Conservation of a particular amino acid residue is defined as the average of the similarity scores of all pairwise comparisons for that position in the alignment, whereas the similarity score between any two residues is the score value between these residues in the chosen substitution matrix. An average conservation score for a group of amino acid sequences is a per residue similarity adjusted by the number of informative amino acids in the alignment.

The degree of evolutionary conservation within a family of homologous sequences was measured by Shannon's information entropy for a particular orthologous group:

$$S(l) = -\sum_{i=1}^{6} P_i(l) \log P_i(l) \quad (1.1)$$

where $P_i(l)$ is the frequency of each of the six classes i of residues at position l in the multiple sequence alignment (Mirny & Shakhnovich, 1999). The six classes of residues are: aliphatic (AVLIMC), aromatic (FWYH), polar (STNQ), positive (KR), negative (DE), and special (reflecting their special conformational properties) (GP). In addition to conservation, S(l) also reflects the level of amino acid substitutions between and within homologous sequences. A low value of the intrafamily conservation S(l) indicates that the particular amino acid position was under evolutionary pressure to keep a certain type of residue.

An average level of amino acid sequence diversity per amino acid residue for a particular orthologous group of sequences can be calculated as follows:

$$S = \frac{\sum_{k=1}^{N} S(l)}{N} \quad (1.2)$$

where S(l) is an information entropy for l-th residue and N is the number of informative amino acids in the alignment. The union $\{S_1, S_2 \ldots S_k\}$ provides an estimate of evolution conservation and divergence for a custom class of k orthologs.

Mammalian Phylogeny Reconstruction 436 common protein orthologs of 33 mammals (Dataset 9 (not included)) were aligned with MUSCLE™ v3.8 (Edgar, 2004) and produced a concatenated gap-free alignment with GBLOCKS™ v0.91 (Castresana, 2000). Respective genes were examined using PAML (Yang, 2007) for positive selection (M1a and M2a hypotheses) to validate that the encoded products exhibited nearly neutral evolution across branches. Species phylogeny was than reconstructed with the Neighbor-Joining method. The reliability of branching patterns was assessed in 1,000 bootstrapping replications using Mega™ 5.1 (Kumar et al., 2008) and PAML™ software.

Estimation of Divergence Time

For the concatenated multiple amino acid sequence alignment, a calibration range of 150-210 Mya for the divergence time was used. This range appears to be the most reliable for the divergence date between human and platypus, the most distant species in the dataset (Kumar & Subramanian, 2002). To calculate divergence time, PAML™ and MCMCTree™ (Yang, 2007) utilizing a Bayesian phylogenetic approach was used. The method accepts an upper and a lower bound on calibration points. Mammalian sequence evolution exhibits large rate differences within and between lineages (Kumar and Subramanian, 2002). Therefore, a global clock cannot be assumed for complex phylogenies. The independent substitution rate model was used in the reconstruction analysis. Divergence times were calculated using Whelan and Goldman (WAG) amino acid substitution matrix (Whelan and Goldman, 2001).

Definition of Whole-Organism Life History Traits

The data on life histories were collected from the ANAGE™ database (de Magalhaes & Costa, 2009) and literature in the case of rate of oxygen consumption (Heusner, 1991; Clarke et al., 2010; White and Seymour, 2003) and were cross-validated by independent sources such as the PanTHERTA™ database. Overall, 7 life history traits were examined in the study (data not shown). AnAge™ database internally traces the quality of population parameters with the number of subjects that were under observation and by the quality of data source. Poorly rated data ("tiny" sizes of populations or "unacceptable" quality) were excluded from the analyses.

Maximum lifespan (tmax) is the maximum time interval from birth to death documented for a given population of organisms within species. The accuracy of tmax depends on the sample size under observation and, therefore, the precision of its estimate can vary among lineages. The best estimate of tmax is available for human populations. tmax exhibits strong relationships with other traits such as time-to-maturity (de Magalhaes et al., 2009) estimated with greater precision for multitude species.

Oxygen consumption is the volume of oxygen consumed by an individual per an hour and, therefore, defines the intensity of resting (basal) metabolic rate (BMR). There is considerable correlation of BMR with body weight (White and Seymour, 2003). Thus, oxygen consumption with subtracted body weight component provides an unbiased estimate of BMR.

Statistical Analysis of Gene Expression and Life Histories

Analyses of gene expression and life histories were done using ordinary least squares (OLS). Life history variables (log 2-ratio) were examined for non-random association with relative values of FPKM under assumption that the error follows Gaussian distribution:

$$Y_i|x_1,x_2=\beta_0+\beta_1\bar{x}_1+\beta_2\bar{x}_2+\varepsilon_i, \varepsilon|x\sim N(0,\sigma^2 I_n) \quad (2.1)$$

where $Y_i$ is the average response for gene i, $x_1$ is the first explanatory variable, $x_2$ is the covariate predictor, $\beta_0$ is the intercept, $\varepsilon_i$ is the random error, $I_n$ is an n×n identity matrix, and $\sigma^2$ determines the variance of each observation.

OLS P-values (F-test) were then corrected with the Benjamini-Hochberg FDR-controlling procedure. A randomization test with $n=10^6$ replications was further used to ensure that the observed significance exceeds the level that can be obtained by chance. Distribution of inter- and intra-species expression variations were examined by Kruskal-Wallis one-way analysis of variance by ranks.

Label Overrepresentation Analysis

Label overrepresentation (gene set enrichment) analysis for functional annotation, ontology and pathways were performed using standard right-sided hypergeometric test employing all genes on the array as denominator and genes under interest as numerator (Huang et al., 2009). P-values were corrected by the Benjamini-Hochberg FDR-controlling procedure.

Application of the Brownian Motion Model to Character Evolution

The Brownian motion (BM) model, developed for analyses of numerical traits evolving along a given phylogenetic pattern, was used to model evolution of life histories. The BM theory assumes a linear accumulation of changes in a numerical trait over time (Boettiger et al., 2012; Freckleton & Harvey, 2006). For particular values at ancestral nodes, the likelihood (L) of observing a set of phenotypic data for a single character at the tips of ultrameric phylogenetic tree can be represented as:

$$L = \prod \frac{1}{\sqrt{2\pi(v_{n1}+v_{n2})}} \exp\left[-\frac{(x_{n1}-x_{n2})^2}{2(v_{n1}+v_{n2})}\right] \quad (3.1)$$

where L is the product over all nodes on the tree; n indicates a particular node and N is the total number of nodes (Freckleton & Harvey, 2006). The term $(x_{n1}-x_{n2})$ is the difference in trait values at two descendents of each node n. $v_{n1}$ and $v_{n2}$ are variance values derived from the branch lengths of the phylogeny in units of expected amount of time available for phenotypic change along branches of the tree.

Several approaches have been proposed for estimation of the likelihood parameter (Blomberget et al., 2003). A phylogenetic covariance was constructed from the phylogenetic tree to evaluate the BM process and calculated parameter lambda ($\lambda$). $\lambda$ is a branch length scaling parameter that was allowed to range from 0 to 1 (Pagel, 1999). With the tree in this variance-covariance matrix form, $\lambda$ scales the off-diagonal elements of the matrix by the amount of coefficient. It moves from 1 to 0 the shorter the internal branches. The final tree is star-like with all branches emanating from a common node. When $\lambda=1$, there was no transformation that corresponds to the BM of the trait along the phylogenetic pattern. When $\lambda=0$, co-variances are zero, corresponding to random noise. A star-like tree reflects less phylogenetic structure, that is, less phylogenetic signal.

To test the significance of the $\lambda$ model, log-likelihoods of the BM model for original (where it is allowed to take its maximum value) and star-like topologies were estimated and the ratio between log-likelihoods of these models and the $\lambda$ model was calculated. The probability that the observed value of $\lambda$ differs from random distribution and the probability of deviation from the BM process were then estimated using chi-squared distributions (Pagel, 1999).

A measurement error in the data was accounted for (data not shown). The sources of measurement error include sampling variation, variation related to age, sex, season, etc. Although estimating the total measurement error (e.g., the variation among all populations of a species) is unrealistic, incorporating the measurement error associated with the observations provides substantial improvement to the method (Ives et al., 2007).

Under the $\lambda$ model the multivariate distribution of tip values is $x\sim\sigma^2 C_\lambda$, where $C_\lambda$ is an n×n matrix for n species containing, in the diagonal, the height of each species above the root, and in each off-diagonal element $C_\lambda(i,j)$, the height above the root node of the most common recent ancestor of species i and j multiplied by the coefficient With measurement error $x\sim\sigma^2 C_\lambda+E$, where E is a diagonal matrix containing the square of the estimation error for each species and $E\sim\sigma^2_m M$. The variance due to measurement error M of trait x for species i is $\sigma^2_m m_{ij}$ where $m_{ij}$ is the i-th diagonal element of M. Therefore, the distribution of tip values among species is:

$$x=a+\varepsilon+\eta, \varepsilon+\eta\sim\sigma^2 C_\lambda+\sigma_m^2 M \quad (3.2)$$

where x is a N×1 vector containing the observed values of the trait, a is a scalar giving the expected value of the trait, $\varepsilon$ is a N×1 vector of zero-mean error terms depicting the evolutionary variance of the trait among species, and $\eta$ is the N×1 vector of errors associated with measurement (Ives et al., 2007).

Databases

For pathway and gene ontology analyses, latest builds of CPDB (Kamburov et al., 2009) and gene ontology consortium databases (Ashburner et al., 2000) were used respectively. CPDB is a comprehensive database of biochemical pathways that accumulates data from KEGG, Reactome, HumanCyc and related sources. Electronically inferred GO annotations (RCA, IEA, NR and ND codes) were excluded from gene ontology enrichment analyses. Protein-protein interactions were obtained from CPDB and STRING 9.0 (Szklarczyk et al., 2010). Only highly confident interactions as defined by the original sources were used in biological network analyses.

Primary Accessions

Raw sequencing data and gene expression for 143 biological samples have been deposited into Gene Expression Omnibus under accession GSE43013. All RNA-seq read data have been deposited into the Short Read Archive database. Transcriptome shotgun assembly projects and contig annotations were deposited to DDBJ/EMBL/GenBank under the following accession numbers: PRJNA182762 (*C. aethiops*), PRJNA182763 (*C. hircus*), PRJNA182765 (*M. auratus*), PRJNA182766 (*M. leucogaster*), PRJNA182767 (*M. meles*), PRJNA182768 (*M. unguiculatus*), PRJNA182769 (*P. breviceps*), PRJNA182770 (*P. leucopus*).

PRJNA182771 (*S. murinus*), PRJNA1827722, (*T. brasiliensis*), PRJNA182773 (*U. americanus*), PRJNA182705 (*A. cahirinus*), PRJNA183188 (*T. sibiricus*).

REFERENCES CITED THROUGHOUT SPECIFICATION

Abzhanov. A., Protas, M., Grant, B. R., Grant, P. R. & Tabin, C. J. (2004) Bmp4 and morphological variation of beaks in Darwin's finches. Science 305, 1462-1465.

Alic, N. & Partridge, L. (2011) Death and dessert: nutrient signalling pathways and ageing. Curr. Opin. Cell. Biol. 23, 738-743.

Anderson, R. M. & Weindruch, R. (2009) Metabolic reprogramming, caloric restriction and aging. Trends Endocrinol. Metab. 21, 134-141.

Ashburner, M. et al. (2000) Gene ontology: tool for the unification of biology. The Gene Ontology Consortium. Nat. Genet. 25, 25-29.

Austad, S. N. (2009) Comparative biology of aging. J. Gerontol. A Biol. Sci. Med. Sci. 64, 199-201.

Barbosa-Morais, N. L. et al. (2012) The evolutionary landscape of alternative splicing in vertebrate species. Science 338, 1587-1593.

Barja, G. (1998) Mitochondrial free radical production and aging in mammals and birds. Ann. N. Y. Acad. Sci. 854, 224-238.

Beldade, P., Brakefield, P. M. & Long, A. D. (2002) Contribution of Distal-less to quantitative variation in butterfly eyespots. Nature 415, 315-318.

Blomberg, S. P., Garland, T., Jr. & Ives, A. R. (2003) Testing for phylogenetic signal in comparative data: behavioral traits are more labile. Evolution 57, 717-745.

Boettiger C, Coop G, Ralph P (2012). Is your phylogeny informative? Measuring the power of comparative methods. Evolution. 66, 2240-2251.

Brawand, D. et al. (2011) The evolution of gene expression levels in mammalian organs. Nature 478, 343-348.

Burbea, Z, et al. (2004) Role of haptoglobin phenotype in end-stage kidney disease. Nephron Exp. Nephrol. 97, e71-e76.

Carroll, S. B. (2005) Evolution at two levels: on genes and form. PLoS Biol, 3, e245.

Castresana, J. (2000) Selection of conserved blocks from multiple alignments for their use in phylogenetic analysis. Mol. Biol. Evol. 17, 540-552.

Chai, W., Ford, L. P., Lenertz, L., Wright, W. E. & Shay, J. W. (2002) Human Ku70/80 associates physically with telomerase through interaction with hTERT. J. Biol. Chem. 277, 47242-47247.

Clarke, A., Rothery, P. & Isaac, N. J. (2010) Scaling of basal metabolic rate with body mass and temperature in mammals. J. Anim. Ecol. 79, 610-619.

Comai, L. & Li, B, (2004) The Werner syndrome protein at the crossroads of DNA repair and apoptosis. Mech. Ageing. Dev. 125, 521-528.

Coolon J D, McManus C J, Stevenson K R, Graveley B R, Wittkopp P J (2014). Tempo and mode of regulatory evolution in *Drosophila*. Genome Res. 24, 797-808.

Coschigano, K. T. et al. (2003) Deletion, but not antagonism, of the mouse growth hormone receptor results in severely decreased body weights, insulin, and insulin-like growth factor I levels and increased life span. Endocrinology 144, 3799-3810.

Danko, M. J., Kozlowski, J., Vaupel, J. W. & Baudisch, A. (2012) Mutation accumulation may be a minor force in shaping life history traits. PLoS One 7, e34146.

de Magalhaes, J. P., Costa, J. & Church, G. M. (2007) An analysis of the relationship between metabolism, developmental schedules, and longevity using phylogenetic independent contrasts. J. Gerontol. A Biol. Sci. Med. Sci. 62, 149-160.

de Magalhaes, J. P. & Costa, J. (2009) A database of vertebrate longevity records and their relation to other life-history traits. J. Evol. Biol. 22, 1770-1774.

Dhahbi, J. M. et al, (1999) Calories and aging alter gene expression for gluconeogenic, glycolytic, and nitrogen-metabolizing enzymes. Am. J. Physiol. 277, E352-360.

Dillies, M. A. et al. (2013) A comprehensive evaluation of normalization methods for Illumina high-throughput RNA sequencing data analysis. Brief, Bioinform. 14, 671-683.

Duret, L. & Mouchiroud, D. (2000) Determinants of substitution rates in mammalian genes: expression pattern affects selection intensity but not mutation rate. Mol. Biol. Evol. 17, 68-74.

Edgar, R. C. (2004) MUSCLE: multiple sequence alignment with high accuracy and high throughput. Nucleic Acids Res. 32, 1792-1797.

Edgar, R. C. (2010) Search and clustering orders of magnitude as than BLAST, Bioinformatics 26, 2460-2461.

Fagoonee, S. et al. (2005) Plasma protein haptoglobin modulates renal iron loading. Am. J. Pathol. 166, 973-983.

Ferguson, D. O. et al. (2000) The nonhomologous end-joining pathway of DNA repair is required for genomic stability and the suppression of translocations. Proc. Natl. Acad. Sci. USA 97, 6630-6633.

Fraser, H. B. (2013) Gene expression drives local adaptation in humans. Genome Res. 23, 1089-1096.

Freckleton R P, Harvey P H (2006). Detecting non-Brownian trait evolution in adaptive radiations. PLoS Biol. 4, e373.

Giger, T. et al, (2006) Life history shapes gene expression in salmonids. Curr. Biol. 16, R281-R282.

Gompel, N., Prud'homme, B., Wittkopp, P. J., Kassner, V. A. & Carroll, S. B. (2005) Chance caught on the wing: cis-regulatory evolution and the origin of pigment patterns in *Drosophila*. Nature 433, 481-487.

Gladyshev V N (2013). The origin of aging: imperfectness-driven non-random damage defines the aging process and control of lifespan. Trends Genet. 29, 506-512.

Grabherr, M. G. et al. (2011) Full-length transcriptome assembly from RNA-Sect data without a reference genome. Nat. Biotechnol. 29, 644-652.

Hart, R. W. & et al. (1992) Modulation of chemical toxicity by modification of caloric intake. Adv. Exp. Med. Biol. 322, 73-81.

Heusner, A. A. (1991) Size and power in mammals. J. Evol. Biol. 160, 25-54.

Houtkooper, R. H. et al. (2012) The metabolic footprint of aging in mice. Sci. Rep. 1, 134.

Huang, X. & Madan, A. (1999) CAP3: A DNA sequence assembly program. Genome Res 9: 868-877, Huang da, W., Sherman, B. T. & Lempicki, R. A. (2009) Bioinformatics enrichment tools: paths toward the comprehensive functional analysis of large gene lists, Nucleic Acids Res, 37, 1-13.

Ives A R, Midford P E, Garland T, Jr. (2007). Within-species variation and measurement error in phylogenetic comparative methods. Syst Biol. 56, 252-270.

Janecka, J., Chowdhary, B. & Murphy, W. (2012) Exploring the correlations between sequence evolution rate and phenotypic divergence across the Mammalian tree provides insights into adaptive evolution. J. Biosci. 37, 897-909.

Jordan, K., Marino-Ramirez, L. & Koonin, E. V. (2005) Evolutionary significance of gene expression divergence. Gene 34, 119-126, Kamburov, A., Wierling, C., Lehrach, H. & Herwig, R, (2009) ConsensusPathDB—a database for integrating human functional interaction networks. Nucleic Acids Res. 37, D623-628.

Kawasaki N, Brassil C E, Brooks R C, Bonduriansky R (2008). Enviromnental effects on the expression of life span and aging: an extreme contrast between wild and captive cohorts of Telostylinus angusticollis (Diptera: Neriidae). Am Nat. 172, 346-357.

Khaitovich, P. et al. (2004) A neutral model of transcriptome evolution. PLoS Biol. 2, E132.

Khaitovich, R et al. (2005) Parallel patterns of evolution in the genomes and transcriptotnes of humans and chimpanzees. Science 309, 1850-1854.

Kim, E. B. et al. (2011) Genome sequencing reveals insights into physiology and longevity of the naked mole rat. Nature 479, 223-227.

Kumar, S. & Subramanian. S. (2002) Mutation rates in mammalian genomes, Proc. Natl. Acad. Sci. USA 99, 803-808.

Kumar, S., Nei, M., Dudley, J. & Tamura, K. (2008) MEGA: a biologist-centric software for evolutionary analysis of DNA and protein sequences. Brief. Bioinfonn. 9, 299-306.

Lee. C. K., Klopp, R. G., Weindruch, R. & Prolla, T. A. (1999) Gene expression profile of aging and its retardation by caloric restriction, Science 285, 1390-1393.

Li, Y. & de Magalhaes, J. P. (2011) Accelerated protein evolution analysis reveals genes and pathways associated with the evolution of mammalian longevity. Age (Dordr) 35, 301-314, Lorenzini A, Johnson F B, Oliver A, Tresini M, Smith J S, Hdeib M, Sell C, Cristofalo V J, Stamato T D (2009). Significant correlation of species longevity with DNA double strand break recognition but not with telomere length. Mech Ageing Dev. 130, 784-792.

Losos, J. B., Jackman, T. R., Larson, A., Queiroz, K. & Rodriguez-Schettino, L. (1998) Contingency and determinism in replicated adaptive radiations of island lizards. Science 279, 2115-2118.

Mirny, L. A. & Shakhnovich, E. I. (1999) Universally conserved positions in protein folds: reading evolutionary signals about stability, folding kinetics and function. J. Mol. Biol. 291, 177-196.

Misawa, K. & Kikuno, R. F. (2011) Relationship between amino acid composition and gene expression in the mouse genome. BMC Res. Notes, 4, 20.

Ostlund, G. et al. (2009) InParanoid 7: new algorithms and tools for eukaryotic orthology analysis. Nucleic Acids Res. 38, D196-D203, Pagel M (1999). Inferring the historical patterns of biological evolution. Nature. 401, 877-884.

Panici, J. A. et al. (2010) Early life growth hormone treatment shortens longevity and decreases cellular stress resistance in long-lived mutant mice. FASEB J. 24, 5073-5079.

Plank, M., Wuttke, D., van Dam, S., Clarke, S. A. & de Magalhaes, J. P. (2012) A meta-analysis of caloric restriction gene expression profiles to infer common signatures and regulatory mechanisms. Mol. Biosyst. 8, 1339-1349.

Puffer K, et al., (2012). The bonobo genome compared with the chimpanzee and human genomes. Nature. 486, 527-531.

Quarrie, J. K. & Riabowol, K. T. (2004) Murine models of life span extension. Sci Aging Knowledge Environ. 2004, re5.

Revell L J. (2010), Phylogenetic signal and linear regression on species data. Methods in Ecology and Evolution. 1, 319-329.

Romero I G, Ruvinsky I, Gilad Y (2012). Comparative studies of gene expression and the evolution of gene regulation. Nat Rev Genet. 13, 505-516.

Schwanhausser, B, et al. (2011) Global quantification of mammalian gene expression control. Nature 473, 337-342.

Semeiks, J, & Grishin, N. V. (2012) A method to find longevity-selected positions in the mammalian proteome. PLoS One 7, e38595.

Shapiro, M. D. et al. (2004) Genetic and developmental basis of evolutionarypelvic reduction in threespine sticklebacks. Nature 428, 717-723.

St-Cyr, J., Demme, N. & Bernatchez, L. (2008) The transcriptomics of life-history trade-offs in whitefish species pairs (Coregonus sp.). Mol. Ecol. 17, 1850-1870.

Stanke, M., Schoffmann, O., Morgenstern, B. & Waack, S. (2006) Gene prediction in eukaryotes with a generalized hidden Markov model that uses hints from external sources. BMC Bioinformatics 7, 62.

Steams, S. C. (2000) Life history evolution: successes, limitations, and prospects. Naturwissenschaften 87, 476-486.

Szklarczyk, D, et al. (2010) The STRING database in 2011: functional interaction networks of proteins, globally integrated and scored. Nucleic Acids Res. 39, D561-D568.

Tofts, R. & Silvertown, J. (2000) A phylogenetic approach to community assembly from a local species pool, Proc. Biol. Sci. 267, 363-369.

Trapnell, C. et al. (2012) Differential gene and transcript expression analysis of RNA-seq experiments with TopHat and Cufflinks. Nat. Protoc. 7, 562-578.

Wang, S. et al. (2010) Switch between life history strategies due to changes in glycolytic enzyme gene dosage in Saccharomyces cerevisiae, Appl. Environ. Microbiol. 77, 452-459.

Whelan, S. & Goldman, N. (2001) A general empirical model of protein evolution derived from multiple protein families using a maximum-likelihood approach. Mol, Biol. Evol., 18, 691-699.

White, C. R. & Seymour, R. S. (2003) Mammalian basal metabolic rate is proportional to body mass2/3. Proc. Natl. Acad. Sci. USA 100, 4046-4049.

Whitehead, A. & Crawford, D. L. (2006a) Neutral and adaptive variation in gene expression. Proc. Natl. Acad. Sci. USA 103, 5425-5430.

Whitehead A, Crawford. D L (2006b). Variation within and among species in gene expression: raw material for evolution. Mol Ecol. 15, 1197-1211.

Yan, G. et al. (2011) Genome sequencing and comparison of two nonhuman primate animal models, the cynomolgus and Chinese rhesus macaques. Nat. Biotechnol. 29: 1019-1023.

Yanai, I., Graur, D. & Ophir, R. (2004) Incongruent expression profiles between human and mouse orthologous genes suggest widespread neutral evolution of transcription control. OMICS 8, 15-24.

Yang, Z. (2007) PAML 4: phylogenetic analysis by maximum likelihood. Mol. Biol. Evol. 24, 1586-1591.

Yuan, R., Peters, L. L. & Paigen, B. (2011) Mice as a mammalian model for research on the genetics of aging. ILAR J. 52, 4-15.

What is claimed is:

1. A method comprising:
   (a) contacting a mammalian liver cell, or liver cell line derived from a mammalian subject with a library of chemical compounds;
   (b) determining whether genes of a gene expression profile are upregulated or downregulated by measuring in the mammalian liver cell or liver cell line of step (a), wherein the gene expression profile consists essentially of: (i) genes HP and HPX, and (ii) genes GHR, JAK2, STAT5B, IGF1, ULK2, ATG7, SOS1, PIK3CA, TSC1, S6K1, DEPTOR, IPMK, PRKAA2, CAB39L, FABP2, FABP7, PPARA and RXRG;
   wherein upregulated genes and downregulated genes are determined by comparing the measured gene expression profile to the expression of the same genes measured in a substantially similar mammalian liver cell or liver cell line derived from the mammalian subject and that has not been contacted with the library of chemical compounds, and
   (c) calculating a longevity score by summing the number of genes from (b)(i) that were determined to be upregulated and the number of genes from step (b)(ii) that were determined to be downregulated and comparing the resulting longevity score with a reference longevity score,
   wherein the reference longevity score is calculated by summing the number of genes in (b)(i) determined to be upregulated and genes in (b)(ii) determined to be down-regulated from a gene expression profile determined for the 20 genes derived from a reference population of liver cells derived from mammalian subjects treated with a geroprotector,
   (d) identifying a chemical compound of the library as a treatment that modulates lifespan when the longevity score of step (c) is at least 75% similar to the reference longevity score, and
   (e) administering the treatment identified in step (d) to the mammalian subject, thereby increasing the lifespan of the mammalian subject.

2. The method of claim 1, wherein the mammalian subject is a human.

3. The method of claim 1, wherein the geroprotector comprises rapamycin, wortmannin, irinotecan, amantadine, astemizole, helveticoside, or reveratrol.

* * * * *